(12) United States Patent
Ciopyk et al.

(10) Patent No.: US 11,952,636 B2
(45) Date of Patent: *Apr. 9, 2024

(54) DEVICES AND METHODS FOR ANTIBIOTIC SUSCEPTIBILITY TESTING

(71) Applicant: Visby Medical, Inc., San Jose, CA (US)

(72) Inventors: Brian Ciopyk, Santa Clara, CA (US); Paul Dentinger, Sunol, CA (US); Teresa Abraham, Washington, DC (US); Brandon Ma, Santa Clara, CA (US); Kamal Kajouke, San Jose, CA (US); Mackenzie Hunt, Santa Cruz, CA (US); Austin Phung, San Jose, CA (US); Karl Guegler, Menlo Park, CA (US); David Swenson, Santa Clara, CA (US); Anna H. Postlethwaite, Longmont, CO (US)

(73) Assignee: Visby Medical, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/738,979

(22) Filed: May 6, 2022

(65) Prior Publication Data

US 2022/0372557 A1 Nov. 24, 2022

Related U.S. Application Data

(62) Division of application No. 17/139,451, filed on Dec. 31, 2020, now Pat. No. 11,352,675.
(Continued)

(51) Int. Cl.
*C12P 19/34* (2006.01)
*C12Q 1/04* (2006.01)
(Continued)

(52) U.S. Cl.
CPC ............... *C12Q 1/689* (2013.01); *C12Q 1/04* (2013.01); *C12Q 1/18* (2013.01)

(58) Field of Classification Search
CPC .................................................. C12Q 1/689
See application file for complete search history.

(56) References Cited

U.S. PATENT DOCUMENTS

| 4,789,630 A | 12/1988 | Bloch et al. |
| 5,229,297 A | 7/1993 | Schnipelsky et al. |
| (Continued) | | |

FOREIGN PATENT DOCUMENTS

| CN | 103820439 | 5/2014 |
| CN | 108884489 A | 11/2018 |
| (Continued) | | |

OTHER PUBLICATIONS

Ahrberg, Christian D. et al. "Polymerase chain reaction in microfluidic devices," © The Royal Society of Chemistry 2016, Lab Chip, 16, pp. 3866-3884, 20 pgs.
(Continued)

*Primary Examiner* — Kenneth R Horlick
(74) *Attorney, Agent, or Firm* — Cooley LLP

(57) ABSTRACT

The disclosure relates generally to molecular diagnostic devices configured to amplifying a single nucleotide polymorphism (SNP) locus and discriminate between two or more allelic variants of the SNP, indicating presence or absence of a target allele. In some embodiments, the molecular diagnostic devices are capable of detecting, at point-of-care, SNPs associated with resistance or susceptibility to antibiotic treatment of organism infections. In other aspects, the disclosure provides methods of treatment for disease or disorders (e.g. organism infections) where treatment is
(Continued)

guided by presence or absence of an allele at a SNP locus as determined by such molecular diagnostic devices.

20 Claims, 32 Drawing Sheets

Specification includes a Sequence Listing.

Related U.S. Application Data

(60) Provisional application No. 62/957,068, filed on Jan. 3, 2020.

(51) Int. Cl.
*C12Q 1/18* (2006.01)
*C12Q 1/689* (2018.01)

(56) References Cited

U.S. PATENT DOCUMENTS

| | | | |
|---|---|---|---|
| 5,498,392 A | 3/1996 | Wilding et al. |
| 5,726,026 A | 3/1998 | Wilding et al. |
| 5,882,903 A | 3/1999 | Andrevski et al. |
| 5,922,591 A | 7/1999 | Anderson et al. |
| 6,146,591 A | 11/2000 | Miller |
| 6,153,425 A | 11/2000 | Kozwich et al. |
| 6,235,479 B1 | 5/2001 | Rogers |
| 6,369,893 B1 | 4/2002 | Christel et al. |
| 6,374,684 B1 | 4/2002 | Dority |
| 6,610,499 B1 | 8/2003 | Fulwyler et al. |
| 6,645,758 B1 | 11/2003 | Schnipelsky et al. |
| 6,780,617 B2 | 8/2004 | Chen |
| 6,821,771 B2 | 11/2004 | Festoc |
| 6,893,879 B2 | 5/2005 | Petersen et al. |
| 7,156,809 B2 | 1/2007 | Quy |
| 7,189,522 B2 | 3/2007 | Esfandiari |
| 7,297,313 B1 | 11/2007 | Northrup et al. |
| 7,384,782 B2 | 6/2008 | Nakatani et al. |
| 7,416,892 B2 | 8/2008 | Battrell et al. |
| 7,553,675 B2 | 6/2009 | Jerome et al. |
| 7,569,382 B2 | 8/2009 | Li |
| 7,579,172 B2 | 8/2009 | Cho et al. |
| 7,592,139 B2 | 9/2009 | West et al. |
| 7,648,835 B2 | 1/2010 | Breidford et al. |
| 7,705,339 B2 | 4/2010 | Smith et al. |
| 7,754,452 B2 | 7/2010 | Kim et al. |
| 7,767,439 B2 | 8/2010 | Oh et al. |
| 7,799,521 B2 | 9/2010 | Chen et al. |
| 7,914,986 B2 | 3/2011 | Nunn |
| 7,985,716 B2 | 7/2011 | Yershov et al. |
| 7,998,757 B2 | 8/2011 | Darrigrand et al. |
| 8,018,593 B2 | 9/2011 | Tan et al. |
| 8,048,386 B2 | 11/2011 | Dority et al. |
| 8,088,616 B2 | 1/2012 | Handique |
| 8,110,392 B2 | 2/2012 | Battrell et al. |
| 8,133,671 B2 | 3/2012 | Williams et al. |
| 8,133,703 B2 | 3/2012 | Ching et al. |
| 8,163,535 B2 | 4/2012 | Reed et al. |
| 8,169,610 B2 | 5/2012 | Oldham et al. |
| 8,187,557 B2 | 5/2012 | Van Atta et al. |
| 8,216,832 B2 | 7/2012 | Battrell et al. |
| 8,232,091 B2 | 7/2012 | Maltezos et al. |
| 8,232,094 B2 | 7/2012 | Hasson et al. |
| 8,298,763 B2 | 10/2012 | Regan |
| 8,329,453 B2 | 12/2012 | Battrell et al. |
| 8,343,442 B2 | 1/2013 | McBride et al. |
| 8,343,754 B2 | 1/2013 | Wittwer et al. |
| 8,372,340 B2 | 2/2013 | Bird et al. |
| 8,389,960 B2 | 3/2013 | Pieprzyk et al. |
| 8,394,608 B2 | 3/2013 | Ririe et al. |
| 8,426,134 B2 | 4/2013 | Piepenburg et al. |
| 8,492,136 B2 | 7/2013 | Carlisle et al. |
| 8,557,518 B2 | 10/2013 | Jovanovich et al. |
| 8,637,250 B2 | 1/2014 | Jenison |
| 8,722,426 B2 | 5/2014 | Lambotte et al. |
| 8,728,765 B2 | 5/2014 | Ching et al. |
| 8,765,367 B2 | 7/2014 | Breidenthal et al. |
| 8,765,454 B2 | 7/2014 | Zhou et al. |
| 8,772,017 B2 | 7/2014 | Battrell et al. |
| 8,795,592 B2 | 8/2014 | Eiriksson |
| 8,894,946 B2 | 11/2014 | Nielsen et al. |
| 8,895,255 B1 | 11/2014 | Goldberg et al. |
| 8,900,828 B2 | 12/2014 | Smith et al. |
| 8,911,941 B2 | 12/2014 | Michlitsch |
| 8,911,949 B2 | 12/2014 | Bertrand et al. |
| 8,916,375 B2 | 12/2014 | Landers et al. |
| 8,945,843 B2 | 2/2015 | Alvino et al. |
| 8,975,027 B2 | 3/2015 | Gale et al. |
| 8,980,561 B1 | 3/2015 | Cai et al. |
| 9,012,236 B2 | 4/2015 | Jovanovich et al. |
| 9,023,639 B2 | 5/2015 | Kim et al. |
| 9,034,168 B2 | 5/2015 | Khattak et al. |
| 9,044,729 B2 | 6/2015 | Rengifo et al. |
| 9,150,907 B2 | 10/2015 | Shaikh et al. |
| 9,207,236 B2 | 12/2015 | Cary |
| 9,238,833 B2 | 1/2016 | Chen et al. |
| 9,260,750 B2 | 2/2016 | Hillebrand et al. |
| 9,387,478 B2 | 7/2016 | Bergstedt et al. |
| 9,428,781 B2 | 8/2016 | Cai et al. |
| 9,445,749 B2 | 9/2016 | Erickson et al. |
| 9,453,255 B2 | 9/2016 | Ozawa et al. |
| 9,469,871 B2 | 10/2016 | Bearinger et al. |
| 9,475,049 B2 | 10/2016 | Siciliano |
| 9,623,415 B2 | 4/2017 | Andreyev et al. |
| 9,663,821 B2 | 5/2017 | Unger et al. |
| 9,718,058 B2 | 8/2017 | Khattak et al. |
| 9,725,754 B2 | 8/2017 | Boyle et al. |
| 9,752,182 B2 | 9/2017 | Collier et al. |
| 9,789,483 B2 | 10/2017 | Khattak et al. |
| 9,890,415 B2 | 2/2018 | Stehr et al. |
| 10,040,069 B2 | 8/2018 | Moore et al. |
| 10,052,629 B2 | 8/2018 | Andreyev et al. |
| 10,112,196 B2 | 10/2018 | Andreyev et al. |
| 10,112,197 B2 | 10/2018 | Andreyev et al. |
| 10,124,334 B2 | 11/2018 | Andreyev et al. |
| 10,146,909 B2 | 12/2018 | Dimov et al. |
| 10,173,182 B2 | 1/2019 | Tachibana et al. |
| 10,195,610 B2 | 2/2019 | Tang et al. |
| 10,233,483 B2 | 3/2019 | Talebpour et al. |
| 10,603,664 B2 | 3/2020 | Khattak |
| 10,987,674 B2 | 4/2021 | Andreyev et al. |
| 11,080,848 B2 | 8/2021 | Dimov et al. |
| 11,162,130 B2 | 11/2021 | Andreyev et al. |
| 11,167,285 B2 | 11/2021 | Andreyev et al. |
| 11,168,354 B2 | 11/2021 | Andreyev et al. |
| 11,273,443 B2 | 3/2022 | Andreyev et al. |
| 11,352,675 B2 | 6/2022 | Ciopyk et al. |
| 2003/0027203 A1 | 2/2003 | Fields |
| 2003/0027244 A1 | 2/2003 | Colston et al. |
| 2004/0018502 A1 | 1/2004 | Makino et al. |
| 2004/0110141 A1 | 6/2004 | Pusey et al. |
| 2004/0209331 A1 | 10/2004 | Ririe |
| 2005/0059030 A1 | 3/2005 | Bao et al. |
| 2005/0100946 A1 | 5/2005 | Lipshutz et al. |
| 2005/0142036 A1 | 6/2005 | Kim et al. |
| 2005/0194316 A1 | 9/2005 | Pourahmadi et al. |
| 2005/0227275 A1 | 10/2005 | Jung et al. |
| 2006/0127924 A1 | 6/2006 | Hellyer et al. |
| 2006/0160205 A1 | 7/2006 | Blackburn et al. |
| 2006/0177841 A1 | 8/2006 | Wangh et al. |
| 2006/0210998 A1 | 9/2006 | Kettlitz et al. |
| 2006/0258012 A1 | 11/2006 | Yang et al. |
| 2007/0026391 A1 | 2/2007 | Stoughton et al. |
| 2007/0036691 A1 | 2/2007 | Lin et al. |
| 2007/0042427 A1 | 2/2007 | Gerdes et al. |
| 2007/0154922 A1 | 7/2007 | Collier et al. |
| 2007/0277251 A1 | 11/2007 | Wartiovaara et al. |
| 2007/0292941 A1 | 12/2007 | Handique et al. |
| 2008/0038737 A1 | 2/2008 | Smith et al. |
| 2008/0050735 A1 | 2/2008 | Pushnova |
| 2008/0057572 A1 | 3/2008 | Petersen et al. |
| 2008/0113391 A1 | 5/2008 | Gibbons et al. |
| 2008/0153078 A1 | 6/2008 | Braman et al. |
| 2008/0280285 A1 | 11/2008 | Chen et al. |

(56) References Cited

U.S. PATENT DOCUMENTS

| | | |
|---|---|---|
| 2009/0035780 A1 | 2/2009 | McCarthy et al. |
| 2009/0075269 A1 | 3/2009 | Caplin |
| 2009/0130745 A1 | 5/2009 | Williams et al. |
| 2009/0186344 A1 | 7/2009 | Farinas |
| 2009/0215072 A1 | 8/2009 | McDevitt et al. |
| 2009/0325276 A1 | 12/2009 | Battrell et al. |
| 2010/0003683 A1 | 1/2010 | Sarofim et al. |
| 2010/0025242 A1 | 2/2010 | Pamula |
| 2010/0035349 A1 | 2/2010 | Bau et al. |
| 2010/0075302 A1 | 3/2010 | Perlin et al. |
| 2010/0173393 A1 | 7/2010 | Handique et al. |
| 2010/0210038 A1 | 8/2010 | Blatt et al. |
| 2010/0291536 A1 | 11/2010 | Viljoen et al. |
| 2010/0291588 A1 | 11/2010 | McDevitt et al. |
| 2010/0297640 A1 | 11/2010 | Kumar et al. |
| 2011/0020876 A1 | 1/2011 | Wilding et al. |
| 2011/0039303 A1 | 2/2011 | Jovanovich et al. |
| 2011/0160090 A1 | 6/2011 | Cary |
| 2011/0203688 A1 | 8/2011 | Reed et al. |
| 2011/0253224 A1 | 10/2011 | Linder et al. |
| 2011/0275055 A1 | 11/2011 | Conner |
| 2011/0308313 A1 | 12/2011 | Azimi et al. |
| 2011/0312666 A1 | 12/2011 | Azimi et al. |
| 2011/0312787 A1 | 12/2011 | Silverbrook et al. |
| 2011/0312841 A1 | 12/2011 | Silverbrook et al. |
| 2012/0021454 A1 | 1/2012 | Bikker et al. |
| 2012/0064534 A1 | 3/2012 | Pipper et al. |
| 2012/0088294 A1 | 4/2012 | Sun et al. |
| 2012/0135511 A1 | 5/2012 | Battrell et al. |
| 2012/0141337 A1 | 6/2012 | Maltezos et al. |
| 2012/0264114 A1 | 10/2012 | Wacogne et al. |
| 2012/0282681 A1 | 11/2012 | Teixeira et al. |
| 2012/0282684 A1 | 11/2012 | Fritchie et al. |
| 2012/0288897 A1 | 11/2012 | Ching et al. |
| 2013/0040296 A1 | 2/2013 | Tulp et al. |
| 2013/0053255 A1 | 2/2013 | Vangbo et al. |
| 2013/0078736 A1 | 3/2013 | Grover et al. |
| 2013/0115712 A1 | 5/2013 | Yu et al. |
| 2013/0118900 A1 | 5/2013 | Reimitz et al. |
| 2013/0217026 A1 | 8/2013 | Egan et al. |
| 2013/0224729 A1 | 8/2013 | Church et al. |
| 2013/0295570 A1 | 11/2013 | Wangh et al. |
| 2014/0045191 A1 | 2/2014 | DeJohn et al. |
| 2014/0073013 A1 | 3/2014 | Gorman et al. |
| 2014/0087359 A1 | 3/2014 | Njoroge et al. |
| 2014/0274770 A1 | 9/2014 | Pack |
| 2014/0329301 A1 | 11/2014 | Handique |
| 2014/0342356 A1 | 11/2014 | Stender et al. |
| 2015/0240298 A1 | 8/2015 | Piepenburg et al. |
| 2015/0258273 A1 | 9/2015 | Payne et al. |
| 2015/0290639 A1 | 10/2015 | Evtodienko |
| 2015/0322483 A1 | 11/2015 | Nakamura et al. |
| 2015/0346097 A1 | 12/2015 | Battrell et al. |
| 2016/0008811 A1 | 1/2016 | Laser et al. |
| 2016/0077015 A1 | 3/2016 | Holmes et al. |
| 2016/0186240 A1 | 6/2016 | Andreyev et al. |
| 2016/0222442 A1 | 8/2016 | Cary |
| 2016/0251702 A1 | 9/2016 | Chattopadhyay et al. |
| 2016/0256870 A1 | 9/2016 | Ismagilov et al. |
| 2016/0281149 A1 | 9/2016 | Hassibi et al. |
| 2016/0289669 A1 | 10/2016 | Fan et al. |
| 2016/0310948 A1 | 10/2016 | Nowakowski et al. |
| 2017/0021356 A1 | 1/2017 | Dority et al. |
| 2017/0058324 A1 | 3/2017 | Balog et al. |
| 2017/0121756 A1 | 5/2017 | Abate et al. |
| 2017/0152510 A1 | 6/2017 | Lorenz |
| 2017/0173585 A1 | 6/2017 | Mahony et al. |
| 2017/0247745 A1 | 8/2017 | Schultz et al. |
| 2017/0260570 A1 | 9/2017 | Balashov et al. |
| 2017/0304829 A1 | 10/2017 | Andreyev et al. |
| 2018/0135108 A1 | 5/2018 | Etchebarne |
| 2018/0135110 A1 | 5/2018 | Saxena et al. |
| 2018/0304260 A1 | 10/2018 | Thomas et al. |
| 2018/0355410 A1 | 12/2018 | Lee et al. |
| 2019/0022643 A1 | 1/2019 | Andreyev et al. |
| 2019/0030532 A1 | 1/2019 | Andreyev et al. |
| 2019/0032104 A1 | 1/2019 | Lowery et al. |
| 2019/0040451 A1 | 2/2019 | Mahony et al. |
| 2019/0060895 A1 | 2/2019 | Myers, III et al. |
| 2019/0083975 A1 | 3/2019 | Mitra et al. |
| 2019/0094114 A1 | 3/2019 | Myers, III et al. |
| 2019/0136226 A1 | 5/2019 | Swenson et al. |
| 2019/0151844 A1 | 5/2019 | Andreyev et al. |
| 2019/0169677 A1 | 6/2019 | Andreyev et al. |
| 2019/0193077 A1 | 6/2019 | Andreyev et al. |
| 2019/0232283 A1 | 8/2019 | Andreyev et al. |
| 2019/0232293 A1 | 8/2019 | Tang et al. |
| 2019/0262827 A1 | 8/2019 | Lalonde et al. |
| 2020/0086324 A1 | 3/2020 | Swenson et al. |
| 2020/0346213 A1 | 11/2020 | Andreyev et al. |
| 2020/0406256 A1 | 12/2020 | Andreyev et al. |
| 2020/0406257 A1 | 12/2020 | Andreyev et al. |
| 2020/0408750 A1 | 12/2020 | Khattak |
| 2021/0039097 A1 | 2/2021 | Andreyev et al. |
| 2021/0071236 A1 | 3/2021 | Andreyev et al. |
| 2021/0207194 A1 | 7/2021 | Ciopyk et al. |
| 2021/0299669 A1 | 9/2021 | Swenson et al. |
| 2022/0055032 A1 | 2/2022 | Andreyev et al. |
| 2022/0186208 A1 | 6/2022 | Swenson et al. |
| 2022/0203365 A1 | 6/2022 | Abraham et al. |
| 2022/0325363 A1 | 10/2022 | Broughton et al. |

FOREIGN PATENT DOCUMENTS

| | | |
|---|---|---|
| EP | 2682480 | 1/2014 |
| WO | WO-0118017 A1 | 3/2001 |
| WO | WO-2001/049416 | 7/2001 |
| WO | WO-2007/061943 | 5/2007 |
| WO | WO-2008/082432 | 7/2008 |
| WO | WO-2008/149111 | 12/2008 |
| WO | WO-2012/009813 | 1/2012 |
| WO | WO-2014/144548 | 9/2014 |
| WO | WO-2015/035260 | 3/2015 |
| WO | WO-2015/164770 | 10/2015 |
| WO | WO-2016/106391 | 6/2016 |
| WO | WO-2016086305 A1 | 6/2016 |
| WO | WO-2016109691 A1 | 7/2016 |
| WO | WO-2016/203019 | 12/2016 |
| WO | WO-2017/090043 | 6/2017 |
| WO | WO-2017134627 A1 | 8/2017 |
| WO | WO-2017/151195 | 9/2017 |
| WO | WO-2017/160840 | 9/2017 |
| WO | WO-2017185067 A1 | 10/2017 |
| WO | WO-2018005710 A1 | 1/2018 |
| WO | WO-2018005870 A1 | 1/2018 |
| WO | WO-2018087205 A1 | 5/2018 |
| WO | WO-2018/119443 | 6/2018 |
| WO | WO-2020/051156 | 3/2020 |
| WO | WO-2020/180858 | 9/2020 |
| WO | WO-2020/214557 | 10/2020 |
| WO | WO-2020/223257 | 11/2020 |
| WO | WO-2021138544 A1 | 7/2021 |
| WO | WO-2021195150 A1 | 9/2021 |

OTHER PUBLICATIONS

Allan-Blitz, L. et al. "A Cost Analysis of Gyrase A Testing and Targeted Ciprofloxacin Therapy Versus Recommended 2-Drug Therapy for Neisseria gonorrhoeae Infection," Sexually Transmitted Diseases, vol. 45, No. 2, pp. 86-91. (Feb. 2018).

Allan-Blitz, L. et al. "Ciprofloxacin May be Efficacious in Treating Wild-Type Gyrase A Genotype Neisseria gonorrhoeae Infections," Sexually Transmitted Diseases, vol. 45, Issue 4, p. e18 (Apr. 2018).

Allan-Blitz, L. et al. "Implementation of a Rapid Genotypic Assay to Promote Targeted Ciprofloxacin Therapy of Neisseria gonorrhoeae in a Large Health System," Clinical Infectious Diseases, 64(9): 1268-70 (May 2017).

Allan-Blitz, L. et al. "Wild-Type Gyrase A Genotype of Neisseria gonorrhoeae Predicts In Vitro Susceptibility to Ciprofloxacin: A Systematic Review of the Literature and Meta-Analysis," Sex Transm Dis. 44(5): 261-265 (May 2017).

(56) References Cited

OTHER PUBLICATIONS

Alm, R. et al. "Characterization of the Novel DNA Gyrase Inhibitor AZD0914: Low Resistance Potential and Lack of Cross-Resistance in Neisseria gonorrhoeae," Antimicrobial Agents and Chemotherapy, vol. 59, No. 3, pp. 1478-1486 (Mar. 2015).
Benett, William et al. "Handheld advanced nucleic acid analyzer," Event: Environmental and Industrial Sensing, Boston, MA, Proceedings of SPIE, vol. 4200 (2000), pp. 55-63.
Bolan, G. et al. "The Emerging Threat of Untreatable Gonococcal Infection," The New England Journal of Medicine; 366; 6, pp. 485-487 (Feb. 9, 2012).
Brunklaus, S. et al., Fast nucleic acid amplification for integration in point-of-care applications, Electrophoresis, 2012, vol. 33, pp. 3222-3228.
Buckley, C. et al. "Real-time PCR detection of Neisseria gonorrhoeae susceptibility to penicillin," Journal of Antimicrobial Chemotherapy, 71: 3090-3095 (Jul. 25, 2016).
Buckley, C. et al. "Use of whole genome sequencing to investigate an increase in Neisseria gonorrhoeae infection among women in urban areas of Australia," Scientific Reports, 8:1503, 7 pages (Jan. 24, 2018).
Buono, S. et al. "Stemming the tide of drug-resistant Neisseria gonorrhoeae: the need for an individualized approach to treatment," J. Antimicrobial Chemotherapy, vol. 70, pp. 374-381 (Oct. 19, 2014).
Choi, Gihoon et al., "A field-deployable mobile molecular diagnostic system for malaria at the point of need," Lab on a Chip, Royal Society of Chemistry, 2016, 16, 4341-4349.
Dillard, J. "Genetic Manipulation of Neisseria gonorrhoeae," Curr Protoc Microbiol, Author Manuscript, 34 pgs (Nov. 2011).
Dize, L. et al. "Comparison of self-obtained penile-meatal swabs to urine for the detection of C. trachomatis, N. gonorrhoeae and T. vaginalis," Sex Transm Infect. 89(4): 305-307 (Jun. 2013).
Dize, L. et al. "Performance of self-collected penile-meatal swabs compared to clinician-collected urethral swabs for the detection of Chlamydia trachomatis, Neisseria gonorrhoeae, Trichomonas vaginalis and Mycoplasma genitalium by Nucleic Acid Amplification Assays," Diagn Microbiol Infect Dis; 86(2): 131-135 (Oct. 2016).
Dona, V. et al. "Multiplex Real-Time PCR Assay with High-Resolution Melting Analysis for Characterization of Antimicrobial Resistance in Neisseria gonorrhoeae," Journal of Clinical Microbiology, vol. 54, No. 8, pp. 2074-2081 (Aug. 2016).
Dutta, Gorachand et al. "Microfluidic Devices for Label-Free DNA Detection," Chemosensors, Sep. 25, 2018, 6, 43 www.mdpi.com/journal/chemosensors, 20 pgs.
Edouard et al., "Cost-Effective Pooling of DNA from Nasopharyngeal Swab Samples for Large-Scale Detection of Bacteria by Real-Time PCR," Journal of Clinical Microbiology, vol. 53, No. 3, Mar. 2015, pp. 1002-1004.
Elnifro, Elfath M. et al. "Multiplex PCR: Optimization and Application in Diagnostic Virology," Clinical Microbiology Reviews, vol. 13, No. 4, Oct. 2000, pp. 559-570.
Extended European Search Report for European Application No. 17821297.3, dated Dec. 17, 2019, 21 pages.
Fifer et al. "Sustained transmission of high-level azithromycin-resistant Neisseria gonorrhoeae in England: an observational study," Lancet Infect Dis 2018; 18: 573-81 (Mar. 6, 2018).
Gehring et al. "A High-Throughput, Precipitating Colorimetric Sandwich ELISA Microarray for Shiga Toxins," J. Toxins, vol. 6, p. 1855-72, Jun. 11, 2014.
Global Antibiotic Research and Development Partnership. "Gonorrhea Expert Meeting," Drugs for Neglected Disease Initiative (Jun. 2016), 18 pages.
Gose, S. et al. "Neisseria gonorrhoeae and extended-spectrum cephalosporins in California: surveillance and molecular detection of mosaic penA," BMC Infectious Diseases, 13:570, 9 pages (2013).
Grad, Y. et al. "Genomic Epidemiology of Gonococcal Resistance to Extended-Spectrum Cephalosporins, Macrolides, and Fluoroquinolones in the United States, 2000-2013," Journal of Infectious Diseases, 214: 1579-87 (2016).
Grad, Y. et al. "Genomic epidemiology of Neisseria gonorrhoeae with reduced susceptibility to cefixime in the USA: a retrospective observational study," Lancet Infect Dis 14: 220-26 (Jan. 22, 2014).
Harding-Esch et al. "A 30-min nucleic acid amplification point-of-care test for genital *Chlamidya trachomatis* infection in women: a prospective, multi-center study of diagnostic accuracy." EBioMedicine 2018; 28:120-27.
Hassibi et al. "An array-based melt curve analysis method for the identification and classification of closely related pathogen strains." Biology Methods and Protocols 2018; pp. 1-12.
Hemarajata, P. et al. "Performance and Verification of a Real-Time PCR Assay Targeting the gyrA Gene for Prediction of Ciprofloxacin Resistance in Neisseria ghonrrhoeae," J. Clinical Microbiology vol. 54, No. 3: 805-808; (Jan. 6, 2016).
Herbst De Cortina, S. et al. "A Systematic Review of Point of Care Testing for Chlamydia trachomatis, Neisseria gonorrhoeae, and Trichomonas vaginalis," Infectious Diseases in Obstetrics and Gynecology, vol. 2016, 17 pages (Mar. 7, 2016).
Huang et al., "Efficient SNP Discovery by Combining Microarray and Lab-on-a-Chip Data for Animal Breeding and Selection," Microarrays, Nov. 16, 2015, vol. 4, No. 4, pp. 570-595, entire document.
Huppert, J. et al. "What's the Point? How Point-of-Care STI Tests can Impact Infected Patients," National Institutes of Health, vol. 9(1): pp. 36-46 (Mar. 1, 2010).
Hwang et al., "Black Printed Circuit Board-based Micro-Polymerase Chain Reaction Chip Structure for Fluorescence Detection Test", International Journal of Control and Automation (2015); vol. 8, No. 10: pp. 15-24 (10 pages).
Interbiotech, "Enzymatic substrates for ImmunoAssays," [retreived from the Internet Nov. 18, 2017: <http://www.interchim.fr/ft/B/BA357a.pdf>], 10 pages.
International Search Report and Written Opinion for International Application No. PCT/US20/67642, dated May 3, 2021, 17 pages.
International Search Report and Written Opinion for International Application No. PCT/US21/23781, dated Aug. 25, 2021, 16 pages.
International Search Report and Written Opinion for PCT/US2019/049385, dated Nov. 15, 2019, 12 pages.
International Search Report and Written Opinion for PCT/US2020/030307, dated Jul. 23, 2020, 24 pages.
Kerremans, J. et al. "Rapid identification and antimicrobial susceptibility testing reduce antibiotic use and accelerate pathogen-directed antibiotic use," J. Antimicrobial Chemotherapy, vol. 61, pp. 428-435 (Dec. 21, 2007).
Kim, Jungkyu et al. "Automated microfluidic DNA/RNA extraction with both disposable and reusable components," Journal of Micromechanics and Microengineering, Vo. 22, No. 1, Dec. 20, 2011, 21 pages.
Kim, Yong Tae et al. "Integrated Microdevice of reverse transcription-polymerase chain reaction with colorimetric immunochromatographic detection for rapid gene expression analysis of influenza A H1N1 virus," Biosensors and Bioelectronics, Elsevier Science Ltd UK, Amsterdam, NL V. 33 No. 1, pp. 88-94, Dec. 14, 2011.
Kim, Young Ho et al., "Performance evaluation of thermal cyclers for PCR in a rapid cycling condition," BioTechniques, www.biotechniques.com, vol. 44, No. 4, 2008, pp. 495-505.
Kopp et al., "Chemical Amplification: Continuous-Flow PCR on a Chip", Science (1998); 280 (5366): 1046-1048.
Lee et al. "A polymer lab-on-a-chip for reverse transcription (RT)-PCR based point-of-care clinical diagnostics," The Royal Society of Chemistry, vol. 8, pp. 2121-2127, Oct. 31, 2008.
Lee et al. "Single-channel multiplexing without melting curve analysis in real-time PCR," Scientific Reports, Dec. 11, 2014, vol. 4, Art. No. 7439, pp. 1-6, entire document.
Lindberg, R. et al. "Neisseria gonorrhoeae Isolates with Reduced Susceptibility to Cefixime and Ceftriaxone: Association with Genetic Polymorphisms in penA, mtrR, porB1b, and ponA," Antimicrobial Agents and Chemotherapy, vol. 51, No. 6, pp. 2117-2122 (Jun. 2007).

(56) References Cited

OTHER PUBLICATIONS

Magooa, M. et al. "Determination of Neisseria gonorrhoeae susceptibility to ciprofloxacin in clinical specimens from men using a real-time PCR assay," International Journal of Antimicrobial Agents, 42, 63-67 (2013).

Melendez, J. et al. "Antimicrobial Susceptibility of Neisseria gonorrhoeae Isolates in Baltimore, Maryland, 2016: The Importance of Sentinel Surveillance in the Era of Multi-Drug-Resistant Gonorrhea," Antibiotics, 7, 77 (Aug. 17, 2018), pp. 1-7.

Mohammed et al., Modeling of Serpentine Continuous Flow Polymerase Chain Reaction Microfluidics, IJEST, vol. 4, No. 3, pp. 1183-1189, Mar. 2012.

Morris et al. "Performance of a single-use, rapid, point-of-care PCR device for the detection of Neisseria gonorrhoeae, Chlamydia trachomatis, and Trichomonas vaginalis: a cross-sectional study," Lancet Infectious Diseases 2020, https://doi.org/10.1016/; S1473-3099(20)30734-9; Published online Nov. 23, 2020, 9 pages.

Mortimer, T. et al. "Applications of genomics to slow the spread of multidrug-resistant Neisseria gonorrhoeae," Annals of the New York Academy of Sciences, Special Issue: Antimicrobial Therapeutics Reviews; 1-17 (2018).

Moschou D., et al., 'All-plastic, low-power, disposable, continuous-flow PCR chip with integrated microheaters for rapid DNA amplification', Sensors and Actuators B: Chemical, vol. 199, Aug. 1, 2014, pp. 470-478.

Ng, L. et al. "Mutation in 23S rRNA Associated with Macrolide Resistance in Neisseria gonorrhoeae," Antimicrobial Agents and Chemotherapy, vol. 46, No. 9, pp. 3020-3025 (Sep. 2002).

Office Action for U.S. Appl. No. 17/139,451, dated May 4, 2021, 7 pages.

Papp, J. et al. "Azithromycin Resistance and Decreased Ceftriaxone Susceptibility in Neisseria gonorrhoeae, Hawaii, USA," Emerging Infectious Diseases, vol. 23, No. 5, pp. 830-832 (May 2017).

Partial Supplementary Search Report for European Application No. 18876258.7, completed Sep. 21, 2021. 21 pages.

Peterson, S. et al. "Molecular Assay for Detection of Genetic Markers Associated with Decreased Susceptibility to Cephalosporins in Neisseria gonorrhoeae," Journal of Clinical Microbiology, vol. 53, No. 7, pp. 2042-2048 (Jul. 2015).

Petralia, Salvatore et al. "PCR Technologies for Point of Care Testing: Progress and Perspectives," ACS Sensors, 2017, 2 (7), pp. 876-891, Jul. 6, 2017.

Pond, M. et al. "Accurate detection of Neisseria gonorrhoeae ciprofloxacin susceptibility directly from genital and extragenital clinical samples: towards genotype-guided antimicrobial therapy," Journal of Antimicrobial Chemotherapy, 71: 897-902 (Jan. 26, 2016).

Poritz, Mark A. et al., "FilmArray, an Automated Nested Multiplex PCR System for Multi-Pathogen Detection: Development and Application to Respiratory Tract Infection," PLoS ONE www.plosone.org, Oct. 2011, vol. 6, Issue 10 (14 pgs.).

Primiceri, Elisabetta et al. "Key Enabling Technologies for Point-of-Care Diagnostics," MDPI, Sensors 18, 3607; doi:10.3390/s18113607, www.mdpi.com/journal/sensors, 2018, pp. 1-34.

Public Health England. "Update on investigation of UK case of Neisseria gonorrhoeae with high-level resistance to azithromycin and resistance to ceftriaxone acquired abroad," Health Protection Report, vol. 12, No. 14 (Apr. 20, 2018), 4 pages.

Richards, James et al. "Miniaturized detection system for handheld PCR assays," Event: Environmental and Industrial Sensing, Boston, MA, Proceedings of SPIE, vol. 4200 (2000), pp. 64-73.

Roskos, Kristina et al. "Simple System for Isothermal DNA Amplification Coupled to Lateral Flow Detection," PLoS ONE 8(7): e69355. https://doi.org/10.1371/journal.pone.0069355; Jul. 26, 2013, 11 pages.

Rybicki et al., "Standard PCR Protocol," Feb. 1, 2001, 4 pages.

Shafagati, et al., The Use of NanoTrap Particles as a Sample Enrichment Method to Enhance the Detection of Rift Valley Fever Virus. PLOS Neglected Tropical Diseases, Jul. 4, 2013; 7(7): e2296.

Siedner, M. et al. "Real-Time PCR Assay for Detection of Quinolone-Resistant Neisseria gonorrhoeae in Urine Samples," Journal of Clinical Microbiology, vol. 45, No. 4, pp. 1250-1254 (Apr. 2007).

Tanriverdi et al. A rapid and automated sample-to-result HIV load test for near-patient application. J Infect Dis., 201 Suppl 1:S52-S58, 2010.

Terhes et al. "Comparison of a Rapid Molecular Method, the BD GeneOhm Cdiff Assay, to the Most Frequently Used Laboratory Tests for Detection of Toxin-Producing Clostridium difficile in Diarrheal Feces," Journal of Clinical Microbiology, vol. 47, No. 11, Nov. 2009, pp. 3478-3481.

Thiha et al. A Colorimetric Enzyme-Linked Immunoabsorbent Assay (ELISA) Detection Platform for a Point-Of-Care Dengue Detection System on a Lab-on-Compact-Disc; Sensors ISSN 1424-8220, May 18, 2015.

Trembizki, E. et al. "Further evidence to support the individualised treatment of gonorrhoea with ciprofloxacin," Lancet Infect. Dis. 16, 1005-1006 (Sep. 2016).

Tsaloglou, Maria-Nefeli et al. "Handheld isothermal amplification and electrochemical detection of DNA in resource-limited settings," Analytical Biochemistry 543, 2018, pp. 116-121.

Tuite, A. et al. "Impact of Rapid Susceptibility Testing and Antibiotic Selection Strategy on the Emergence and Spread of Antibiotic Resistance in Gonorrhea," J. Infectious Diseases, 216:1141-9 (Nov. 1, 2017).

Ullerich, Lars et al. "Ultra-fast PCR technologies for point-of-care testing," De Gruyter, J. Lab Med 2017; 41(5), pp. 239-244.

Unemo, M. et al. "High In Vitro Susceptibility to the Novel Spiropyrimidinetrione ETX0914 (AZD0914) among 873 Contemporary Clinical Neisseria gonorrhoeae Isolates from 21 European Countries from 2012 to 2014," Antimicrobial Agents and Chemotherapy, vol. 59, No. 9, pp. 5220-5225 (Sep. 2015).

Vernel-Pauillac, F. et al. "Quinolone Resistance in Neisseria gonorrhoeae: Rapid Genotyping of Quinolone Resistance-Determining Regions in gyrA and parC Genes by Melting Curve Analysis Predicts Susceptibility," Antimicrobial Agents and Chemotherapy, vol. 53, No. 3, pp. 1264-1267 (Mar. 2009).

Wheeler, E.K., 'Under-three minute PCR: Probing the limits of fast amplification', published Jul. 27, 2011 by the Royal Society of Chemistry: Analyst 2011 vol. 136 pp. 3707-3712.

White, Adam K. et al. High-throughput microfluidic single-cell RT-qPCR, PNAS, Aug. 23, 2011, vol. 108, No. 34, pp. 13999-14004.

White, Adam K. et al. "High-throughput microfluidic single-cell RT-qPCR, Supporting Information White et al. 10.1073/pnas.1019446108" PNAS, Aug. 23, 2011, vol. 108, No. 34, pp. 1-9.

Wong, L.K. et al. "Real-Time PCR Targeting the penA Mosaic XXXIV Type for Prediction of Extended-Spectrum-Cephalosporin Susceptibility in Clinical Neisseria gonorrhoeae Isolates," Am. Society for Microbiology, Antimicrobial Agents and Chemotherapy, vol. 61, Issue 11 (Nov. 2017), pp. 1-6.

Wu, Jinbo et al. "Extraction, amplification and detection of DNA in microfluidic chip-based assays," © Springer-Verlag Wein 2013, pp. 1611-1631.

Yotoriyama, T. et al. "Miniaturized PCR Device for Rapid Detection of Infectious Agents," 14th International Conference on Miniaturized Systems for Chemistry and Life Sciences, Oct. 3-17, 2010, pp. 142-144.

Zhang, Chunsun et al. "PCR microfluidic devices for DNA amplification," Biotechnology Advances 24, (2006) pp. 243-284.

Zhang, Chunsun et al. "Survey and Summary—Miniaturized PCR chips for nucleic acid amplification and analysis: latest advances and future trends," Nucleic Acids Research, 2007, vol. 35, No. 13, pp. 4223-4237.

Zhao, L. et al. "TaqMan Real-Time Quantitative PCR Assay for Detection of Fluoroquinolone-Resistant Neisseria gonorrhoeae," Curr Microbiol 65: 692-695 (Sep. 2, 2012).

Zumla, Alimuddin et al., "Emerging respiratory tract infections 4—Rapid point of care diagnostic tests for viral and bacterial respiratory tract infections—needs, advances, and future prospects," Lancet Infect. Dis. www.thelancet/infection, vol. 14, Nov. 2014, pp. 1123-1135.

(56) References Cited

OTHER PUBLICATIONS

International Search Report and Written Opinion for International Application No. PCT/US2020/067642, dated Jul. 8, 2021, 18 pages.
International Search Report and Written Opinion for International Application No. PCT/US2021/023781, dated Sep. 30, 2021, 16 pages.
Oleastro M., et al., : "Real-Time PCR Assay for Rapid and Accurate Detection of Point Mutations Conferring Resistance to Clarithromycin in Helicobacter pylori", Journal of Clinical Microbiology, vol. 41, No. 1, Jan. 2003 (Jan. 2003), pp. 397-402, XP055274907, US ISSN: 0095-1137, DOI: 10.1128/JCM.41.1.397-402.2003.
Rajendran, et al., Smartphone detection of antibiotic resistance using convective PCR and a lateral flow assay, Sensors and Actuators B: Chemical, Nov. 2019, 10 pages.

Cipro-Sensitive

Cipro-Resistant

SEQUENCE LISTING

```
<160> NUMBER OF SEQ ID NOS: 23

<210> SEQ ID NO 1
<211> LENGTH: 1273
<212> TYPE: PRT
<213> ORGANISM: Betacoronavirus Severe acute respiratory syndrome
      coronavirus 2

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60
```

-continued

```
Phe His Ala Ile His Val Ser Gly Thr Asn Gly Thr Lys Arg Phe Asp
 65                  70                  75                  80

Asn Pro Val Leu Pro Phe Asn Asp Gly Val Tyr Phe Ala Ser Thr Glu
                 85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480
```

```
Asn Gly Val Glu Gly Phe Asn Cys Tyr Phe Pro Leu Gln Ser Tyr Gly
            485                 490                 495
Phe Gln Pro Thr Asn Gly Val Gly Tyr Gln Pro Tyr Arg Val Val Val
        500                 505                 510
Leu Ser Phe Glu Leu Leu His Ala Pro Ala Thr Val Cys Gly Pro Lys
        515                 520                 525
Lys Ser Thr Asn Leu Val Lys Asn Lys Cys Val Asn Phe Asn Phe Asn
        530                 535                 540
Gly Leu Thr Gly Thr Gly Val Leu Thr Glu Ser Asn Lys Lys Phe Leu
545                 550                 555                 560
Pro Phe Gln Gln Phe Gly Arg Asp Ile Ala Asp Thr Thr Asp Ala Val
            565                 570                 575
Arg Asp Pro Gln Thr Leu Glu Ile Leu Asp Ile Thr Pro Cys Ser Phe
            580                 585                 590
Gly Gly Val Ser Val Ile Thr Pro Gly Thr Asn Thr Ser Asn Gln Val
            595                 600                 605
Ala Val Leu Tyr Gln Asp Val Asn Cys Thr Glu Val Pro Val Ala Ile
        610                 615                 620
His Ala Asp Gln Leu Thr Pro Thr Trp Arg Val Tyr Ser Thr Gly Ser
625                 630                 635                 640
Asn Val Phe Gln Thr Arg Ala Gly Cys Leu Ile Gly Ala Glu His Val
            645                 650                 655
Asn Asn Ser Tyr Glu Cys Asp Ile Pro Ile Gly Ala Gly Ile Cys Ala
            660                 665                 670
Ser Tyr Gln Thr Gln Thr Asn Ser Pro Arg Arg Ala Arg Ser Val Ala
        675                 680                 685
Ser Gln Ser Ile Ile Ala Tyr Thr Met Ser Leu Gly Ala Glu Asn Ser
        690                 695                 700
Val Ala Tyr Ser Asn Asn Ser Ile Ala Ile Pro Thr Asn Phe Thr Ile
705                 710                 715                 720
Ser Val Thr Thr Glu Ile Leu Pro Val Ser Met Thr Lys Thr Ser Val
            725                 730                 735
Asp Cys Thr Met Tyr Ile Cys Gly Asp Ser Thr Glu Cys Ser Asn Leu
            740                 745                 750
Leu Leu Gln Tyr Gly Ser Phe Cys Thr Gln Leu Asn Arg Ala Leu Thr
        755                 760                 765
Gly Ile Ala Val Glu Gln Asp Lys Asn Thr Gln Glu Val Phe Ala Gln
        770                 775                 780
Val Lys Gln Ile Tyr Lys Thr Pro Pro Ile Lys Asp Phe Gly Gly Phe
785                 790                 795                 800
Asn Phe Ser Gln Ile Leu Pro Asp Pro Ser Lys Pro Ser Lys Arg Ser
            805                 810                 815
Phe Ile Glu Asp Leu Leu Phe Asn Lys Val Thr Leu Ala Asp Ala Gly
            820                 825                 830
Phe Ile Lys Gln Tyr Gly Asp Cys Leu Gly Asp Ile Ala Ala Arg Asp
        835                 840                 845
Leu Ile Cys Ala Gln Lys Phe Asn Gly Leu Thr Val Leu Pro Pro Leu
        850                 855                 860
Leu Thr Asp Glu Met Ile Ala Gln Tyr Thr Ser Ala Leu Leu Ala Gly
865                 870                 875                 880
Thr Ile Thr Ser Gly Trp Thr Phe Gly Ala Gly Ala Ala Leu Gln Ile
            885                 890                 895
Pro Phe Ala Met Gln Met Ala Tyr Arg Phe Asn Gly Ile Gly Val Thr
```

```
                900             905             910
Gln Asn Val Leu Tyr Glu Asn Gln Lys Leu Ile Ala Asn Gln Phe Asn
            915             920             925
Ser Ala Ile Gly Lys Ile Gln Asp Ser Leu Ser Ser Thr Ala Ser Ala
            930             935             940
Leu Gly Lys Leu Gln Asp Val Val Asn Gln Asn Ala Gln Ala Leu Asn
945             950             955             960
Thr Leu Val Lys Gln Leu Ser Ser Asn Phe Gly Ala Ile Ser Ser Val
            965             970             975
Leu Asn Asp Ile Leu Ser Arg Leu Asp Lys Val Glu Ala Glu Val Gln
            980             985             990
Ile Asp Arg Leu Ile Thr Gly Arg Leu Gln Ser Leu Gln Thr Tyr Val
            995             1000            1005
Thr Gln Gln Leu Ile Arg Ala Ala Glu Ile Arg Ala Ser Ala Asn
            1010            1015            1020
Leu Ala Ala Thr Lys Met Ser Glu Cys Val Leu Gly Gln Ser Lys
            1025            1030            1035
Arg Val Asp Phe Cys Gly Lys Gly Tyr His Leu Met Ser Phe Pro
            1040            1045            1050
Gln Ser Ala Pro His Gly Val Val Phe Leu His Val Thr Tyr Val
            1055            1060            1065
Pro Ala Gln Glu Lys Asn Phe Thr Thr Ala Pro Ala Ile Cys His
            1070            1075            1080
Asp Gly Lys Ala His Phe Pro Arg Glu Gly Val Phe Val Ser Asn
            1085            1090            1095
Gly Thr His Trp Phe Val Thr Gln Arg Asn Phe Tyr Glu Pro Gln
            1100            1105            1110
Ile Ile Thr Thr Asp Asn Thr Phe Val Ser Gly Asn Cys Asp Val
            1115            1120            1125
Val Ile Gly Ile Val Asn Asn Thr Val Tyr Asp Pro Leu Gln Pro
            1130            1135            1140
Glu Leu Asp Ser Phe Lys Glu Glu Leu Asp Lys Tyr Phe Lys Asn
            1145            1150            1155
His Thr Ser Pro Asp Val Asp Leu Gly Asp Ile Ser Gly Ile Asn
            1160            1165            1170
Ala Ser Val Val Asn Ile Gln Lys Glu Ile Asp Arg Leu Asn Glu
            1175            1180            1185
Val Ala Lys Asn Leu Asn Glu Ser Leu Ile Asp Leu Gln Glu Leu
            1190            1195            1200
Gly Lys Tyr Glu Gln Tyr Ile Lys Trp Pro Trp Tyr Ile Trp Leu
            1205            1210            1215
Gly Phe Ile Ala Gly Leu Ile Ala Ile Val Met Val Thr Ile Met
            1220            1225            1230
Leu Cys Cys Met Thr Ser Cys Cys Ser Cys Leu Lys Gly Cys Cys
            1235            1240            1245
Ser Cys Gly Ser Cys Cys Lys Phe Asp Glu Asp Asp Ser Glu Pro
            1250            1255            1260
Val Leu Lys Gly Val Lys Leu His Tyr Thr
            1265            1270

<210> SEQ ID NO 2
<211> LENGTH: 2751
<212> TYPE: DNA
<213> ORGANISM: Neisseria gonorrhoeae
```

<400> SEQUENCE: 2

```
atgaccgacg caaccatccg ccacgaccac aaattcgccc tcgaaaccct gcccgtcagc    60
cttgaagacg aaatgcgcaa aagctatctc gactacgcca tgagcgtcat tgtcgggcgc   120
gcgctgccgg acgttcgcga cggcctaaag ccggtgcacc ggcgcgtact gtacgcgatg   180
cacgagctga aaataactg gaatgccgcc tacaaaaaat cggcgcgcat cgtcggcgac    240
gtcatcggta ataccaccc ccacggcgat tccgcagttt acgacaccat cgtccgtatg    300
gcgcaaaatt tcgctatgcg ttatgtgctg atagacggac agggcaactt cggatcggtg   360
gacgggcttg ccgccgcagc catgcgctat accgaaatcc gcatggcgaa aatctcacat   420
gaaatgctgg cagacattga ggaagaaacc gttaatttcg cccgaactaa cgacggtagc   480
gaacacgagc cgcttgtact gccgacccgt tccccacac tgctcgtcaa cggctcgtcc    540
ggtatcgccg tcggtatggc gaccaacatc ccgccgcaca acctcaccga caccatcaac   600
gcctgtctgc gtcttttgga cgaacccaaa accgaaatcg acgaactgat cgacattatc   660
caagcccccg acttcccgac cggggcaacc atctacggct gggcggcgt gcgcgaaggc    720
tataaaacag gccgcggccg cgttgttatg cgcggtaaga cccatatcga acccataggc   780
aaaaacggcg aacgcgaacg catcgttatc gacgaaatcc cctatcaggt caacaaagcc   840
aagttggtcg agaaaatcgg cgatttggtt cgggaaaaaa cactggaagg catttccgag   900
ctccgcgacg aatccgacaa atccggtatg cgcgtcgtta tcgagctgaa acgcaacgaa   960
aatgccgaag tcgtcttaaa ccaactctac aaactgactc cgctgcaaga cagtttcggc  1020
atcaatatgg tggttttggt cgacggacaa ccgcgcctgt taaacctgaa acagattctc  1080
tccgaattcc tgcgccaccg ccgcgaagtc gttacccgac gtacgctttt ccggctgaag  1140
aaggcacgcc atgaagggca tatcgccgaa cggaaagccg tcgcactgtc caatatcgat  1200
gaaatcatca agctcatcaa agaatcgccc aacgcggccg aggccaaaga aaaactgctt  1260
gcgcgccctt gggccagcag cctcgttgaa gaaatgctga cgcgttccgg tctggatttg  1320
gaaatgatgc gtccggaagg attggtcgca acattggtc tgaaaaaaca aggttattac  1380
ctgagcgaga ttcaggcaga tgctatttta cgcatgagcc tgcgaaacct gaccggcctc  1440
gatcagaaag aaattatcga aagctacaaa aacctgatgg gtaaaatcat cgactttgtg  1500
gatatcctct ccaaacccga acgcattacc caaatcatcc gtgacgaact ggaagaaatc  1560
aaaaccaact atggcgacga acgccgcagc gaaatcaacc cgttcggcgg cgacattgcc  1620
gatgaagacc tgattccgca acgcgaaatg gtcgtgaccc tgacccacgg cggctatata  1680
aaaacccagc cgaccaccga ctatcaggct cagcgtcgcg gcgggcgcgg caaacaggcg  1740
gctgccacca aagacgaaga ctttatcgaa accctgtttg ttgccaacac gcatgactat  1800
ttgatgtgtt ttaccaacct cggcaagtgc cactggatta aggtttacaa actgcccgaa  1860
ggcggacgca cagccgcgg ccgtccgatt aacaacgtca tccagctgga agaaggcgaa   1920
aaagtcagcg cgattctggc agtacgcgag tttcccgaag accaatacgt cttcttcgcc  1980
accgcgcagg gaatggtgaa aaaagtccaa ctttccgcct ttaaaaacgt ccgcgcccaa  2040
ggcattaaag ccatcgcact caagaaggc gactacctcg tcggcgctgc gcaaacaggc   2100
ggtgcggacg acattatgtt gttctccaac ttgggcaaag ccatccgctt caacgaatac  2160
tgggaaaaat ccggcaacga cgaagcgaa gatgccgaca tcgaaaccga gatttcagac   2220
gacctcgaag acgaaaccgc cgacaacgaa aacaccctgc caagcggcaa aaacggcgtg  2280
```

```
cgtccgtccg gtcgcggcag cggcggtttg cgcggtatgc gcctgcctgc cgacggcaaa    2340
atcgtcagcc tgattacctt cgcccctgaa accgaagaaa gcggtttgca agttttaacc    2400
gccaccgcca acggatacgg aaaacgcacc ccgattgccg attacagccg caaaaacaaa    2460
ggcgggcaag gcagtattgc cattaacacc ggcgagcgca acggcgattt ggtcgccgca    2520
accttggtcg gcgaaaccga cgatttgatg ctgattacca gcggcggcgt gcttatccgt    2580
accaaagtcg aacaaatccg cgaaaccggc cgcgccgcag caggcgtgaa actgattaac    2640
ttggacgaag gcgaaacctt ggtatcgctg aacgtgttg ccgaagacga atccgaactc    2700
tccggcgctt ctgtaatttc caatgtaacc gaaccggaag ccgagaactg a             2751
```

```
<210> SEQ ID NO 3
<211> LENGTH: 108
<212> TYPE: DNA
<213> ORGANISM: Neisseria gonorrhoeae

<400> SEQUENCE: 3
cgcgcatcgt cggcgacgtc atcggtaaat accaccccca cggcgattcc gcagtttacg    60
acaccatcgt ccgtatggcg caaaatttcg ctatgcgtta tgtgctga                 108

<210> SEQ ID NO 4
<211> LENGTH: 11
<212> TYPE: DNA
<213> ORGANISM: Artificial Sequence
<220> FEATURE:
<223> OTHER INFORMATION: oligonucleotide primer

<400> SEQUENCE: 4
gcgcatcgtc g                                                         11

<210> SEQ ID NO 5
<211> LENGTH: 19
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (1)..(1)
<223> OTHER INFORMATION: Conjugated to a biotin moiety via a linker

<400> SEQUENCE: 5
tcagcacata acgcatagc                                                 19

<210> SEQ ID NO 6
<211> LENGTH: 34
<212> TYPE: DNA
<213> ORGANISM: Neisseria gonorrhoeae

<400> SEQUENCE: 6
cccccacggc gattccgcag tttacgacac catc                                34

<210> SEQ ID NO 7
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 7
cccccacggc gattcc                                                    16
```

```
<210> SEQ ID NO 8
<211> LENGTH: 21
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (1)..(1)
<223> OTHER INFORMATION: Conjugated to a biotin moiety via a linker

<400> SEQUENCE: 8
gatggtgtcg taaactgcgg a                                         21

<210> SEQ ID NO 9
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 9
cccccacggc gattcc                                               16

<210> SEQ ID NO 10
<211> LENGTH: 34
<212> TYPE: DNA
<213> ORGANISM: Neisseria gonorrhoeae

<400> SEQUENCE: 10
cccccacggc gattccgcag tttacgacac catc                           34

<210> SEQ ID NO 11
<211> LENGTH: 21
<212> TYPE: DNA
<213> ORGANISM: Artificial Sequence
<220> FEATURE:
<223> OTHER INFORMATION: reverse-complement of oligonucleotide primer

<400> SEQUENCE: 11
tccgcagttt acgacaccat c                                         21

<210> SEQ ID NO 12
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 12
gatggtgtcg taaactgcgg a                                         21

<210> SEQ ID NO 13
<211> LENGTH: 16
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: (1)..(1)
<223> OTHER INFORMATION: amine-reactive moiety conjugated via a linker

<400> SEQUENCE: 13
cggcgattcc gcagtt                                               16

<210> SEQ ID NO 14
```

```
<211> LENGTH: 15
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: (1)..(1)
<223> OTHER INFORMATION: amine-reactive moiety conjugated via a linker

<400> SEQUENCE: 14
cggcgattcc gcagt                                                15

<210> SEQ ID NO 15
<211> LENGTH: 15
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: (1)..(1)
<223> OTHER INFORMATION: amine-reactive moiety conjugated via a linker

<400> SEQUENCE: 15
cggtgattcc gcagt                                                15

<210> SEQ ID NO 16
<211> LENGTH: 15
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: (1)..(1)
<223> OTHER INFORMATION: amine-reactive moiety conjugated via a linker

<400> SEQUENCE: 16
cggctattcc gcagt                                                15

<210> SEQ ID NO 17
<211> LENGTH: 15
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: (1)..(1)
<223> OTHER INFORMATION: amine-reactive moiety conjugated via a linker

<400> SEQUENCE: 17
cggcgattcg gcagt                                                15

<210> SEQ ID NO 18
<211> LENGTH: 19
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: (1)..(1)
<223> OTHER INFORMATION: amine-reactive moiety conjugated via a linker

<400> SEQUENCE: 18
cacggctatt ccgcagttt                                            19
```

```
<210> SEQ ID NO 19
<211> LENGTH: 19
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: (1)..(1)
<223> OTHER INFORMATION: amine-reactive moiety conjugated via a linker

<400> SEQUENCE: 19
tacggctatt ccgcagttt                                                    19

<210> SEQ ID NO 20
<211> LENGTH: 19
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (1)..(1)
<223> OTHER INFORMATION: Conjugated to a biotin moiety via a linker

<400> SEQUENCE: 20
gatggtgtcg taaactgcg                                                    19

<210> SEQ ID NO 21
<211> LENGTH: 21
<212> TYPE: DNA
<213> ORGANISM: Artificial Sequence
<220> FEATURE:
<223> OTHER INFORMATION: oligonucleotide probe

<400> SEQUENCE: 21
tcatcggtaa ataccacccc c                                                 21

<210> SEQ ID NO 22
<211> LENGTH: 68
<212> TYPE: DNA
<213> ORGANISM: Neisseria gonorrhoeae

<400> SEQUENCE: 22
cgcgcatcgt cggcgacgtc atcggtaaat accacccca cggcgattcc gcagtttacg        60
acaccatc                                                                68

<210> SEQ ID NO 23
<211> LENGTH: 11
<212> TYPE: DNA
<213> ORGANISM: Artificial Sequence
<220> FEATURE:
<223> OTHER INFORMATION: oligonucleotide probe

<400> SEQUENCE: 23
ataccacccc c                                                            11
```

DEVICES AND METHODS FOR ANTIBIOTIC SUSCEPTIBILITY TESTING

CROSS-REFERENCE TO RELATED APPLICATIONS

This application is a divisional of U.S. application Ser. No. 17/139,451, filed Dec. 31, 2020, now U.S. Pat. No. 11,352,675, issued on Jun. 7, 2022, which claims priority to U.S. Application No. 62/957,068, filed Jan. 3, 2020, which is incorporated by reference herein in its entirety. This application is related to International Patent Application No. PCT/US2019/049385, entitled "Devices and Methods for Antibiotic Susceptibility Testing," filed Sep. 3, 2019, which is incorporated herein by reference in its entirety.

STATEMENT REGARDING FEDERALLY SPONSORED RESEARCH

This invention was made with government support under SBIR Grant No. 1R44AI143012 awarded by National Institute of Health. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: VISB_016_01WO_SeqList_ST25.txt, date recorded: Dec. 30, 2020, tile size 23 kilobytes).

BACKGROUND

The embodiments described herein relate to devices and methods for molecular diagnostic testing. More particularly, the embodiments described herein relate to devices and methods for determining the presence of a target organism and also for determining whether the organism is resistant to or susceptible to a treatment regimen (e.g., an antibiotic).

Diagnosis of drug resistance is an important problem in infectious disease medicine generally. In clinical practice non-genetic methods of drug resistance or sensitivity determination are used, for example as reviewed in Stratton, C W. Advanced Phenotypic Antimicrobial Susceptibility Testing Methods, *Advanced Techniques in Diagnostic Microbiology* (Tang et al, eds., 2018).

As one example, the CDC has identified drug resistant *Neisseria gonorrhoeae* (drNG) as an urgent threat, with approximately 20 percent of the roughly 820,000 new *Neisseria gonorrhoeae* (NG) infections each year being antibiotic resistant and thus becoming virtually untreatable. Moreover, the overall number of gonorrhea infections is increasing dramatically. According to a recent U.S. Centers for Disease Control and Prevention (CDC) press release, the yearly increase in gonorrhea diagnoses is over 50 percent. Experts agree that treating patients with the narrowest, but still effective, antibiotic for their infection will slow the development of resistance against extended-spectrum cephalosporins, while extending the utility of older antibiotics. Such treatment, however, requires clinicians to assess drug resistance or sensitivity in real time to inform prescription decisions. Unfortunately, many known tests for sexually transmitted infections (STIs) are lab-based tests that have a sample-to-result-to-patient timeline of 3-5 days. This is a significant problem as many patients are "lost-to-care" before the test result is available, and without treatment, continue to spread the disease. To prevent patients being lost-to-care, many physicians prescribe antibiotics before receiving test results, thus promoting antimicrobial resistance.

Compounding the problem, current lab tests do not provide drug sensitivity information to guide treatment. Even if existing STI lab tests provided drug sensitivity information, the lengthy time-to-result would preclude providing physicians with meaningful, real-time clinical guidance for patient treatment. For example, the agar dilution tests to determine NG antibiotic susceptibility are known to take 48-72 hours. As a result, the standard of care for treatment of NG patients includes treatment with parenteral ceftriaxone (CRO) plus oral azithromycin (AZI), a last resort antibiotic, for all cases of NG, regardless of resistance status. Even though treatment failure with the dual CRO+AZI therapy has yet to be seen in the US, it is a matter of time until resistance to this last line of defense develops, especially given the recent 2018 case of gonorrhea in the UK that was resistant to the recommended dual CRO+AZI regimen.

Some known methods of molecular diagnostic testing include testing for the presence of a genetic marker, such as a single nucleotide polymorphisms (SNP). A SNP is the substitution of a single nucleotide at a particular position in the genome of an organism, observed at some relevant frequency in the population. The observed variant nucleotides at that position are termed alleles. The detection of particular alleles of SNPs has wide utility in medicine. In particular, the detection of particular alleles serve to diagnose the presence or severity of inherited genetic disorders, to personalize treatment for cancer, or for selection of appropriate treatments for infection disease. Known methods involving the detection of SNPs, however, often include melting curve analysis and/or complicated detection chemistries, and are therefore not suitable for an affordable, point-of-care test device.

Some known molecular diagnostic test methods employ probes designed to bind to a target organism or portion of an amplified nucleic acid to provide information regarding the presence or absence of a pathogen. Such known methods, however, are often limited to tests in which the organism load within the sample is within a predetermined range. For example, in instances where the organism load is too high, non-specific binding may result and limit the accuracy of the test.

Thus, a need exists for improved devices and methods for molecular diagnostic testing. In particular, a need exists for a highly sensitive and specific, affordable, point-of-care (POC) diagnostic that provides rapid actionable result to the clinician. Such improved devices and methods would ensure that patients receive the appropriate course of treatment (e.g., antibiotic), and be highly sensitive and specific over a wide dynamic range of organism concentration within the input sample. A need exists for devices and methods to minimize the use of broad-spectrum ceftriaxone, lowering the evolutionary selection pressure on last-line antibiotics, and extending the utility of older antibiotics.

SUMMARY

Molecular diagnostic test devices and methods are described herein. In some embodiments, a method includes detecting within a disposable molecular diagnostic test device and from a single urogenital sample, the presence of a pathogen (e.g., NG) and determining whether the infecting strain is susceptible to certain antibiotics. For example, in some embodiments, the method includes determining whether the infecting strain is resistant to three classes of antibiotics—ciprofloxacin, cefixime, or zoliflodacin. In some embodiments, the method includes determining the genotype of the infecting strain—such as, without limitation, WT-gyraseA-Ser91 (ciprofloxacin susceptible) or penA-mosaic-XXXIV (reduced cefixime susceptibility)—and providing, based on the determination, individualized treatment to patients. In this manner, the ineffective use of antibiotics (e.g. ceftriaxone) can be minimized. In some embodiments, a method includes detecting within a disposable molecular diagnostic test device and from a single blood sample, the presence of a pathogen and determining whether the infecting strain is susceptible to certain antibiotics. In some embodiments, a method includes detecting within a disposable molecular diagnostic test device and from a single sputum sample, the presence of a pathogen and determining whether the infecting strain is susceptible to certain antibiotics. In some embodiments, a method includes detecting within a disposable molecular diagnostic test device and from a single respiratory sample, the presence of a pathogen and determining whether the infecting strain is susceptible to certain antibiotics.

Devices and methods disclosed herein include detection of a single nucleotide polymorphism (SNP) associated with either resistance to a treatment or susceptibility to a treatment, or both resistance and susceptibility to a treatment. In some embodiments, a method includes detecting the presence of: A) a target organism and B) at least one of a first target allele within the target organism associated with resistance to a treatment or a second target allele within the target organism associated with susceptibility to the treatment using a molecular diagnostic test device. The method includes conveying a biological sample suspected of comprising a polynucleotide from the target organism into a sample preparation module within the molecular diagnostic test device. The molecular diagnostic test device is then actuated to cause the molecular diagnostic test device to mix the biological sample with a primer set targeting a locus in a polynucleotide associated with the target organism, a SNP locus in the polynucleotide. The molecular diagnostic test device heats the biological sample and the primer set in an amplification module to amplify the polynucleotide to produce an output solution containing a first amplicon comprising the first locus (e.g., detecting presence of the organism) and a second amplicon comprising the SNP locus (e.g. detecting antibiotic resistance or susceptibility). The molecular diagnostic test device reacts in a detection module within the molecular diagnostic test device the first amplicon with a first probe to facilitate production of a first signal indicating the presence of the target organism in the biological sample. The molecular diagnostic test device reacts within the detection module the second amplicon with at least one of a second probe or a third probe to facilitate production of at least one of a second signal indicating the presence of the first target allele within the target organism or a third signal indicating the presence of the second target allele within the target organism. The method further includes reading a result associated with at least one of the first signal, the second signal, or the third signal.

In some embodiments, a method of detecting the presence of a target organism and the presence of at least one of a first target allele within the target organism associated with resistance to a treatment or a second target allele within the target organism associated with susceptibility to the treatment using a molecular diagnostic test device includes mixing within the molecular diagnostic test device a biological sample suspected of comprising a polynucleotide from the target organism with a primer set targeting a first genetic locus in a polynucleotide associated with the target organism and a second genetic locus associated with a single nucleotide polymorphism (SNP) locus in the polynucleotide. The biological sample and the primer set are heated, in an amplification module within the molecular diagnostic test device, to amplify the polynucleotide to produce an output solution containing a first amplicon comprising the first genetic locus and a second amplicon comprising the second genetic locus. The first amplicon is reacted with a first probe and the second amplicon is reacted with a second probe and a third probe in a detection module within the molecular diagnostic test device. The first probe is designed to bind to the first genetic locus. The second probe designed to bind to the second genetic locus if the second genetic locus comprises the first target allele and the third probe designed to bind to the second genetic locus if the second genetic locus comprises the second target allele. A reagent is reacted, in the detection module, with at least one of the first genetic locus or the second genetic locus to facilitate production of at least one of a first signal, a second signal, or a third signal. The first signal indicates the presence of the target organism in the biological sample. The second signal indicates the presence of the first target allele within the target organism associated with resistance to the treatment. The third signal indicates the presence of the second target allele within the target organism associated with susceptibility to the treatment.

In some embodiments, a molecular diagnostic test device includes a sample preparation module, an amplification module, a detection module, and a reagent module. The sample preparation module contains a primer set and is configured to mix the primer set with a biological sample to produce an input solution. The biological sample is suspected of comprising a polynucleotide from a target organism. The primer set targets a first genetic locus in a polynucleotide associated with the target organism and a second genetic locus in a polynucleotide associated with a single nucleotide polymorphism (SNP) locus in the polynucleotide. The amplification module includes a reaction volume and a heater. The reaction volume is configured to receive the input solution and the heater is configured to convey thermal energy into the reaction volume to amplify the polynucleotide to produce an output solution containing a first amplicon comprising the first genetic locus and a second amplicon comprising the second genetic locus. The detection module includes a first probe, a second probe, and a third probe. The first probe is designed to bind to the first genetic locus, the second probe is designed to bind to the second genetic locus if the second genetic locus comprises a first target allele associated with resistance of the target organism to a treatment, and the third probe is designed to bind to the second genetic locus if the second genetic locus comprises a second target allele associated with susceptibility of the target organism to the treatment using a molecular diagnostic test device. The reagent module contains a reagent formulated to facilitate production of a first signal, a second signal, and a third signal. The first signal indicates the presence of the bound first genetic locus, the second signal indicates the presence of the hound second genetic locus that comprises the first target allele, and the third signal indicates the presence of the bound second genetic locus that comprises the second target allele.

In some embodiments, a detection module of a molecular diagnostic device configured to detect the presence of a target organism and the presence of at least one of a first target allele within the target organism associated with resistance to a treatment or a second target allele within the target organism associated with susceptibility to the treatment includes a flow member, a first detection surface, a second detection surface, and a third detection surface. The flow member defines a detection channel configured to receive an output solution from an amplification module. The output solution containing a first amplicon comprising a locus in a polynucleotide associated with the target organism and a second amplicon comprising a SNP locus in a polynucleotide from the target organism. The first detection surface is within the detection channel and has a first probe adhered thereto. The first probe is designed to bind to the locus in a polynucleotide associated with the target organism and facilitate production of a first signal indicating the presence of the target organism. The second detection surface is within the detection channel and has a second probe adhered thereto. The second probe is designed to bind to the SNP locus if the SNP locus comprises the first target allele and facilitate production of a second signal indicating the presence of the first target allele within the target organism associated with resistance to the treatment. The third detection surface is within the detection channel and has a third probe adhered thereto. The third probe is designed to bind to the SNP locus if the SNP locus comprises the second target allele and facilitate production of a third signal indicating the presence of the second target allele within the target organism associated with susceptibility to the treatment.

In some embodiments, the second probe and the third probe are asymmetrical. In some embodiments, the second probe has a second probe melting temperature for hybridization to the second amplicon comprising the first target allele and the third probe has a third probe melting temperature for the second amplicon comprising the second target allele, the second probe melting temperature being less than the third probe melting temperature. In some embodiments, the second probe melting temperature is at least 5° C. less than the third probe melting temperature. In some embodiments, the second probe melting temperature is at least 10° C. less than the third probe melting temperature. In some embodiments, the second probe melting temperature is at least 15° C. less than the third probe melting temperature. In some embodiments, the second probe comprises an exact match to a SNP associated with drug susceptibility. In some embodiments, the second probe comprises an exact match to the codon encoding gyrA Ser-91. In some embodiments, the third probe comprises an exact match to a SNP associated with drug resistance. In some embodiments, the third probe comprises an exact match to the codon encoding gyrA Phe-91, gyrA Tyr-91, gyrA Asn-95 and gyrA Gly-95. In some embodiments, the first probe is substantially complementary or at least 70% complementary to a non-polymorphic sequence in the genome of the target organism. In some embodiments, the non-polymorphic sequence specifically identifies the target organism. In some embodiments, the non-polymorphic sequence distinguishes the target organism from a reference organism. In some embodiments, the target organism is *N. gonorrhoeae*. In some embodiments, the target organism is *N. gonorrhoeae*. In some embodiments, the reference organism is *N. subflava*.

In some embodiments, a computer-implemented method of detecting the presence of a colorimetric signal produced by a molecular diagnostic test device to indicate at least one of the presence of a target organism, a first target allele within the target organism associated with resistance to a treatment, or a second target allele within the target organism associated with susceptibility to the treatment includes receiving, at a photodetector of an electronic system of the molecular diagnostic test device, a first light signal for a first time period before a reagent is introduced into a detection module of the molecular diagnostic test device. The detection module includes a detection surface having a probe adhered thereto. The probe is designed to bind to at least one of a first amplicon associated with the target organism, a second amplicon comprising the first target allele, or a third amplicon comprising the second target allele. The reagent is formulated to facilitate production of the colorimetric signal from the detection surface. The signal indicates the presence of at least one of the bound first amplicon, the bound second amplicon, or the bound third amplicon. The first light signal is associated with a light beam conveyed through the detection module and onto the detection surface. The method further includes determining a first slope of the first light signal during the first time period. A second light signal is received at the photodetector for a second time period after the reagent is introduced into the detection module. The second light signal is associated with the light beam conveyed through the detection module and onto the detection surface. The method includes determining a second slope of the second light signal during the second time period. A signal indicating the presence of the colorimetric signal is produced when a slope difference between first slope and the second slope exceeds a predetermined threshold.

In an aspect, the disclosure provides a molecular diagnostic device comprising a sample preparation module configured to receive a biological sample, wherein the biological sample comprises a polynucleotide; a reagent module containing a primer set targeting a single nucleotide polymorphism (SNP) locus in the polynucleotide; an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele.

In another aspect, the disclosure provides a method, comprising a) introducing into any of the molecular diagnostic devices of the disclosure a biological sample from a subject having or suspected of having a disease or disorder characterized by one or more SNPs associated with susceptibility to a treatment, wherein the biological sample comprising a polynucleotide from the subject, b) administering the treatment if the molecular diagnostic device indicates the polynucleotide comprises a SNP locus comprising an allele associated with susceptibility to the treatment.

In another aspect, the disclosure provides a method, performed in a molecular diagnostic device comprising a sample preparation module configured to receive a biological sample, wherein the biological sample comprises a polynucleotide from a target organism; a reagent module containing a primer set targeting a single nucleotide polymorphism (SNP) locus in the polynucleotide; an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele. The method comprises amplifying a target amplicon from the polynucleotide from the target organism; optionally, amplifying a second target amplicon from the polynucleotide from the target organism; reacting the first target amplicon with a first probe to produce a first signal indicating susceptibility of the target organism to drug; optionally, reacting the first target amplicon with a second probe to produce a second signal indicating presence of the target organism in the biological sample and/or amplification of the target amplicon; and optionally, reacting the second target amplicon with a third probe to produce a third signal indicating presence of the target organism in the biological sample and/or amplification of either or both of the first target amplicon and the second target amplicon.

In another aspect, the disclosure provides a method, performed in a molecular diagnostic device comprising a sample preparation module configured to receive a biological sample, wherein the biological sample comprises a polynucleotide from a target organism; a reagent module containing a primer set targeting a single nucleotide polymorphism (SNP) locus in the polynucleotide; an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele; the method comprising: performing a molecular diagnostic test on the biological sample to determine A) the presence of a target organism and B) the presence of the target allele within the target organism that confers resistance to a first antibiotic; and administering, based on a result of the molecular diagnostic test, a second antibiotic.

In some embodiments, a method includes amplifying a first gene to produce a first target amplicon associated with a organism. A second gene is amplified to produce a second target amplicon associated a drug susceptibility mutation. The method further includes reacting the first target amplicon with a first probe to produce a first signal indicating a presence of the organism and reacting the second target amplicon with a second probe to produce a second signal indicating that the organism is susceptible to a drug.

In some embodiments, the amplifying the first gene and the amplifying the second gene are performed simultaneously within a stand-alone device. In some embodiments, neither the reacting the first target amplicon nor the reacting the second target amplicon includes producing a melting curve. Similarly stated, the second signal is produced without performing any melting curve analysis.

DETAILED DESCRIPTION

Figure 1:
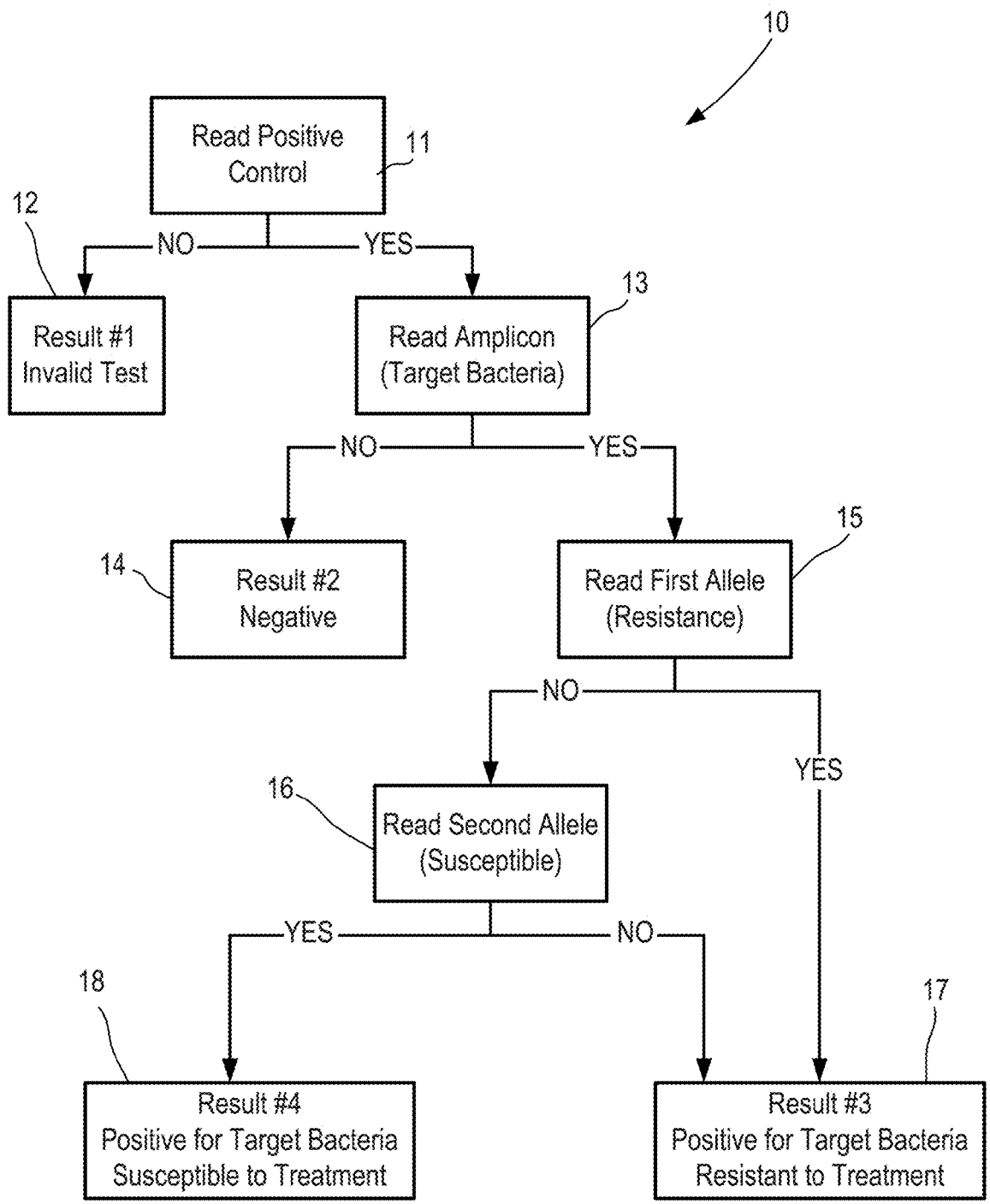
FIG. 1 is a schematic illustration of a method detecting a target organism and whether the target organism is susceptible to a treatment regimen or resistant to the treatment regimen using a combined test, according to an embodiment.

In some embodiments, an apparatus is configured for a disposable, portable, single-use, inexpensive, molecular diagnostic approach. The apparatus can include one or more modules configured to perform high quality molecular diagnostic tests, including, but not limited to, sample preparation, nucleic acid amplification (e.g., via polymerase chain reaction, isothermal amplification, or the like), and detection.

As used in this specification and the appended claims, the term "reagent" includes any substance that is used in connection with any of the reactions described herein. For example, a reagent can include an elution buffer, a PCR reagent (e.g., a primer), an enzyme, a substrate, a wash solution, or the like. A reagent can include a mixture of one or more constituents. A reagent can include such constituents regardless of their state of matter (e.g., solid, liquid or gas). Moreover, a reagent can include the multiple constituents that can be included in a substance in a mixed state, in an unmixed state and/or in a partially mixed state. A reagent can include both active constituents and inert constituents. Accordingly, as used herein, a reagent can include non-active and/or inert constituents such as, water, colorant or the like.

The term "organism" may refer to a microorganism, such as one or more bacteria, fungi, protozoa, viruses. In some embodiments, the organism is multicellular (e.g., a worm or other parasite). The organism may be pathogenic. Illustrative organisms include *Bacillus, Bartonella, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus. Treponema, Ureaplasma, Vibrio, Yersinia*. In some embodiments, the organism is a virus. Non-limiting examples of viruses are described throughout this disclosure.

The term "nucleic acid molecule," "nucleic acid," or "polynucleotide" may be used interchangeably herein, and may refer to deoxyribonucleic acid (DNA) or ribonucleic acid (RNA), including known analogs or a combination thereof unless otherwise indicated. Nucleic acid molecules to be profiled herein can be obtained from any source of nucleic acid. The nucleic acid molecule can be single-stranded or double-stranded. In some cases, the nucleic acid molecules are DNA. The DNA can be mitochondrial DNA, complementary DNA (cDNA), or genomic DNA. In some cases, the nucleic acid molecules are genomic DNA (gDNA). The DNA can be plasmid DNA, cosmid DNA, bacterial artificial chromosome (BAC), or yeast artificial chromosome (YAC). The DNA can be derived from one or more chromosomes. For example, if the DNA is from a human, the DNA can be derived from one or more of chromosomes 1, 2, 3, 4, 5, 6, 7, 8, 9, 10, 11, 12, 13, 14, 15, 16, 17, 18, 19, 20, 21, 22, X, or Y. In some cases, the nucleic acid molecules include, but are not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA can include snoRNAs, microRNAs, siRNAs, piRNAs and long nc RNAs. Bacterial resistance may be conferred by plasmids or phage and in such cases the polynucleotide may be the plasmid or the phage genome. In some embodiments, "a polynucleotide associated with a target organism" refers to two or more polynucleotides. For example, detection of a locus on a first polynucleotide (e.g., the genomic DNA of the organism) is used to detect presence of the organism while resistance or susceptibility to a drug is determined by detection of the plasmid or phage associated with the target organism. The source of nucleic acid for use in the devices, methods, and compositions described herein can be a biological sample comprising the nucleic acid.

Terms and symbols of nucleic acid chemistry, biochemistry, genetics, and molecular biology used herein follow those of standard treatises and texts in the field, e.g., Kornberg and Baker, *DNA Replication*, Second Edition (W. H. Freeman, New York, 1992); Lehninger, Biochemistry, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

Polymorphisms, in general, refer to changes of a nucleotide at a single base-pair location on a nucleic acid. A polymorphism means a substitution, inversion, insertion, or deletion of one or more nucleotides at a genetic locus, or a translocation of DNA from one genetic locus to another genetic locus. A "single nucleotide polymorphism" or "SNP" as used herein refers to a substitution of one nucleotide in the polynucleotide sequence of a genome of an organism with respect to a reference sequence (e.g. the wild-type sequence of the organism, or any alternative sequence variant present in a population of organisms of the same species). For example, a SNP in an organism is a nucleotide position that differs between representatives of that species; a SNP is a human population is a nucleotide position that differs between representatives between individuals; and a SNP in the context of cancer is a nucleotide position that differs between the genome of the subject and the genome of tumor cells within the subject. The term "polymorphic locus" refers to a locus comprising a polymorphism (e.g. a SNP) and sufficient flanking polynucleotide sequences to permit detection by a probe.

An "allele" refers to a particular polymorphism (e.g., a nucleotide at the SNP) whose detection is desired. When the SNP is in a coding sequence, the allele may encode a change in the protein encoded by the polynucleotide (or "target region"). An "antiallele" refers to nucleotide present at the same position (i.e. the SNP locus) in the reference sequence. In the case of drug-resistance detection, the drug-resistance allele is the nucleotide whose presence in the polynucleotide confers a phenotype (e.g., resistance or susceptibility) on the organism. The antiallele refers to an allele that confers the opposite phenotype on the organism. Conversely, in the detection of drug sensitivity, the "allele" is the nucleotide at the SNP locus that covers sensitivity to the drug; the "antiallele" is the nucleotide at the SNP locus of the reference sequence, the same organism having resistance to the drug. When more than two alternative nucleotides are observed at the same position in a sequence (the SNP locus), the "allele" is the nucleotide to be detected, and the two or three alternative nucleotides are "antialleles."

Such SNPs can occur in organisms with highly variable genomes, such as pathogens in general. One of skill will readily understand and identify pathogens in general and those characterized with highly variable genomes. Such pathogens include such as viruses, organism, parasites and fungi. The devices and methods described herein are not limited to any particular SNP, as the devices and methods described herein are intended to determine the presence of a various SNPs. SNP can readily be identified in literature in various organisms.

Once an organism is selected, target nucleic acid sequences for the organism, for example a SNP locus, may be determined as being known in the literature or may be determined by sequencing methods (e.g., by comparative analysis of drug-resistant and drug-sensitive organisms). Once a target SNP locus is identified, the 5' and 3' flanking sequences can be identified by retrieving the sequence from any of various public databases (e.g. GenBank) or sequencing the locus anew. A 5' flanking region is a nucleic acid sequence which lies 5' to a target nucleotide position. A 3' flanking region is a nucleic acid sequence which lies 3' to a target nucleotide position. In some cases, the 5' flanking region is immediately adjacent to, or within about 20 bp, 40 bp, 60 bp, 80 bp, or 100 bp of the SNP locus. In some case, the 3' flanking region is immediately adjacent to, or within about 20 bp, 40 bp, 60 bp, 80 bp, or 100 bp of the target nucleotide position. From the sequence information of the target nucleotide (i.e. the allele) at the target nucleotide position (i.e., the SNP locus) and the 5' and 3' flanking regions, a probe including can be designed as described herein.

The term "probe" as used herein refers to an unlabeled oligonucleotide used to capture a target amplicon. Generally the probe is covalently conjugated to a surface of the detection module, although non-covalent conjugated methods may also be employed. An illustrative, non-limiting means for conjugating a probe to a substrate is a amide coupled. In some embodiments, the surface of the detection module comprises an amorphous polymer (e.g., a cyclic olefin copolymer (COC)). Surface modification of a COC substrate surface can be achieved by oxygen plasma treatment, such as described in Hwang et al. *Surface and Coatings Technology*, 202:3669-74 (2008); Gubala et al. *Colloids and Surfaces B: Biointerfaces* 81:544-48 (2010); or Carvalho et al. *ACS Applied Materials and Interfaces* 9:16644-50 (2017). Following activation of the substrate (e.g. a COC substrate) to yield an amine-reactive substrate (e.g. carboxylated COC), amino-modified oligonucleotides can be coupled to the surface by various attachment chemistries including but not limited to acrylic phosphoramidite (Acrydite™), adenylation, azide (NHS ester), I-Linker™ (to aldehyde or ketone-modified substrates), or amino modifiers. A primary amino group can be used to attach the oligonucleotide probes to the surface. Amino modifiers can be positioned at the 5'-end with either a standard (C6) or longer (C12) spacer arm. Amino modifications can also be positioned at the 3'-end. Internal amino modifications can be introduced using an amino-dT base. Illustrative amino modifiers include a 3' amino modifier C6, 3' amino modifier C12, 5' amino modifier C6, and a 5' amino modifier C12. A "resistance probe" is a probe that binds preferentially to an allele associated with resistance to treatment (e.g. drug treatment). A "susceptible probe" or "sensitive probe" is a probe that binds preferentially to an allele associated with susceptible to treatment (e.g. drug treatment).

The devices and methods described herein are not limited to detection of one SNP. Rather, two or more or a plurality of SNP locuses (or "loci") in the same target amplicon may be detected. In some embodiments, a single oligonucleotide probe is designed to specifically bind a probe binding region comprising two or three SNP locuses. In some embodiments, the device includes a detection module having probes against one, two, three, or more sites present on a single target amplicon. In some embodiments, the device is configured to detect SNPs in multiple target amplicons from the same and/or different organisms. In certain embodiments, the device is configured to detect one, two, three, or four SNPs in the same organism. In certain embodiments, the device is configured to detect one, two, three, or four SNPs in the different organisms. For example, and without limitation, in some embodiments, the devices of the disclosure comprise probes for detection of one or more of chlamydia, gonorrhoea, and/or trichomonas. In some embodiments, the probes for each pathogen are specific for a drug-resistance SNP or drug-sensitivity SNP. In some embodiments, the devices of the disclosure further comprises a second probe specific for (e.g., substantially complementary to) a non-overlapping region of the target amplicon. In some embodiments, this second probe serves as a control for the presence of absence of the organism in the biological sample.

"Genetic locus" or "locus" or "target region" refers to a contiguous sub-region or segment of a genome. As used herein, a "SNP locus" refers the nucleotide position within a genome where a single nucleotide polymorphism occurs. The SNP locus can be named to according to its position within the genome, or by its position in the coding sequence of a protein gene product encoded by the genome of the organism. For example, a SNPs at the gyrA Ser-91 site refers to a SNP at one of the three nucleotide positions in the genome of the organism that correspond to the codon that, during translation of the messenger RNA transcribed from the gyrA gene, directs the ribosome to add a serine as the 91st amino acid in the gyrA gene product.

Target nucleic acid sequences or target polynucleotides include genomic nucleic acids of a particular organism. Such target nucleic acid sequences may be single stranded or double stranded and may include a sense strand and/or an antisense strand. Such target nucleic acid sequences may be a deoxyribonucleic acid ("DNA") or a ribonucleic acid ("RNA").

As used herein, a "biological sample" refers to any tissue or fluid obtained from an organism (e.g. a subject, e.g. a human or animal subject) that contains a polynucleotide (e.g., DNA or RNA) that can be amplified and/or detected by the devices described herein. In some embodiments, any of the devices and methods described herein can be conducted on a variety of different types of samples. Such sample types can include, for example, vaginal swab, penile meatal swab sample, a buccal swab, stool, sputum, nasal wash, nasal aspirate, throat swab, bronchial lavage, blood, blood cells (e.g. white blood cells), fine needle biopsy samples, peritoneal fluid, visceral fluid, pleural fluid, a urine sample, rectal swab sample and/or pharyngeal swab sample, or cells therefrom. A series of tests was performed with vaginal swab samples. Other biological samples useful in the present invention include tumor samples (e.g. biopsies) and blood samples from subjects having or suspected of having a lymphoproliferative disorder.

In some embodiments, methods of the present disclosure are utilized to detect infections with microorganisms which are potentially resistant to antimicrobial drug treatment. Non-limiting examples of microorganisms include: e.g. one or more of *Acinetobacter, Escherichia*, e.g. *E. coli, Enterobacter, Klebsiella*, e.g. *Klebsiella pneumonia* and/or *Klebsiella oxytoca, Mycoorganism*, e.g. *Mycoorganism tuberculosis, Neisseria*, e.g. *Neisseria meningitides* and/or *Neisseria gonorrhoaea, Proteus*, e.g. *Proteus mirabilis, Pseudomonas*, e.g. *Pseudomonas aeruginosa, Salmonella*, e.g. *Salmonella enterica, Serratia*, e.g. *Serratia marcescens, Staphylococcus*, e.g. *Staphylococcus aureus, Stenotrophomonas*, e.g. *Stenotrophomonoas maltophilia, Streptococcus*, e.g. *Streptococcus pneumonia* and/or *Streptococcus pyogenes* and/or *Streptococcus parauberis, Shigella, Haemophilus*, e.g. *Haemophilus influenza, Vibrio*, e.g. *Vibrio harveyi*, and/or *Edwardsiella*, e.g. *Edwardsiella tarda*.

In some embodiments, identification of organisms will define an antimicrobial treatment regime. For example if a Gram-positive organism is determined to the primary pathogen, the patient would receive a gram-positive appropriate antibiotic such as vancomycin. In addition, if the assay determines that a specific organism is present that possesses resistance determinants for a number of antibiotics, these therapeutic options would be avoided for that particular patient.

Non-limiting examples of antimicrobials include β-lactams, β-lactam inhibitors, guinolones and derivatives thereof, e.g. fluoroquinolones, aminoglycosides, glycopeptides, lincosamides, macrolides, nitrofuranes, oxazolidinones, polyketides, respectively tetracyclines, and folate synthesis inhibitors, e.g. benzene derived/sulfonamide antibiotics. According to certain embodiments, the antimicrobial drug, e.g. antibiotic drug, is selected from the group consisting of Amoxicillin/K Clavulanate (AUG), Ampicillin (AM), Aztreonam (AZT), Cefazolin (CFZ), Cefepime (CPE), Cefotaxime (CFT), Ceftazidime (CAZ), Ceftriaxone (CAX), Cefuroxime (CRM), Cephalotin (CF), Ciprofloxacin (CP), Ertapenem (ETP), Gentamicin (GM), Imipenem (IMP), Levofloxacin (LVX), Meropenem (MER), Piperacillin/Tazobactam (P/T), Ampicillin/Sulbactam (A/S), Tetracycline (TE), Tobramycin (TO), and Trimethoprim/Sulfamethoxazole (T/S).

In some embodiments, antimicrobial resistance is identified by detecting SNPs in organism genes. The SNP targets represent selected genes known to be associated with organism antibiotic resistance bearing mutations in those genes that are deemed determinants of resistance.

In some embodiments, methods of the present disclosure detect one or more bacterial SNPs in genes selected from the group consisting of 16S rRNA, ethA, ndh, 23S rRNA, fabG1, parC, ahpC, folP, parE, air, gyrA, pncA, embA, gyrB, rlmN, embB, kasA, rpoB, embC, katG, rpsL, vraR, vraS, parC, mtrR, penA, penB, mtrR, ponA, rpsJ, and atpE. For example, resistance to a macrolide (e.g., clarithromycin, azithromycin, fidoximycin, erythromycin, etc.) may be determined by assaying SNPs in the 23S rRNA of organisms including but not limited to NG and *Mycoplasma genitalium* (Mgen).

In some embodiments, methods of the present disclosure detect spectinomycin resistance associated with one or more SNPs in the gene encoding mtrR.

In some embodiments, methods of the present disclosure detect penicillin resistance associated with one or more SNPs in the group of genes consisting of bla, penA, ponA, penB, and mtrR.

In some embodiments, methods of the present disclosure detect vancomycin resistance associated with one or more SNPs in vraR and/or vraS.

In some embodiments, methods of the present disclosure are used to detect tetracyclin resistance associated with one or more SNPs in rpsJ, mtrR, and tet(M).

In embodiments, methods of the present disclosure detect cephalosporin resistance associated with one or more SNPs selected from the group consisting of penA, penB, mtrR, and ponA.

In embodiments, methods of the present disclosure are utilized to detect quinolone resistance associated with one or more mutations in gyrA, parC, and mtrR.

In some embodiments, the present disclosure detects azithromycin resistance associated with a SNP in the gene encoding 16S rRNA.

The target nucleic acid sequences may be amplified using methods known to those of skill in the art. Such methods include using a polymerase, primers and nucleotides. "Amplifying" includes the production of copies of a nucleic acid molecule via repeated rounds of primed enzymatic synthesis.

Amplification methods may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) Nature Methods 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self-sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000), *J. Biol. Chem.* 275:2619; and Williams et al. (2002) *J. Biol. Chem.* 277:7790), the amplification methods described in U.S. Pat. Nos. 6,391,544, 6,365,375, 6,294,323, 6,261,797, 6,124,090 and 5,612,199, or any other nucleic acid amplification method using techniques well known to those of skill in the art. In some embodiments, the methods disclosed herein utilize linear amplification. In some embodiments, the methods disclosed herein utilize PCR amplification. In some embodiments, the PCR amplification is reverse transcription-PCR.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

The term "PCR" encompasses derivative forms of the reaction, including but not limited to, reverse transcription (RT)-PCR, nested PCR, quantitative PCR, multiplexed PCR, and the like. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. e.g., "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) Anal. Biochem., 273:221-228. Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., Biotechniques, 26:112-126 (1999); Becker-Andre et al., Nucleic Acids Research, 17:9437-9447 (1989); Zimmerman et al., Biotechniques, 21:268-279 (1996); Diviacco et al., Gene, 122:3013-3020 (1992); Becker-Andre et al., Nucleic Acids Research, 17:9437-9446 (1989); and the like.

"Oligonucleotide" or "polynucleotide," which are used synonymously, means a linear polymer of natural or modified nucleosidic monomers linked by phosphodiester bonds or analogs thereof. Accordingly the oligonucleotide or polynucleotide may be considered a polymer of natural or modified nucleotides. The term "oligonucleotide" usually refers to a shorter polymer, e.g., comprising from about 3 to about 100 monomers, and the term "polynucleotide" usually refers to longer polymers, e.g., comprising from about 100 monomers to many thousands of monomers, e.g., 10,000 monomers, or more. Oligonucleotides comprising probes or primers usually have lengths in the range of from 12 to 60 nucleotides, and more usually, from 18 to 40 nucleotides. Oligonucleotides and polynucleotides may be natural or synthetic. Oligonucleotides and polynucleotides include deoxyribonucleosides, ribonucleosides, and non-natural analogs thereof, such as anomeric forms thereof, peptide nucleic acids (PNAs), and the like, provided that they are capable of specifically binding to a target genome by way of a regular pattern of monomer-to-monomer interactions, such as Watson-Crick type of base pairing, base stacking, Hoogsteen or reverse Hoogsteen types of base pairing, or the like.

"Primer" includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers usually have a length in the range of between 3 to 36 nucleotides, also 5 to 24 nucleotides, also from 14 to 36 nucleotides. Primers within the scope of the invention include orthogonal primers, amplification primers, constructions primers and the like. Pairs of primers can flank a sequence of interest or a set of sequences of interest. Primers and probes can be degenerate in sequence. Primers within the scope of the present invention bind adjacent to a target sequence (e.g., an oligonucleotide sequence of an oligonucleotide set or a nucleic acid sequence of interest).

The term "primer set" refers one or more primers configured for amplification of a target region or target regions of polynucleotide by PCR, or the like. A "target region" refers to a predetermined region in a polynucleotide sequence (e.g., the gene or gene fragment, e.g. a gene or gene fragment associated with resistance or sensitivity to an antibiotic). According to the methods of the disclosure, a target region is selected to include the SNP locus of interest. Amplification of the target region using the primer set results in an "amplicon" or "target amplicon." The target amplicon will have the same polynucleotide sequence as the target region (albeit some insertions, deletions, or substitutions of nucleotides due to polymerase errors may occur and the methods of the disclosure are tolerant of such errors), provided that in some cases the primers of the primer set may be substantially complementary but not perfectly complementary to the primer binding site and will therefore introduce changes in the target amplicon. In cases in which the primer set contains no primer overlapping the probe binding site, such substitutions do not impact (or have margin impact) on detection of the target amplicon using probes. In cases where the assay is designed to have overlap between primer binding site and probe binding site, the probe design is generally adapted by designing the probe against the known or predicted target amplicon sequence, rather than against the target region sequence, as in such cases the two are different. A primer set may comprise 1, 2, 3, 4, 5, 6 or more oligonucleotide primers. In some embodiments, the primer set includes four oligonucleotides to permit amplification of two target regions by two pairs of primers. For example, a single primer may be used for linear amplification (e.g. rolling circle amplification), two primers, one in forward (5'→3') orientation and one in reverse (3'→5') orientation, can be used for PCR amplification. It is understood by those skill in the art that when the polynucleotide is double-stranded (e.g. double-stranded DNA) the designations "forward" and "reverse" are arbitrary. In certain embodiments, 3, 4, or more oligonucleotide primers form the primer set, such as where the molecular diagnostic device is configured to perform a nest PCR reaction. In some embodiments, two amplicons are generated by the device—i.e. a first amplicon to detect the presence of the organism and a second amplicon to detect a resistance or susceptibility phenotype. In some embodiments, the device is configured to generate a third amplicon if a reference organism is present. In some embodiments the third amplicon detected by a substantially complementary probe permits the device to discriminate between an organism (e.g. NG) and a related organism (e.g. NS), thereby eliminating a false positive detection of the target organism (e.g. NG). In some embodiments, the first amplicon is designed to target a locus conserved in the target organism but non-conserved with respect to the reference organism.

In some embodiments, the primer set is included in the molecular diagnostic device. For example, the primer set may be provided as a solid (e.g., a lyophilized powder or a table) in the device, or as a liquid (e.g., a solution or suspension provided in the device). The primer set may be provided in a separate reagent chamber, in-line in the flow path, or in another suitable portion of the device. In some embodiments, the molecular diagnostic device does not, prior to use, comprise the primer set. The primer set may be added to the biological sample before the biological sample is add to the device, or the primer set may be introduced into the device before, concurrent with, or after introduction of the biological sample into the device. Thus, in various embodiments, the molecular diagnostic device comprises the primer set, or comprises a reagent module containing a primer set, or is configured to receive a primer set.

As used herein "targeting" (as in a primer set targeting a SNP locus) refers to selection in assay development of primers in the primer set that will result, under operation of the molecular diagnostic device, in the amplification of the polynucleotide (e.g., gene or gene fragment) in the molecular diagnostic device to generate a target amplicon that includes the SNP locus, thereby permitting detection of which allele is present at the SNP locus in the detection module. In some embodiments, the SNP locus is targeted by design of a primer set comprising two or more oligonucleotides (e.g., at least one forward primer and at least one reverse primer). Where one primer (e.g., the forward primer) is upstream (or 5') to the SNP locus, and the other primer (e.g., the reverse primer) is downstream (or 3') to the SNP locus, the primer set is said to "flank" the SNP locus. A primer set may be "designed to flank" the SNP locus or "flanking" a SNP locus or other locus by selecting a first primer binding site upstream (or 5') to the locus and a second primer binding site downstream (or 3') to the locus. Primers are designed to be capable of annealing to each of the selected binding sites (e.g., by being substantially complementary to, or complementary to the primer binding site). Using methods well known in the art, primer binding sites and corresponding oligonucleotide primers can be chosen so as to optimize the performance of the amplification reaction.

In some embodiments of the present disclosure, the precise location of the primer binding sites may be changed without adverse impact on the subsequent detection step. In certain embodiments, the present inventors have observed that the length of the resulting target amplicon is, surprisingly, a result-effective variable for the detection step. Thus, in some embodiments, the target region flanked by the primer set is between about 30 base pairs (bp) and about 500 bp, about 30 bp and about 400 bp, about 30 bp and about 300 bp, about 30 bp and about 200 bp, or about 30 bp and about 150 bp. In some embodiments, the target region flanked by the primer set is between about 40 bp and about 500 bp, about 40 bp and about 400 bp, about 40 bp and about 300 bp, about 40 bp and about 200 bp, or about 40 bp and about 150 bp. In some embodiments, the target region flanked by the primer set is between about 50 bp and about 500 bp, about 50 bp and about 400 bp, about 50 bp and about 300 bp, about 50 bp and about 200 bp, or about 50 bp and about 150 bp. In some embodiments, the target region flanked by the primer set is between about 60 bp and about 500 bp, about 60 bp and about 400 bp, about 60 bp and about 300 bp, about 60 bp and about 200 bp, or about 60 bp and about 150 bp. In some embodiments, the target region flanked by the primer set is between about 70 bp and about 500 bp, about 70 bp and about 400 bp, about 70 bp and about 300 bp, about 70 bp and about 200 bp, or about 70 bp and about 150 bp.

In some embodiments, the target amplicon is between about 30 base pairs (bp) and about 500 bp, about 30 bp and about 400 bp, about 30 bp and about 300 bp, about 30 bp and about 200 bp, or about 30 bp and about 150 bp. In some embodiments, the target amplicon is between about 40 bp and about 500 bp, about 40 bp and about 400 bp, about 40 bp and about 300 bp, about 40 bp and about 200 bp, or about 40 bp and about 150 bp. In some embodiments, the target amplicon is between about 50 bp and about 500 bp, about 50 bp and about 400 bp, about 50 bp and about 300 bp, about 50 bp and about 200 bp, or about 50 bp and about 150 bp. In some embodiments, the target amplicon is between about 60 bp and about 500 bp, about 60 bp and about 400 bp, about 60 bp and about 300 bp, about 60 bp and about 200 bp, or about 60 bp and about 150 bp. In some embodiments, the target amplicon is between about 70 bp and about 500 bp, about 70 bp and about 400 bp, about 70 bp and about 300 bp, about 70 bp and about 200 bp, or about 70 bp and about 150 bp.

In some embodiments, the target region flanked by the primer set is about 30 bp, about 40 bp, about 50 bp, about 60 bp, about 70 bp, about 80 bp, about 90 bp, about 100 bp, about 110 bp, about 120 bp, about 130 bp, about 140 bp, about 150 bp, about 160 bp, about 170 bp, about 180 bp, about 190 bp, about 200 bp, about 210 bp, about 220 bp, about 230 bp, about 240 bp, about 250 bp, about 260 bp, about 270 bp, about 280 bp, about 290 bp, or any length therebetween. In some embodiments, the target amplicon is about 30 bp, about 40 bp, about 50 bp, about 60 bp, about 70 bp, about 80 bp, about 90 bp, about 100 bp, about 110 bp, about 120 bp, about 130 bp, about 140 bp, about 150 bp, about 160 bp, about 170 bp, about 180 bp, about 190 bp, about 200 bp, about 210 bp, about 220 bp, about 230 bp, about 240 bp, about 250 bp, about 260 bp, about 270 bp, about 280 bp, about 290 bp, or any length therebetween.

Primers suitable for use in the methods disclosed herein may be designed with the aid of a computer program, such as, for example, DNAWorks, Gene2Oligo, or using the parameters software described herein. Typically, primers are from about 5 to about 500, about 10 to about 100, about 10 to about 50, or about 10 to about 30 nucleotides in length. In certain exemplary embodiments, a set of primers is designed so as to have substantially similar melting temperatures to facilitate manipulation of a complex reaction mixture. The melting temperature may be influenced, for example, by primer length and nucleotide composition.

"Specific" or "specificity" in reference to the binding of one molecule to another molecule, such as a target sequence to a probe, means the recognition, contact, and formation of a stable complex between the two molecules, together with substantially less recognition, contact, or complex formation of that molecule with other molecules.

"Substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid or between an oligonucleotide probe and a probe binding site on a single stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. In some embodiments, probes described herein have 100% complementarity with their corresponding probe binding site. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See Kanehisa (1984) Nucl. Acids Res. 12:203. In some embodiments, "substantially complementary" means at least about 70%, at least about 75%, at least about 80%, at least about 85%, or at least about 90% identity to the binding site of the probe or primer.

As used herein, "substantially complementary" includes "complementary." "Complementary" means having 100% sequence identity across the full length of the sequence. I sequence remains "substantially complementary" or "complementary" even if one or more nucleotide positions comprise artificial nucleotides (e.g. locked nucleic acids). For example, the complementary polynucleotide may contain a chemically modified C (such as 5-methylcytosine) in place of an unmodified C.

In any of the embodiments provided herein, the oligonucleotide primer(s) or probe(s) may comprise one or more locked nucleic acids (LNAs). Locked nucleic acids include, without limitation, nucleotide acidic containing a 2' to 4' methylene bridge. In some embodiments provided herein, the DNA nucleotide at the second nucleotide position contains a chemically modified nitrogenous base. In any of the embodiments provided herein, the chemically modified nitrogenous base is 5-methylcytosine. In some, the oligonucleotide comprises at least one nucleotide that is 2'-deoxy, 2'O-alkyl or 2' halo modified. In some, the oligonucleotide has a 5' cap structure, 3' cap structure, or 5' and 3' cap structure. In some embodiments, the oligonucleotide comprises one or more phosphorothioate linkages.

The oligonucleotides of the present invention may comprise one or more locked nucleic acid (LNAs) residues, or "locked nucleotides." The oligonucleotide of the present invention can contain one or more locked nucleic acid (LNAs) residues, or "locked nucleotides." The oligonucleotides of the present invention may comprise one or more nucleotides containing other sugar or base modifications. The terms "locked nucleotide," "locked nucleic acid unit," "locked nucleic acid residue," "LNA" or "LNA unit" may be used interchangeably throughout the disclosure and refer to a bicyclic nucleoside analogue. For instance, suitable oligonucleotide inhibitors can be comprised of one or more "conformationally constrained" or bicyclic sugar nucleoside modifications (BSN) that confer enhanced thermal stability to complexes formed between the oligonucleotide containing BSN and their complementary target strand. LNAs are descried, for example, in U.S. Pat. Nos. 6,268,490, 6,316, 198, 6,403,566, 6,770,748, 6,998,484, 6,670,461, and 7,034, 133, all of which are hereby incorporated by reference in their entireties. LNAs are modified nucleotides or ribonucleotides that contain an extra bridge between the 2' and 4' carbons of the ribose sugar moiety resulting in a "locked" conformation, and/or bicyclic structure. The term "corresponding locked nucleotide" is intended to mean that the nucleotide has been replaced by a locked nucleotide containing the same base.

A "matched" nucleotide refers to a nucleotide that is the Watson-Crick pair of the nucleotide on the opposing strand or binding site of the probe. For example, a probe for a target allele that has an 'A' as the SNP locus is matched to the target allele if the corresponding nucleotide in the probe is a 'T'; and, likewise the probe is matched to 'T' at the SNP locus if the corresponding nucleotide is 'A'; 'G' for 'C'; and 'C' for 'G.' As is known in the art, other nucleotides, including non-natural nucleotides may be used to match the SNP locus. An "exact match" refers to perfect complementary to a polynucleotide sequence. An exact match to a SNP means that the probe comprising a nucleotide complementary to the nucleotide encoding the SNP at the same relative position in the probe. The exact match may be achieved by nature or non-natural nucleic acid bases. An exact match includes nucleotides including backbone or sugar modifications—e.g. a nucleotide comprising a locked nucleic acid (LNA) or a thiophosphate linkages is an exact match to the SNP if and only if the base portion of the nucleotide is complementary to the SNP allele.

Two oligonucleotides and/or polynucleotides that are fully or partially complementary undergo Watson-Crick type base pairing among all or most of their nucleotides so that a stable complex is formed of a sense strand and an antisense strand. The sense strand may be identified as the strand in the 5' to 3' direction in the hybridized duplex while the antisense strand may be identified as the strand in the 3' to 5' direction in the hybridized duplex. The terms "annealing" and "hybridization" are used interchangeably to mean the formation of a stable duplex. Stable duplex means that a duplex structure is not destroyed by a stringent wash, e.g., conditions including temperature of about 5° C. less that the Tm of a strand of the duplex and low monovalent salt concentration, e.g., less than 0.2 M, or less than 0.1 M. "Perfectly matched" or "100% complementarity" in reference to a duplex means that the polynucleotide or oligonucleotide strands making up the duplex form a double stranded structure with one another such that every nucleotide in each strand undergoes Watson-Crick base pairing with a nucleotide in the other strand, i.e. every nucleotide in a shorter strand undergoes Watson-Crick base pairing with a nucleotide in the other longer strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the Tm for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, Molecular Cloning A Laboratory Manual, 2nd Ed. Cold Spring Harbor Press (1989) and Anderson Nucleic Acid Hybridization, 1st Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

A probe according to the present disclosure may be referred to as a hybridization probe which is a fragment of DNA or RNA of variable length which is used in DNA or RNA samples to detect the presence of nucleotide sequences (the target amplicon) that are complementary or substantially complementary to the sequence in the probe. The probe thereby hybridizes to single-stranded nucleic acid (DNA or RNA) whose base sequence allows probe-target base pairing due to complementarity between the probe and target amplicon. The probe is linked to a surface in the detection module by covalent chemical attachment or other methods of associating an oligonucleotide with a substrate as described herein or known in the art.

To detect hybridization of the target amplicon to the probe, the target amplicon is tagged (or "labeled") with a molecular marker or label, for example a fluorescent marker or other detectable moiety such as a radioactive moiety or any enzyme capable of generating a colored or fluorescent signal in the presence of an appropriate enzyme substrate.

Depending on the method, the probe may be synthesized using the phosphoramidite method, or it can be generated and labeled by PCR amplification or cloning. Methods of making nucleic acid probes are known to those of skill in the art.

Visually detectable markers suitable for use in the devices and methods of the disclosure include various enzymes, prosthetic groups, fluorescent markers, luminescent markers, bioluminescent markers, and the like. Examples of suitable fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of suitable bioluminescent markers include, but are not limited to, luciferase (e.g., bacterial, firefly, click beetle and the like), luciferin, aequorin and the like. Examples of suitable enzyme systems having visually detectable signals include, but are not limited to, galactosidases, glucorinidases, phosphatases, peroxidases, cholinesterases and the like. Other suitable markers useful for detection of polynucleotides, are known to those of skill in the art.

In some embodiments, the primer sets of the disclosure comprise a detectable moiety, whereby amplification of a target region using the primer set results in production of a tagged target amplicon. In some embodiments, the detectable moiety is a biotin tag. Either forward primer, reverse primer, or both forward and reverse primers may be biotinylation. In some embodiments, one or both primers is biotin-tagged. After hybridization of the target amplicon to a probe, detection proceeds by introducing into the detection module of a first reagent, the first reagent comprising a biotin-labeled marker (e.g. a fluorescent marker or an enzyme system) is provided. In some embodiments, the first reagent comprises streptavidin-tagged horse radish peroxidase (HRP). After optionally removing excess of the first agent by washing the detection chamber, a second reagent may be provided. In some embodiments, the second reagent is substrate for a peroxidase (e.g. HRP)

The substrate can include, for example, any of tetramethylbenzidine (TMB), 3-ethylbenzothiazoline-6-sulfonic acid, o-phenylenediamine, Amplex Red, homovanillic acid, 3,3'-diaminobenzidine, 3-amino-9-ethylcarbazole, 5-Bromo-4-chloro-3-indolyl phosphate, 5-Bromo-4-chloro-3-indolyl phosphate/nitro blue tetrazolium, Fast Red (Sigma). In some embodiments, the substrate is TMB. In such embodiments, TMB in the detection module 2800 changes color from colorless to blue, and finally yellow above any positive chambers. The yellow color is produced when the detection module 2800 is heated to about 40° C. during the detection operation. In contrast, some ELISA based formats produce a color change that goes to blue or green, and does not proceed to yellow until it is exposed to a stop solution.

In other embodiments, the substrate of the substrate is a precipitating substrate formulated to catalyze the production of the visible signal OP by producing an insoluble colored product when the substrate is in contact with the enzyme. Such precipitating substrates can include, for example, TMB (3,3',5,5' tetramethylbenzidine), DAB (3,3' diaminobenzidine), or 4 CN (4-chloro-1-napthol) based membrane substrates for horseradish peroxidase enzymes, or BCIP (5-bromo-4-chloro-3-indolyl-phosphate) based membrane substrates for alkaline phosphatase. In some embodiments, the precipitating substrate can be the BioFX® TMB HRP Membrane Substrates produced by Surmodics. In some embodiments, the precipitating substrate can maintain stability when stored for up to one year in a liquid form at room temperature. In other embodiments, the precipitating substrate can maintain stability when stored for up to two years in a liquid form at room temperature. Moreover, such precipitating substrates can produce a dark color, which can be easier to visualize and interpret. In some embodiments, the precipitating substrate can produce a colorimetric output that persists for at least one hour, at least two hours, at least three hours, at least 12 hours, at least 24 hours, or at least 48 hours. Further illustrative detection methods are providing in International Patent Publication No. WO2018/005710A1, which is incorporated herein by reference in its entirety.

Methods for incorporating detectable labels into nucleic acids are well known. Typically, detectable labels (e.g., as hapten- or fluorochrome-conjugated deoxyribonucleotides) are incorporated into a nucleic acid during a polymerization or amplification step, e.g., by PCR, nick translation, random primer labeling, terminal transferase tailing (e.g., one or more labels can be added after cleavage of the primer sequence), and others (see Ausubel et al., 1997, Current Protocols In Molecular Biology, Greene Publishing and Wiley-Interscience, New York).

Detection method(s) used will depend on the particular detectable labels used in the nucleic acid probes. In certain exemplary embodiments, labels may be detected by a microscope, a spectrophotometer, a tube luminometer, x-ray film, a scintillator, or the like.

Methods described herein are useful in determining the presence of organisms having one or more polymorphisms within a population of organisms which include wild type organisms or organisms without the one or more polymorphisms. Organisms within the scope of the present disclosure include viruses, bacteria and fungi. Exemplary viruses include Influenza viruses, Hepatitis C virus, Dengue virus, West Nile virus, Ebola virus, Lassa virus, Sudden acute respiratory syndrome coronavirus 2 (SARS-CoV-2), Sudden acute respiratory syndrome coronavirus (SARS-CoV), Middle East Respiratory Syndrome Coronavirus (MERS-CoV) and the like. One of skill will readily understand that this list is non-limiting and that other viruses are well known to and can be readily identified by those of skill in the art. Exemplary bacteria include *Staphylococcus aureus*/methicillin-resistant *S. aureus, Neisseria meningitides, Mycobacterium tuberculosis, Borrelia* species, *Streptococcus Pneumoniae, Chlamydia Trachomatis, Neisseria Gonorrhoeae* and the like. One of skill will readily understand that this list is exemplary only and that other bacteria are well known to and can be readily identified by those of skill in the art. Exemplary fungi include *Candida* species, *Aspergillus* species, *Histoplasma capsulatum, Cryptococcus neoformans, Cryptococcus gattii, Coccidioides immitis* and the like. One of skill will readily understand that this list is exemplary only and that other fungi are well known to and can be readily identified by those of skill in the art.

"Kit" refers to any system, materials or reagents for carrying out a method of the present disclosure. In the context of method described herein, a kit for identifying a particular polymorphism within a population of particular organisms may include assays, reaction reagents (e.g., primers, enzymes, etc. in the appropriate containers) and/or supporting materials (e.g., buffers, written instructions for performing the assay etc.). For example, kits include one or more enclosures (e.g., boxes) containing the relevant reaction reagents and/or supporting materials for assays or methods of the invention. Such contents may be delivered to the intended recipient together or separately. For example, a first container may contain an enzyme for use in an assay, while a second container contains primers.

The terms "melting temperature," abbreviated $T_m$, refers to the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation. $T_m=81.5+0.41$ (% G+C), when a nucleic acid is in aqueous solution at 1 M NaCl (see e.g., Anderson and Young, "Quantitative Filter Hybridization," in *Nucleic Acid Hybridization* (1985). Other references (e.g., Allawi, U. T. & Santa Lucia, J., Jr., *Biochemistry* 36, 10581-94 (1997)) include alternative methods of computation which take structural and environmental, as well as sequence characteristics into account for the calculation of $T_m$. DNASoftware™ Visual OMP™ is a software for designing primers and probes that may be used to calculate $T_m$, e.g. assuming a concentration of monovalent ions of 0.1 M and a concentration of magnesium ions of 0.003 M. The melting temperature of a target amplicon is defined as the calculated melting temperature of an oligonucleotide spanning the entire amplicon—that is, the melting temperature of the complete product of amplification using flanking oligonucleotide primers.

Unless indicated otherwise, the terms apparatus, diagnostic apparatus, diagnostic system, diagnostic test, diagnostic test system, test unit, and variants thereof, can be interchangeably used.

In some embodiments, a method includes detecting the presence of a target bacteria or target pathogen (e.g., organism) and whether the target pathogen is resistant to a treatment regimen (e.g., a course of antibiotics) or susceptible to the treatment regimen via a single molecular diagnostic test operation (i.e., without the need for one or more follow-up or "reflex" tests). In some embodiments, when the presence of the target pathogen is detected, the method can include detecting the presence of either a first allele within the target organism associated with resistance to the treatment regimen or a second allele within the target organism associated with susceptibility to the treatment regimen. As described in detail herein, by testing for both the alleles using a probe for each allele, the method can minimize the likelihood of a false positive result that erroneously indicates resistance to the treatment while also maximizing the "true positive" rate for susceptibility. Specifically, when such methods are used to test for antimicrobial resistance (AMR), it is desirable that the results have a very low rate of false positive results (i.e., a high specificity) indicating susceptibility to treatment via an antibiotic, while also having a high rate of identifying when the target pathogen is susceptible to treatment via the antibiotic (e.g., a high sensitivity). Advantageously, the device has a low false positive rate at high concentrations of amplicon in the output solution of the amplification module, while also achieving a low false negative rate at low concentrations of amplicon in the output solution. Advantageously, the device has high sensitivity for susceptible organism at low concentrations—i.e. a low limit of detection. Advantageously, a weaker resistance probe decreases the limit of detection for susceptible organism and/or reduces the false positive rate of the device. Similarly stated, the dynamic range of the measurement is increased.

FIG. 1 is a schematic illustration of a method 10 of detecting a target organism and whether the target organism is susceptible to a treatment regimen or resistant to the treatment regimen using a combined test, according to an embodiment. The method 10 optionally includes first reading a test result associated with a positive control, at 11. The reading can be performed by any of the methods described herein, and can be performed, for example, by visually inspecting a detection surface or electronically reading a detection surface. The positive control result can be any signal (e.g., visual, electronic) that is produced when the sample preparation, amplification and detection of a positive control substance within the device is successful, and thus, when present, indicates a valid test. For example, in some embodiments, the positive control result can be a signal produced by a detection surface of any of the molecular diagnostic test devices described herein. The positive control substance can be a positive control organism (living or dead), a DNA, or any other substance that is included within the device and that undergoes any sample preparation, amplification and/or detection operations along with the biological sample. For example, in some embodiments, the positive control substance is a positive control organism, such as *Aliivibrio fischeri, N. subflava*, or any other suitable organism. Specifically, *Aliivibrio fischeri* is suitable because it is gram negative, nonpathogenic, bio safety level 1, not harmful to the environment, and is extremely unlikely to be found on a human. If the result indicates there is no positive control signal, at 12, then the test is invalid.

If, however, the result indicates that there is a positive control signal, the test is a valid test and the method includes reading a test result associated with detection of an amplicon indicating the presence of the target organism, at 13. The reading can be performed by any of the methods described herein, and can be performed, for example, by visually inspecting a detection surface or electronically reading a detection surface. The result can be any signal (e.g., visual, electronic) that is produced when the target amplicon is present, thus indicating the presence of the target organism in the biological sample. The target organism can be any organism of interest, and in some embodiments, can be *Neisseria gonorrhoeae* (NG). Although described as testing for a target organism, any of the devices and methods described herein can be used to detect any pathogen or organism (e.g., bacteria, virus, fungi, etc.). If the result indicates there is no amplicon associated with the target organism present, at 14, then the test is a negative result. As such, because the target organism is not present, no treatment regimen will be administered.

If, however, the result indicates that the amplicon associated with the target organism is present, then test is a positive result and a treatment regimen will be administered. To determine whether the strain of organism from the biological sample is resistant or susceptible to a treatment regimen, the method includes reading a test result associated with detection of a first allele within the target organism that is associated with resistance of the organism a treatment, at 15. The reading can be performed by any of the methods described herein, and can be performed, for example, by visually inspecting a detection surface or electronically reading a detection surface. The result can be any signal (e.g., visual, electronic) that is produced when the first allele is present, thus indicating that the organism is resistant to a treatment regimen. The first allele can be detected within the same amplicon produced and tested for the presence of the target organism or within a different amplicon produced by the test device. If the result indicates that the first allele is present, at 17, then the test is a positive result that indicates that the organism is resistant to the treatment regimen. In some embodiments, the target organism is NG and the first allele is associated with resistance of the NG to certain classes of antibiotics (including ciprotloxacin). Thus, if the result indicates that the first allele is present, the test will identify the NG strain as being resistant to treatment by ciprofloxacin. In such instances, the patient may receive an alternative course of treatment, for example, parenteral ceftriaxone (CRO) plus oral azithromycin (AZI). This alternative course of treatment with "last resort" antibiotics is currently the standard of care due to the increased amount of NG strains that are resistant to ciprofloxacin.

If, however, the result does not indicate the presence of the first allele, the method reading a test result associated with detection of a second allele within the target organism that is associated with susceptibility of the organism a treatment, at 16. By testing for the second allele, the method can reduce potential incidents of falsely identifying the organism as susceptible to the treatment when the test result at 15 does not clearly indicate the presence of the first allele. For example, if there is a low concentration of the resistant strain of the target organism, the test result for the first allele may not produce a signal (or a sufficient level of the signal for accurate detection). Thus, by testing for the second allele at 16, the specificity for detecting whether the target organism is resistant or susceptible to the treatment is improved. Testing for the second allele also allows the method to be accurate over a high dynamic range of concentration of the amplified product. The reading can be performed by any of the methods described herein, and can be performed, for example, by visually inspecting a detection surface or electronically reading a detection surface. The result can be any signal (e.g., visual, electronic) that is produced when the second allele is present, thus indicating that the organism is susceptible to the treatment regimen. The second allele can be detected within the same amplicon produced and tested for the presence of the target organism or the first allele, or within a different amplicon produced by the test device.

If the result indicates that the second allele is not present, then the test is a positive result that indicates that the organism is resistant to the treatment regimen, at 17. If however, the result indicates that the second allele is present, at 18, then the test is a positive result that indicates that the organism is susceptible to the treatment regimen. In some embodiments, the target organism is NG and the second allele is associated with susceptibility of the NG to certain classes of antibiotics (including ciprofloxacin). Thus, if the result indicates that the second allele is present, the test will identify the NG strain as being susceptible to treatment by ciprofloxacin. In some embodiments, the method 10 or any of the other methods described herein can include comparing a magnitude or intensity of the test results for the first allele and the second allele to accurately assess the presence of the first allele and/or the second allele.

The method 10 and any of the method described herein can be performed on any suitable molecular diagnostic test device, such as any of the diagnostic devices shown and described herein or in International Patent Publication No. WO2016/109691, entitled "Devices and Methods for Molecular Diagnostic Testing," International Patent Publication No. WO2017/185067, entitled "Printed Circuit Board Heater for an Amplification Module," International Patent Publication No. WO2018/005870, entitled "Devices and Methods for Detection of Molecules Using a Flow Cell," International Patent Application No. PCT/US17/40112, entitled "Devices and Methods for Nucleic Acid Extraction," and International Patent Publication No. WO2019/060117, entitled "Portable Molecular Diagnostic Test Device and Methods for the Detection of Target Viruses," each of which is incorporated herein by reference in its entirety.

Figure 2:
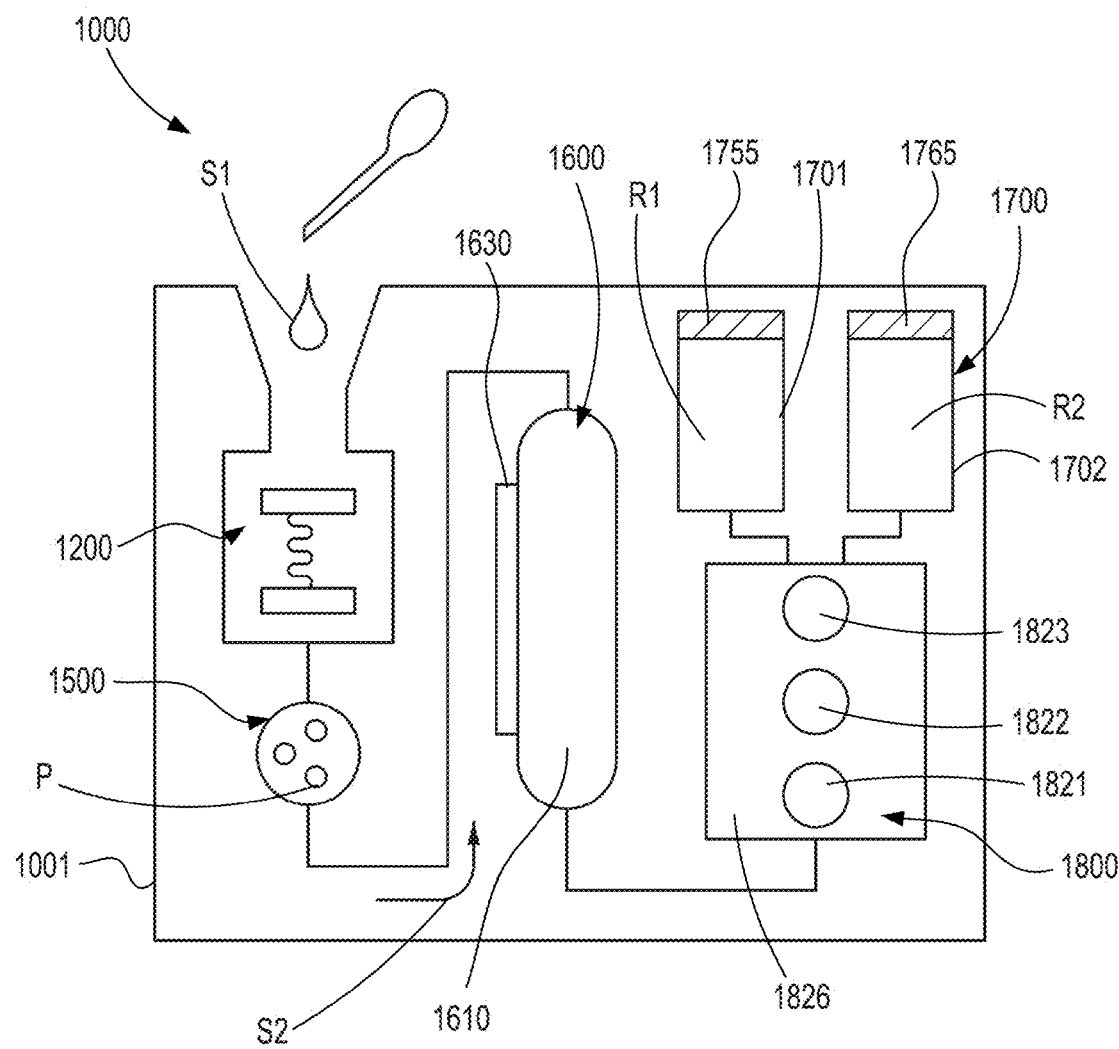
FIGS. 2-4 are schematic illustrations of a molecular diagnostic test device configured to detect a single nucleotide polymorphism (SNP), according to an embodiment, in a first configuration, a second configuration, and a third configuration, respectively.
Figure 3:
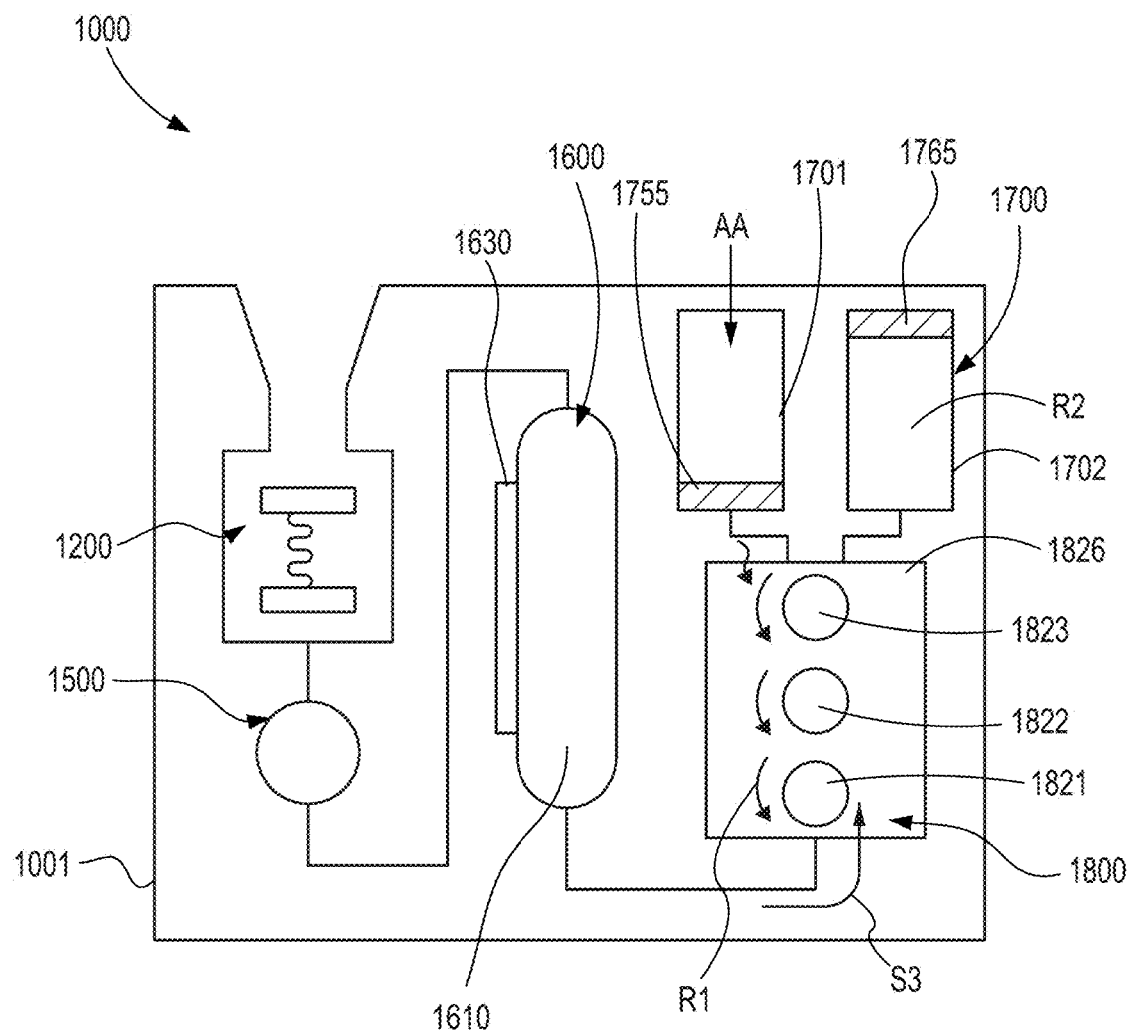
Figure 4:
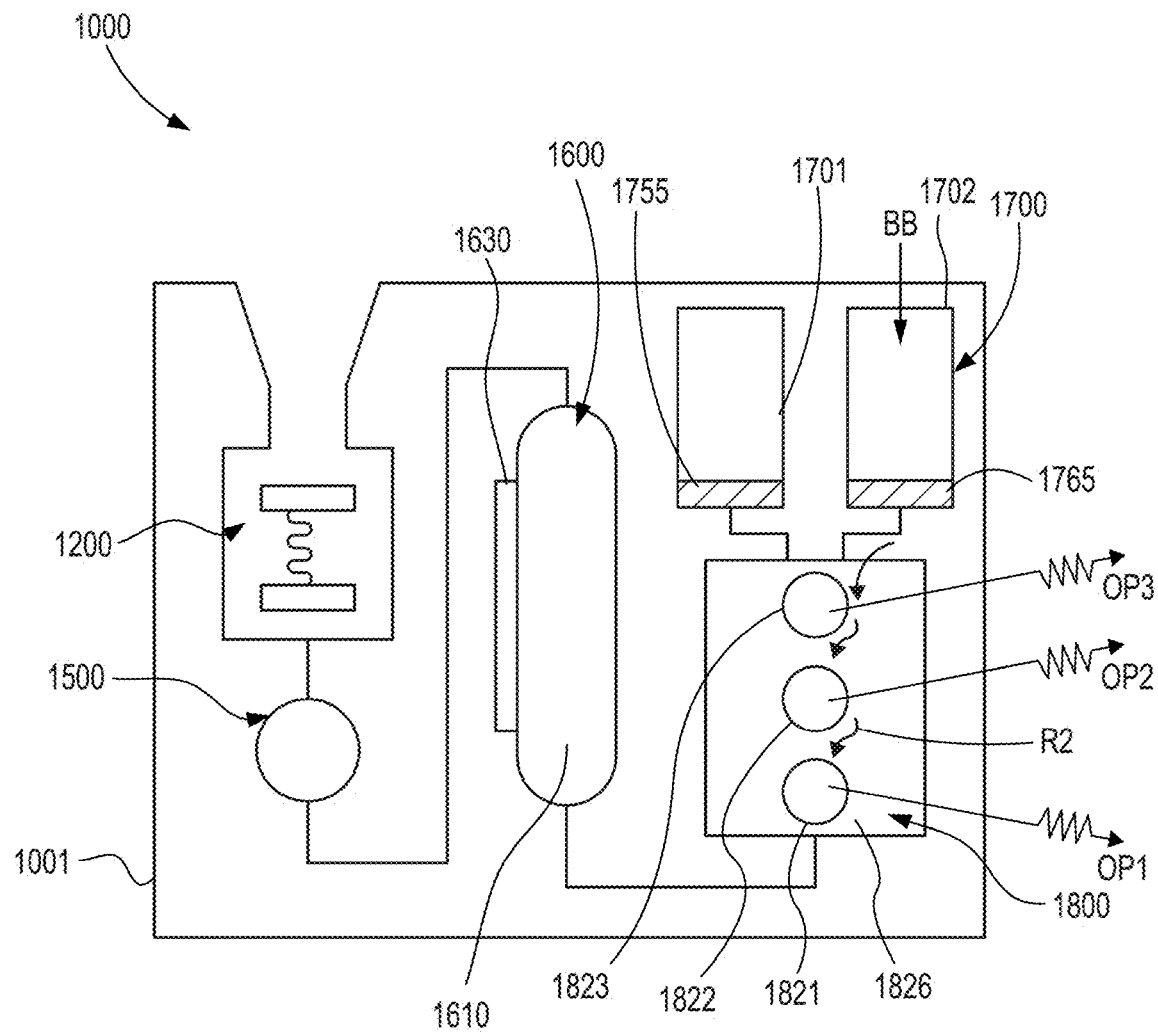

For example, any of the methods described herein can be performed using the molecular diagnostic test device 1000, which is shown schematically in FIGS. 2-4. The test device 1000 contains a primer set targeting at least a single nucleotide polymorphism (SNP) locus in the polynucleotide and is configured to manipulate a biological sample to produce one or more output signals associated with the SNP, according to any of the methods described herein. In some embodiments, the test device 1000 can be an integrated device that is suitable for use within a point-of-care setting (e.g., doctor's office, pharmacy or the like), decentralized test facility, or at the user's home. Similarly stated, in some embodiments, the modules of the device, described below, are contained within a single housing such that the test device can be fully operated without any additional instrument, docking station, or the like. Further, in some embodiments, the device 1000 can have a size, shape and/or weight such that the device 1000 can be carried, held, used and/or manipulated in a user's hands (i.e., it can be a "handheld" device). In some embodiments, the test device 1000 can be a self-contained, single-use device.

In some embodiments, the device 1000 (and any of the devices shown and described herein) can be a CLIA-waived device and/or can operate in accordance with methods that are CLIA waived. Similarly stated, in some embodiments, the device 1000 (and any of the other devices shown and described herein) is configured to be operated in a sufficiently simple manner and can produce results with sufficient accuracy to pose a limited likelihood of misuse and/or to pose a limited risk of harm if used improperly. In some embodiments, the device 1000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 1000 can be configured for long term storage in a manner that poses a limited likelihood of misuse (spoilage of the reagent(s), expiration of the reagents(s), leakage of the reagent(s), or the like). In some embodiments, the molecular diagnostic test device 1000 is configured to be stored for up to about 16 months, up to about 12 months, up to about 28 months, up to about 24 months, up to about 20 months, up to about 18 months, up to 12 months, up to 6 months, or any values there between.

The test device 1000 includes a housing 1001, a sample preparation module 1200 (also referred to as a sample staging module), an amplification reagent module 1500, an amplification module 1600, a detection reagent module 1700, and a detection module 1800. In some embodiments, the test device 1000 can include any other components or modules described herein, such as, for example, a valve (e.g., to control flow of reagents and/or sample, such as the valve 4340), a fluid transfer module (e.g., the fluid transfer module 4400), and/or an electronic control system (e.g., the electronic control system 4950). The housing 1001 can be any structure within which the sample preparation module 1200 or other components are contained (or partially contained) to form an integrated device for sample preparation and/or molecular testing.

Figure 8:
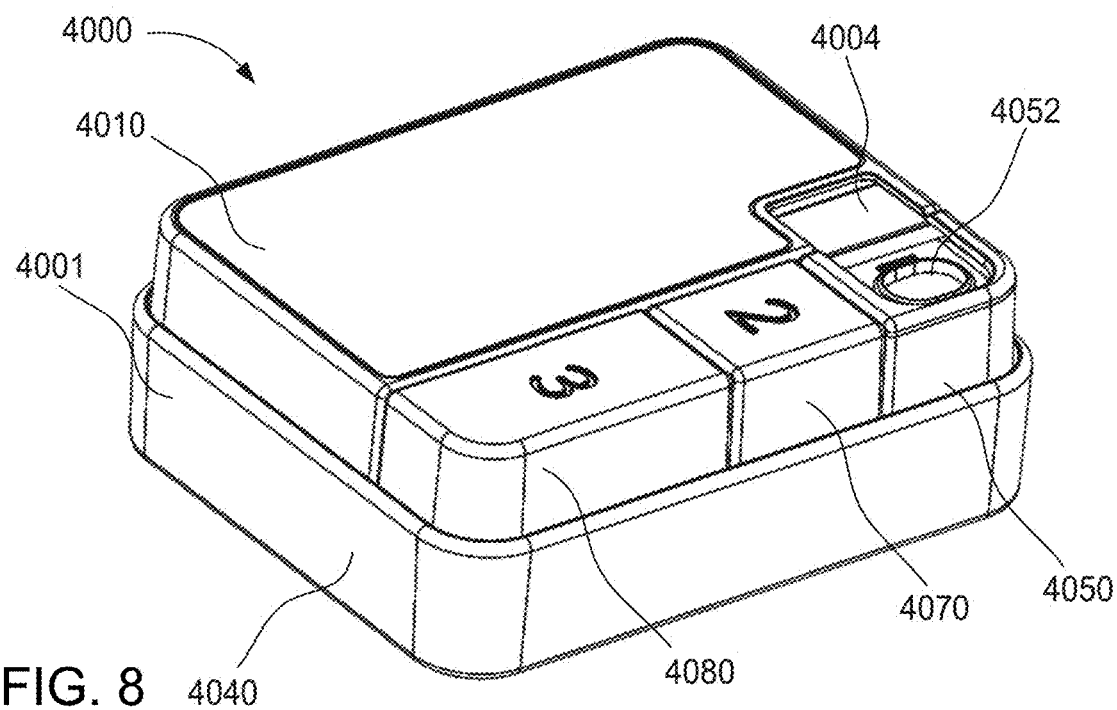
FIG. 8 is a perspective view of the molecular diagnostic test device shown in FIGS. 6 and 7, with the lid removed to show the sample input opening.
Figure 9:
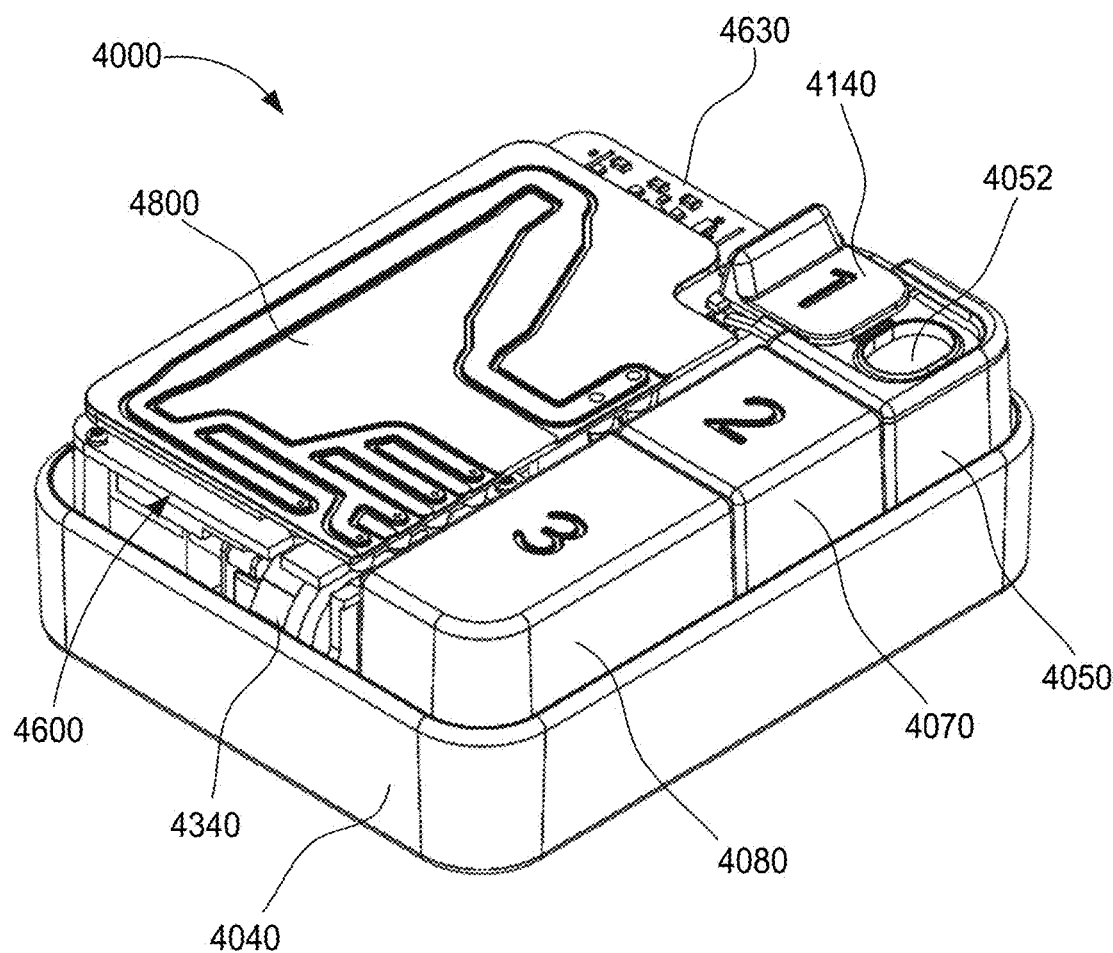
FIG. 9 is a perspective view of the molecular diagnostic test device shown in FIGS. 6 and 7, with the top portion of the housing removed to show the internal components.

The sample preparation module 1200 defines a sample input volume that receives a biological sample S1. The sample preparation module 1200 can include any components as described herein to manipulate the biological sample S1 for further diagnostic testing and/or to produce a solution for detection of a nucleic acid. For example, in some embodiments, the sample preparation module 1200 can include one or more heaters, one or more chambers within which the biological sample S1 can be manipulated, one or more mixing chambers, and/or certain on-board reagents (e.g., a lysing buffer, an RT enzyme, a control substance, or the like). In some embodiments, the sample preparation module 1200 is configured to extract nucleic acid molecules from the biological sample S1 and can produce, along with the amplification reagent module 1500, an input solution S2 (see FIG. 8) that is conveyed into the amplification module 1600.

The amplification reagent module 1500 is fluidically coupled to the sample preparation module 1200 and contains the desired amplification reagents to facilitate the desired amplification according to any of the methods described herein. As shown in FIG. 2, the amplification reagent module 1500 contains a primer set P targeting a single nucleotide polymorphism (SNP) locus in a polynucleotide of the biological sample S1. The SNP primer set P can include any of the SNP primer sets shown and described herein. The primer set P targets the SNP locus (e.g., by flanking the SNP locus). In some embodiments, the primer set P can also target a locus in a polynucleotide associated with a target organism. Thus, in some embodiments, the device (and methods using the device) can produce one amplicon through which the presence of the organism and whether the organism is resistant or susceptible to a treatment can be detected. In other embodiments, the device (and methods using the device) can produce two or more amplicons through which the presence of the organism and whether the organism is resistant or susceptible to a treatment can be detected. In addition to the SNP primer set P, the amplification reagent module 1500 can include any other suitable amplification reagents, such as additional primers, nucleotides (e.g., dNTPs), and the DNA polymerase. In RT-PCR applications (e.g., for viral pathogens), the amplification reagent module 1500 may contain a reverse transcriptase. Because the device 1000 is configured for single-use in a point-of-care setting, the amplification reagents can be formulated for and/or packaged within the amplification reagent module 1500 to enhance long term storage. Accordingly, in some embodiments, the SNP primer set P and other amplification reagents can be formulated to have a shelf life of up to about 36 months, up to about 32 months, up to about 26 months, up to about 24 months, up to about 20 months, up to about 18 months, or any values therebetween. For example, in some embodiments, the SNP primer set P can be in the form of a lyophilized pellet or bead.

In some embodiments, the amplification reagent module 1500 can be fluidically coupled to and can convey the SNP primer set P into the sample preparation module 1200 (e.g., for mixing, reconstitution, etc.). In other embodiments, the amplification reagent module 1500 can be configured to receive an output from the sample preparation module 1200 and mix the output with the SNP primer set P and other amplification reagents. In such embodiments, the amplification reagent module 1500 can be configured to hydrate and/or reconstitute the lyophilized beads in a given input volume, while ensuring even local concentrations of reagents in the entirety of the volume. The amplification reagent module 1500 can include any suitable mechanism for producing the desired solution, such as, for example, a continuous flow mixing channel, an active mixing element (e.g., a stir rod) and/or a vibratory mixing element. The mixed sample (referred to as an amplification solution S2) is then conveyed to the amplification module 1600.

The amplification module 1600 includes a flow member 1610 and a heater 1630. The flow member (which functions as a reaction volume) 1610 can be any suitable structure that defines a volume or a series of volumes within which the amplification solution S2 can flow and/or be maintained to amplify the target nucleic acid molecules therein to produce an output detection solution S3 that contains a target amplicon (or multiple target amplicons) to be detected. The heater 1630 can be any suitable heater or group of heaters coupled to the flow member 1610 that can heat the amplification solution S2 within the flow member 1610 to perform any of the amplification operations as described herein. For example, in some embodiments, the amplification module 1600 (or any of the amplification modules described herein) can be similar to the amplification modules shown and described in U.S. Patent Publication No. 2017/0304829, entitled "Printed Circuit Board 7Heater for an Amplification Module," which is incorporated herein by reference in its entirety. In other embodiments, the amplification module 1600 (or any of the amplification modules described herein) can be similar to the amplification modules shown and described in International Patent Publication No. WO2016/109691, entitled "Devices and Methods for Molecular Diagnostic Testing," which is incorporated herein by reference in its entirety.

In some embodiments, the flow member 1610 defines a single volume within which the amplification solution S2 is maintained and heated to amplify the nucleic acid molecules thereby producing the detection solution S2. In other embodiments, the flow member 1610 can define a "switchback" or serpentine flow path through which the amplification solution S2 flows. Similarly stated, in some embodiments, the flow member 1610 defines a flow path that is curved such that the flow path intersects the heater 1630 at multiple locations. In this manner, the amplification module 1600 can perform a "flow through" amplification reaction where the amplification solution S2 flows through multiple different temperature regions.

The heater 1630 can be any suitable heater or collection of heaters that can perform the functions described herein to amplify the prepared solution. In some embodiments, the heater 1630 can establish multiple temperature zones through which the prepared solution flows and/or can define a desired number of amplification cycles to ensure the desired test sensitivity (e.g., at least 30 cycles, at least 34 cycles, at least 36 cycles, at least 38 cycles, or at least 40 cycles). The heater 1630 (and any of the heaters described herein) can be of any suitable design. For example, in some embodiments, the heater 1630 can be a resistance heater, a thermoelectric device (e.g. a Peltier device), or the like. In some embodiments, the heater 1630 can be one or more linear "strip heaters" arranged such that the flow path crosses the heaters at multiple different points. In other embodiments, the heater 1630 can be one or more curved heaters having a geometry that corresponds to that of the flow member 1610 to produce multiple different temperature zones in the flow path.

Although the amplification module 1600 is generally described as performing a thermal cycling operation on the amplification solution S2, in other embodiments, the amplification module 1600 (and any of the amplification modules described herein) can perform any suitable thermal reaction to amplify nucleic acids within the solution. In some embodiments, the amplification module 1600 (and any of the amplification modules described herein) can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process.

The detection reagent module 1700 is disposed within the housing 1001 and includes a first reagent container 1701, a first reagent actuator 1755, a second reagent container 1702, and a second reagent actuator 1765. The detection reagent module 1700 provides on-board storage of a first reagent R1 (within the first reagent container 1701) and a second reagent R2 (within the second reagent container 1702) used in connection with the molecular diagnostic tests described herein. In some embodiments, the first reagent R1 is sealed within the first reagent container 1701 and the second reagent R2 is sealed within the second reagent container 1702. In some embodiments, the detection reagent module 1700 can include one or more puncturers that, upon device actuation, can release the reagents for use. The first reagent R1 is a detection reagent formulated to facilitate production of a signal that indicates a presence of a target amplicon (e.g., from the amplified solution S3). In some embodiments, the first reagent R1 comprises streptavidin-tagged horse radish peroxidase (HRP) of the compositions shown and described herein. The second reagent R2 is a substrate formulated to produce an output signal (e.g., OP1, OP2, OP3) when catalyzed by the first reagent R1. For example, in some embodiments, the second reagent R2 can be a substrate (e.g., a precipitating substrate) of the types shown and described herein.

The detection module 1800 is configured to react the amplified solution S3 from the amplification module 1600 with the first reagent R1 and the second reagent R2 to produce one or more signals (or outputs) OP1, OP2, OP3 to indicate presence or absence of a target organism, the presence or absence of a first target allele at a SNP locus in the genome of a target organism in the biological sample S1, and/or the presence or absence of a second target allele at the SNP locus in the genome of the target organism. Specifically, the detection module 1800 defines a detection channel and includes a first detection surface 1821, a second detection surface 1822, and a third detection surface 1823 within the detection channel. The first detection surface 1821 includes a first probe adhered thereto and that is designed to permit annealing or hybridization of a target amplicon with sufficient specificity to permit detection of the presence (or absence) of a target amplicon indicating the presence of the target organism. Similarly stated, the first probe is designed to bind to a first genetic locus in a polynucleotide associated with the target organism. The second detection surface 1822 includes a second probe adhered thereto and designed to permit annealing or hybridization or a target amplicon with sufficient specificity to permit detection of the presence (or absence) of a target amplicon if a first allele is present (or absent) in an allele-specific manner. The first allele is associated with resistance of the target organism to a treatment (e.g., an antibiotic). Similarly stated, the second probe is designed to bind to a second genetic locus if the second genetic locus comprises the first target allele associated with resistance of the target organism to a treatment. The third detection surface 1823 includes a third probe adhered thereto and designed to permit annealing or hybridization of a target amplicon with sufficient specificity to permit detection of the presence (or absence) of a target amplicon if a second allele is present (or absent) in an allele-specific manner. The second allele is associated with susceptibility of the target organism to a treatment (e.g., an antibiotic). Similarly stated, the third probe is designed to bind to the second genetic locus if the second genetic locus comprises the second target allele associated with susceptibility of the target organism to a treatment. In some embodiments, the second genetic locus is associated with a single nucleotide polymorphism (SNP) locus in the polynucleotide.

The first probe, the second probe, and the third probe can be any of the detection probes described herein. In some embodiments, the second probe and the third probe have about the affinity for the amplicon comprising their respective alleles. Unless otherwise clear from context, the melting temperature ($T_m$) of a probe refers the melting temperature of the probe when the allele it is designed or configured to detect is present in the target amplicon—the $T_m$ of the second probe is therefore defined with respect to an amplicon comprising the first allele; the $T_m$ of the third probe is defined with respect to an amplicon comprising the second allele. In some embodiments, the second probe and third probe are symmetrical—that is, they anneal to the amplicon if their respective allele is present at about the same or the same $T_m$. In some embodiments employing symmetric probes, the device is configured to generate a result based on the relative intensity of the respective signals.

In some embodiments, the second probe is designed to maximize binding to the wild type, ciprofloxacin-sensitive gyrA Ser-91 genotype while minimizing binding to other SNPs at a gyrA Ser-91 site that confers a drug resistance.

In some embodiments, the second probe is substantially complementary to a probe binding site comprising the codon encoding gyrA Ser-91, and wherein the second probe comprises a nucleotide that matches an allele encoding ciprofloxacin-sensitive gyrA Ser-91 genotype.

In some embodiments, the second probe discriminates between an allele encoding the ciprofloxacin-sensitive gyrA Ser-91 genotype and the antiallele encoding the gyrA Ser-91 site that confers resistance to ciprofloxacin.

As used here, the term "discriminates" refers to the ability or capacity of a device to determine the presence of a particular SNP of interest within an amplified region of sequence. For example, the device may produce an intensity of signal from the SNP-specific capture probe that indicates the presence of the target allele at the SNP locus in the target amplicon (or other polynucleotide) introduced into the detection module (whether the target amplicon is produced on a device having both amplification and detection module; supplied to a device having a detection module but no amplification module; or transferred from a device having an amplification module to a device having a detection module). In some embodiments, the signal (e.g., a colorimetric change) produced by the device at test spot (e.g., detection surface detection surface 4821) having the capture probe is compared to the signal produced by the same or equivalent device when the target amplicon (or other polynucleotide) lacking the target allele at the SNP locus is provided to the detection module. Stated differently, response criteria can be set by standardization of signal intensity from similarly manufactured devices. The control probe is an optimal feature of the device. In some embodiments, the signal produced by the device from the test spot is compared to the signal produced by the device at a control spot (e.g., a detection surface 4821) having a control capture probe. For example, the device may be engineered or calibrated to produce a similar or substantially equal signal at the two detection surfaces (capture probe and control capture probe) as an indicator for presence of the target allele; and to produce a reduced signal from the capture probe, compared to the control capture probe, where the target amplicon (or other polynucleotide) lacks the target allele at the SNP locus. Stated different, the signal from the two detection surfaces may be similar or substantially equal when the biological sample comprising a polynucleotide from a drug-sensitive (or drug-resistant) pathogen (e.g. an antibiotic-sensitive organism); and different when the biological sample comprising a polynucleotide from a drug-resistant (or drug-sensitive) pathogen (e.g. an antibiotic-resistant organism). Thus, in some embodiments of the devices and methods of the disclosure, the device produces a test signal in response to a test polynucleotide that differs sufficiently in comparison from the reference signal produced in response to a reference polynucleotide so that the test signal and be distinguished from the reference signal, permitting an instrument or user to distinguish between a test polynucleotide have a characteristic (e.g., presence of an allele) and a test polynucleotide not having that characteristic (e.g., absence of an allele). Without being bound by theory, the control probe may serve, in some embodiments, one or more of at least three roles: 1) to assure that the target (e.g., gyrA) amplicon was in fact generated by the device; 2) to permit a user (or the device itself) to compare signal intensity between the SNP-specific capture probe and the control capture probe in order to make a call: of "SNP present" or "SNP absent"; and 3) to serve to detection the presence of an organism (regardless of presence of absence of the SNP) (e.g., when the user does not intend to determine drug resistance but merely wishes to employ the device for detection of the pathogen).

In some embodiments, the first probe has a melting temperature of about 52° C. In some embodiments, the first probe has a melting temperature of about 55° C. In some embodiments, the first probe has a melting temperature of about 58° C. In some embodiments, the first probe has a melting temperature of about 60° C. In some embodiments, the first probe has a melting temperature of about 62° C. In some embodiments, the first probe has a melting temperature of about 65° C. In some embodiments, the first probe has a melting temperature of about 67° C. In some embodiments, the first probe has a melting temperature between about 35° C. and about 45° C. In some embodiments, the first probe has a melting temperature between about 45° C. and about 55° C. In some embodiments, the first probe comprises between 12 and 25 nucleotides. In some embodiments, the first probe comprises between 18 and 22 nucleotides. In some embodiments, the first probe comprises between 22 and 28 nucleotides. In some embodiments, the first probe comprises between 25 and 30 nucleotides. In some embodiments, the first probe comprises between 27 and 35 nucleotides. In some embodiments, the first probe comprises 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

In some embodiments, the second probe has a melting temperature of about 52° C. In some embodiments, the second probe has a melting temperature of about 55° C. In some embodiments, the second probe has a melting temperature of about 58° C. In some embodiments, the second probe has a melting temperature of about 60° C. In some embodiments, the second probe has a melting temperature between about 35° C. and about 45° C. In some embodiments, the second probe has a melting temperature between about 45° C. and about 55° C. In some embodiments, the second probe comprises between 12 and 25 nucleotides. In some embodiments, the second probe comprises between 18 and 22 nucleotides.

In some embodiments, the third probe has a melting temperature of about 52° C. In some embodiments, the third probe has a melting temperature of about 55° C. In some embodiments, the third probe has a melting temperature of about 58° C. In some embodiments, the third probe has a melting temperature of about 60° C. In some embodiments, the third probe has a melting temperature between about 35° C. and about 45° C. In some embodiments, the third probe has a melting temperature between about 45° C. and about 55° C. In some embodiments, the third probe comprises between 12 and 25 nucleotides. In some embodiments, the third probe comprises between 18 and 22 nucleotides.

In some embodiments, the second probe and the third probe may be asymmetrical. The term asymmetrical, as used herein, refers to a pair of probes having different $T_m$'s for their respective alleles. In some embodiments, the $T_m$'s of asymmetrical probes are at least 1%, 2%, 3%, 4%, 5%, 6%, 7%, 8%, 9%, or 10% higher (or lower) than each other. In some embodiments, the $T_m$'s of asymmetrical probes are at least 1° C., 2° C., 3° C., 4° C., 5° C., 6° C., 7° C., 8° C., 9° C., or 10° C. higher (or lower) than each other. In some embodiments, the $T_m$'s of asymmetrical probes are at least 11° C., 12° C., 13° C., 14° C., 15° C., 16° C., 17° C., 18° C., 19° C., or 20° C. higher (or lower) than each other. In some embodiments, the $T_m$'s of asymmetrical probes are at least 21° C., 22° C., 23° C., 24° C., 25° C., 26° C., 27° C., 28° C., 29° C., or 30° C. higher (or lower) than each other.

In certain embodiments, the $T_m$ of the second probe (for resistance) is at least 1%, 2%, 3%, 4%, 5%, 6%, 7%, 8%, 9%, or 10% lower than the $T_m$ of the third probe (for susceptibility). In some embodiments, the $T_m$ of the second probe (for resistance) is at least 1° C., 2° C., 3° C., 4° C., 5° C., 6° C., 7° C., 8° C., 9° C., or 10° C. lower than the $T_m$ of the third probe (for susceptibility). In some embodiments, the $T_m$ of the second probe (for resistance) is at least 11° C., 12° C., 13° C., 14° C., 15° C., 16° C., 17° C., 18° C., 19° C., or 30° C. lower than the $T_m$ of the third probe (for susceptibility). In some embodiments, the $T_m$ of the second probe (for resistance) is at least 21° C., 22° C., 23° C., 24°

C., 25° C., 26° C., 27° C., 28° C., 29° C., or 30° C. lower than the $T_m$ of the third probe (for susceptibility).

Advantageously, the use of a first probe, second probe, and third probe in conjunction with an algorithm such as disclosed in FIG. 1 permits determination of a treatment plan with high sensitivity and specificity at both low and high output concentrations. In some embodiments, at low output concentrations, the first probe specifically detects presence of the organism (e.g. NG) but not a reference organism (e.g. NS); the second probe (with lower $T_m$ than the third probe) specifically detects an amplicon only from a resistant organism or yields a negative result; and the third probe (with higher $T_m$ than the second probe) specifically detects an amplicon only from a susceptible organism or yields a negative result. A false negative from the third probe instructs the medical provider to administer stronger drug to patient infected with organism susceptible to the weaker drug. The patient is not harmed because the organism is susceptible to the stronger drug. At high output concentrations, the weak second probe (having lower $T_m$ than the third probe) yields no signal for a susceptible organism or signal for a resistance organism; the stronger third probe (having higher $T_m$ than the second probe) yields a signal for either susceptible organism or resistant organism. The patient is administered the weak drug only if the signal from the second probe is absent or weaker than the third probe by a predetermined amount. The table below summarizes drug administration in such embodiments.

The detection module 1800 also includes non-detection surfaces 1826 that are adjacent to, surround, or contact either or both of the first detection surface 1821 and the second detection surface 1822. The non-detection surfaces 1826 can provide a background region that can enhance the overall accuracy detection of the output signals from the device 1000. Although the first detection surface 1821, the second detection surface 1822, and the third detection surface 1823 are shown and described as having defined positions within the detection module 1800, in other embodiments, a detection module can include any number of detection surfaces in any desired order or spatial position within the module. Similarly stated, in other embodiments, the first detection surface 1821, the second detection surface 1822, and the third detection surface 1823 can be configured to permit detection of the presence or absence of any of the target amplicons as described herein. Moreover, in some embodiments, the detection module 1800 can include additional detection surfaces for controls, additional targets, or the like.

The detection channel is in (or can be placed in) fluid communication with each of the amplification module 1600 and the detection reagent module 1700. In this manner, the amplification solution S3 containing the target amplicon can be conveyed into the detection channel and across the detection surfaces 1821, 1822, 1823. Additionally, as shown in FIG. 3, the first reagent R1 can also be conveyed into the detection channel and across the detection surfaces 1821, 1822, 1823. The detection surfaces 1821, 1822, 1823 include a series of capture probes to which the target amplicon can be bound when the amplification solution S3 flows across the detection surfaces 1821, 1822, 1823. The probes can be any suitable probe of the types described herein, e.g., formulated to capture or bind to the target amplicon. The first reagent R1 can be conveyed by moving the first reagent actuator 1755 as shown by the arrow AA. The first reagent can flow across the detection surfaces, as shown. When the first reagent R1 (i.e., detection reagent) is conveyed into the detection channel, it binds to the captured amplicons. Specifically, the first reagent R1 can bind to the amplicon on the first detection surface 1821 that is captured by the first probe, the amplicon on the second detection surface 1822 that is captured by the second probe, and the amplicon on the third detection surface 1823 that is captured by the third probe.

In some embodiments, the detection module 1700 includes a heater (not shown in FIGS. 2-4) configured to incubate the detection reagent R1 within the detection channel in the presence of the captured amplicon to facilitate binding. In some embodiments, the heater can be controlled to maintain the temperature of the detection module 1700 to within about 5° C. of the melting temperature of the capture probe. In other embodiments, the heater can be controlled to maintain the temperature of the detection module 1700 to within about 10° C. or about 15° C. of the melting temperature of the capture probe. In this manner, detection of an allele at a SNP locus can be achieved with sufficient sensitivity and specificity to permit testing and therapeutic intervention at the point-of-care. The present inventors have determined that computational prediction of melting temperature, while a guide to probe design, is not alone sufficient to accurately determine the optimal probe design. Without being bound by theory, it is believed that melting temperature calculations assume polynucleotides interacting in solution, whereas here the probe is linked to the surface of the detection module. Experimental screening of candidate probes is required to achieve the desired operation characteristics. Illustrative methods for such screening are provided in the examples of the present disclosure. In particular, microtiter plate assays can be used to select and optimize probe design prior to construction of a molecular diagnostic device according to the present disclosure.

The second reagent R2 can be conveyed by moving the second reagent actuator 1765 as shown by the arrow BB. When the second reagent R2 reacts with captured amplicon(s) and the bound detection reagent, the first signal OP1 is produced from the first detection surface 1821, the second signal OP2 is produced from the second detection surface 1822, and/or the third signal OP3 is produced from the third detection surface 1823. In some embodiments, the second reagent R2 can be a substrate of the types shown and described herein that is formulated produce a first color product from the first detection surface 1821, a second color product from the second detection surface 1822, and the third color product from the third detection surface 1823. Similarly stated, in some embodiments, the first signal OP1, the second signal OP2, and the third signal OP3 can be colorimetric signals produced from their respective detection surface. The first color product, the second color product, and the third color product can be the same color or, in other embodiments, can be different colors.

The results produced by the device 1000 (i.e., the first signal OP1, the second signal OP2, and/or the third signal OP3) can be read and/or interpreted in any suitable manner. For example, in some embodiments, the detection module is positioned within the housing 1001 such that the first color product, the second color product, and the third color product are viewable via a detection opening (not shown) of the housing 1001. In such embodiments, the housing 1001 can include a key or legend to identify the various combinations of signals and the treatment regimen associated therewith. In other embodiments, the device 1000 (and any of the devices described herein) can include an electronic system that includes a digital read module implemented in at least one of a memory or a processing device. The digital read module can include a sensor that detects the presence of the signals (e.g., whether there is sufficient color product present to indicate a positive result) and produces a digital output (i.e., a YES/NO output) for the user. The digital output can be any one of a light output, an audible output, a wireless signal, or a haptic output, or a combination of these output forms.

Although not shown in FIG. 2-4, in some embodiments, the detection reagent module 1700 can contain any other suitable reagents to facilitate detection of the target SNP according to any of the methods described herein. For example, in some embodiments, the detection reagent module 1700 can include a wash solution comprises one or more buffers, ionic compounds, excipients, detergents, preservatives, or blocking reagents. In some embodiments, the wash solution can be conveyed into the detection channel to remove unbound PCR products and/or any remaining solution. In some embodiments, the wash buffer comprises phosphate buffered saline (PBS), potassium chloride (KCl), magnesium chloride ($MgCl_2$), PROCLIN300™, and/or polysorbate 20 (TWEEN® 20). Optionally, the wash buffer further comprises a blocking agent (e.g., bovine serum albumin (BSA). In certain embodiments, the wash buffer comprises about 0.5×, about 1.0×, or about 1.5×PBS, where 1.0×PBS has a final concentration of 137 mM NaCl, 10 mM Phosphate, 2.7 mM KCl, and a pH of about 7.4. In some embodiments, the wash buffer comprises (in addition to any KCl in the PBS) about 50 mM, about 60 mM, about 70 mM, about 80 mM, about 90 mM, about 100 mM, about 110 mM, or about 120 mM KCl. In some embodiments, the wash buffer comprises (in addition to any KCl in the PBS) about 60 mM to about 90 mM, about 70 mM to about 80 nM, or about 75 mM KCl. In some embodiments, the wash buffer comprises about 0.5 mM to about 10 mM $MgCl_2$, about 1 mM to about 7.5 mM $MgCl_2$, about 1 mM to about 5 mM $MgCl_2$, about 1 mM to about 4 mM $MgCl_2$, about 1 mM to about 3 mM $MgCl_2$, or about about 1 mM to about 2 mM $MgCl_2$. In some embodiments, the wash buffer comprises about 1 mM, about 1.5 mM, about 2 mM, about 2.5 mM about 3 mM, about 3.5 mM, or about 4.0 mM $MgCl_2$. In certain embodiments, the wash buffer comprises 1×PBS, about 70 mM to about 80 mM KCl, about 1 mM to about 3 mM $MgCl_2$, about 0.01% (v/v) to about 0.5% (v/v) polysorbate 20 at a pH of about 7.0 to about 7.5 (or pH about 7.4), and optionally a preservative (e.g. 0.03% (v/v) PROCLIN300™). Without limiting the disclosure to any particular wash buffer, the present inventors have surprisingly discovered that in some cases the wash buffers of the disclosure provide increased sensitivity and/or specificity for the apparatuses and methods of the disclosure.

Figure 5:
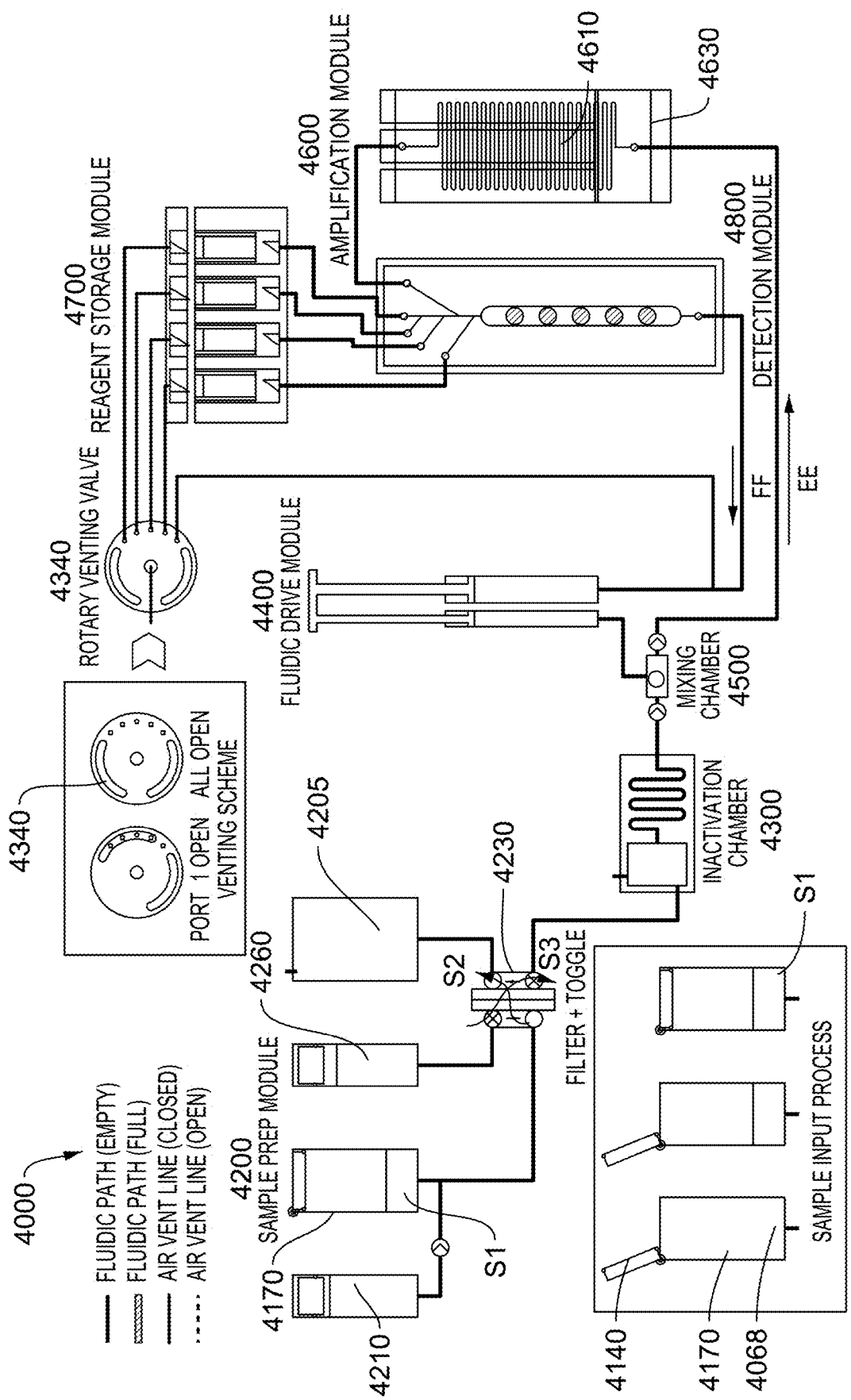
FIG. 5 is a schematic illustration of a molecular diagnostic test device, according to an embodiment.

FIG. 5 is a schematic illustration of a molecular diagnostic test device 4000 (also referred to as a "test device" or "device"), according to an embodiment. The schematic illustration describes the primary components of the test device 4000 as shown in FIGS. 6-13. The test device 4000 is an integrated device (i.e., the modules are contained within a single housing) that is suitable for use within a point-of-care setting (e.g., doctor's office, pharmacy or the like), decentralized test facility, or at the user's home. In some embodiments, the device 4000 can have a size, shape and/or weight such that the device 4000 can be carried, held, used and/or manipulated in a user's hands (i.e., it can be a "handheld" device). In other embodiments, the test device 4000 can be a self-contained, single-use device. In some embodiments, the test device 4000 can be configured with lock-outs or other mechanisms to prevent re-use or attempts to re-use the device.

Further, in some embodiments, the device 4000 can be a CLIA-waived device and/or can operate in accordance with methods that are CLIA waived. Similarly stated, in some embodiments, the device 4000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 4000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 4000 can be configured for long term storage in a manner that poses a limited likelihood of misuse (spoilage of the reagent(s), expiration of the reagents(s), leakage of the reagent(s), or the like). In some embodiments, the molecular diagnostic test device 4000 is configured to be stored for up to about 36 months, up to about 32 months, up to about 26 months, up to about 24 months, up to about 20 months, up to about 48 months, or any values there between.

The test device 4000 is configured to manipulate a biological sample S1 to produce one or more output signals associated with one or more target amplicons (e.g., an amplicon to detect the presence of a target organism, an amplicon associated with a target SNP), and can be used to perform any of the molecular diagnostic methods described herein. Specifically, the device 4000 includes a sample preparation module 4200, an inactivation module 4300 (also referred to as a lysing module), a fluidic drive (or fluid transfer) module 4400, a mixing chamber (which functions as an amplification reagent module) 4500, an amplification module 4600, a detection module 4800 and an electronic system (also referred to as a power and control module; not shown). The test device and certain components therein can be similar to any of the molecular test devices shown and described herein or in International Patent Publication No. WO2016/109691, entitled "Devices and Methods for Molecular Diagnostic Testing," which is incorporated herein by reference in its entirety. Accordingly, a detailed description of certain modules (e.g., the fluidic drive module 4400) is not provided herein.

Figure 6:
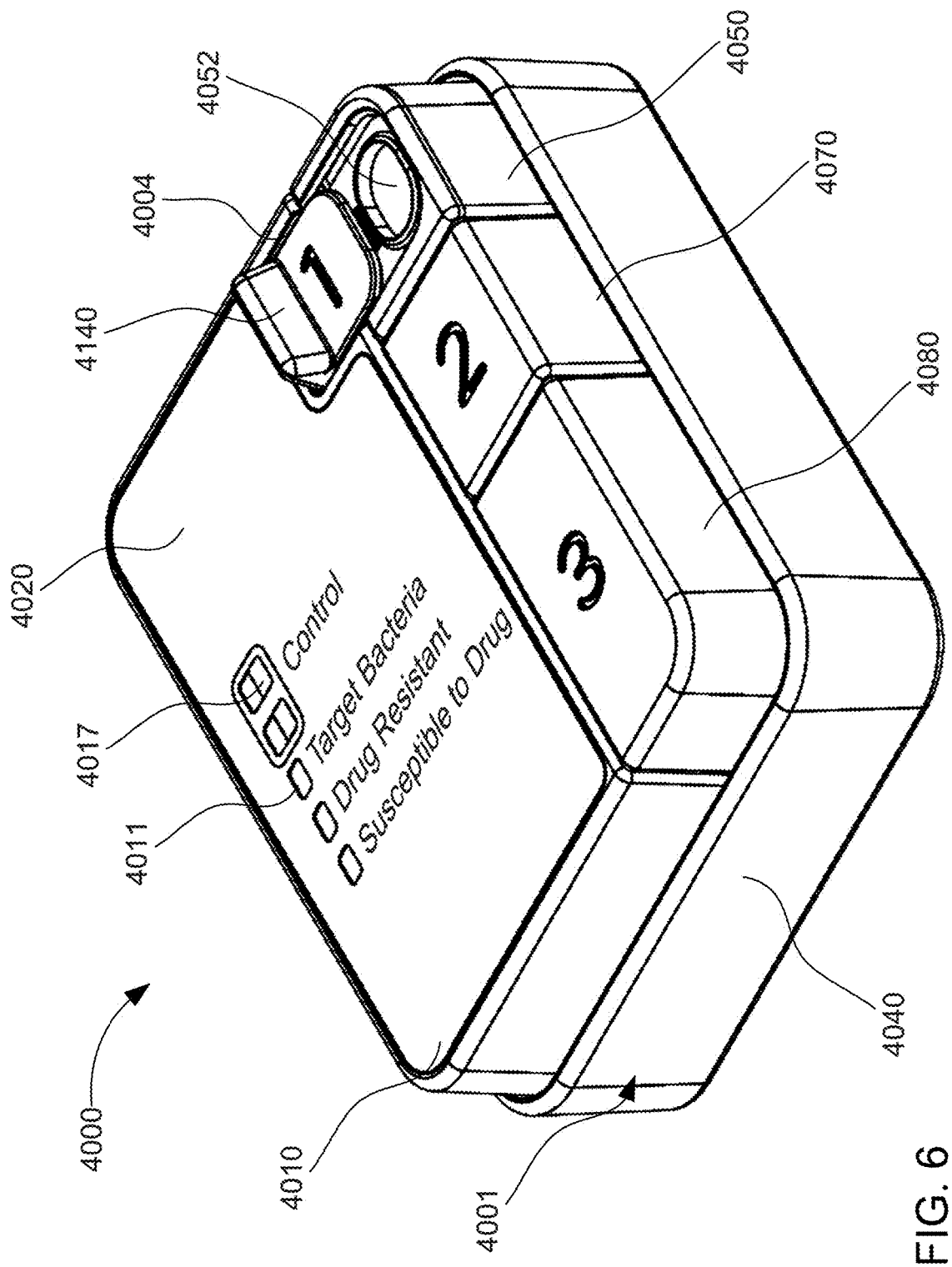
FIGS. 6 and 7 are a perspective view and a top view, respectively, of a molecular diagnostic test device, according to an embodiment.
Figure 7:
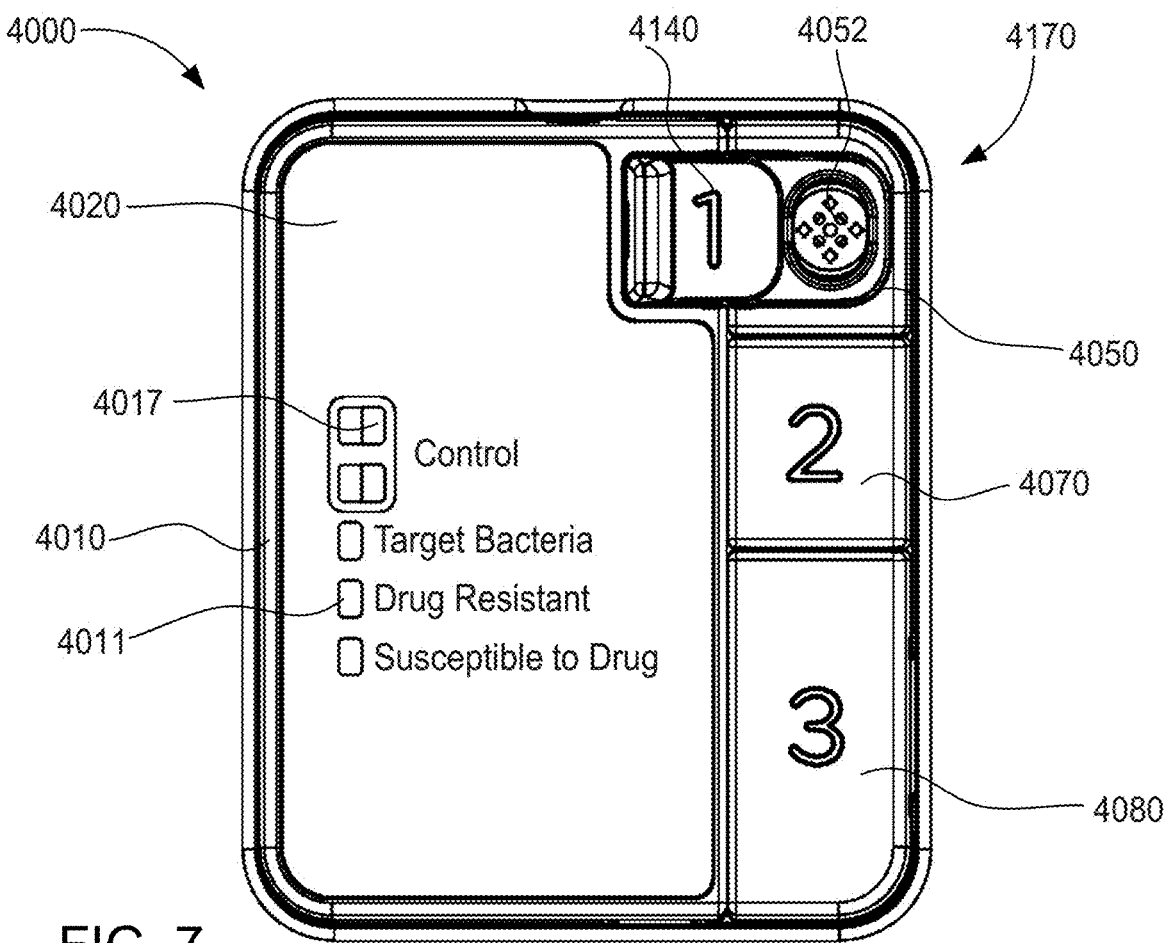

The diagnostic test device 4000 includes a housing 4001 (including a top portion 4010 and a bottom portion 4030), within which the modules described herein are fully or partially contained. Similarly stated, the housing 4001 (including the top portion 4010 and/or the bottom portion 4030) at least partially surround and/or enclose the modules. As shown in FIGS. 5-7, the device 4000 includes a sample input module 4170, a sample preparation module 4200, an inactivation module 4300, a fluidic drive (or fluid transfer) module 4400, an amplification reagent Module 4500 (see FIG. 5), an amplification module 4600, a detection module 4800, a reagent storage module 4700, a rotary venting valve 4340, and an electronic system 4950. In some embodiments, the sample preparation module 4200 can be considered as including the sample input module 4170 and/or the inactivation (also referred to as the lysing) module 4300, but in other embodiments, these modules can be considered as distinct from the sample preparation module 4200. In some embodiments, the sample preparation module 4200 can be considered as including the amplification reagent (or mixing) module 4500.

The housing assembly 4001 includes the top housing 4010, the bottom housing 4040, the vertical manifold 4035, and the sample transfer manifold 4100. As shown, the top housing 4010 includes a label 4020 that defines a series of detection openings (or windows) 4011 via which the device can be read. In some embodiments, the detection openings 4011 are aligned with the detection module 4800. In this manner, the signals produced by and/or on each detection surface of the detection module 4800 are visible through the appropriate detection opening 4011. In some embodiments, the top housing 4010 and/or the label 4020 is opaque (or semi-opaque), thereby "framing" or accentuating the detection openings. In some embodiments, for example, the top housing 4010 can include markings 4017 (e.g., thick lines, colors or the like) to highlight the detection opening 4011. In other embodiments, the detection openings 4011 are aligned with one or more light output devices (e.g., LEDs) that produce an electronic output to the user based on the signals produced by and/or within the detection module 4800. For example, in some embodiments, the electronic system 4950 can include a digital read module implemented in at least one of a memory or a processing device that determines the presence of a signal (e.g., colorimetric output) produced by the detection module 4800. As shown, in some embodiments, the top housing 4010 can include indicia 4017 identifying the detection opening to a specific result (e.g., a control output, an indication of whether the target pathogen is present, and indications of whether the target pathogen is resistant to or susceptible to a drug or treatment regimen.

The top housing 4010 includes a lid portion to which the sample lid 4140 is movably coupled. The top housing 4010 includes a lock surface to which the lid 4140 engages to prevent downward motion of the lid 4140 and the sample input actuator 4050 when the lid 4140 is in the opened position.

Figure 10:
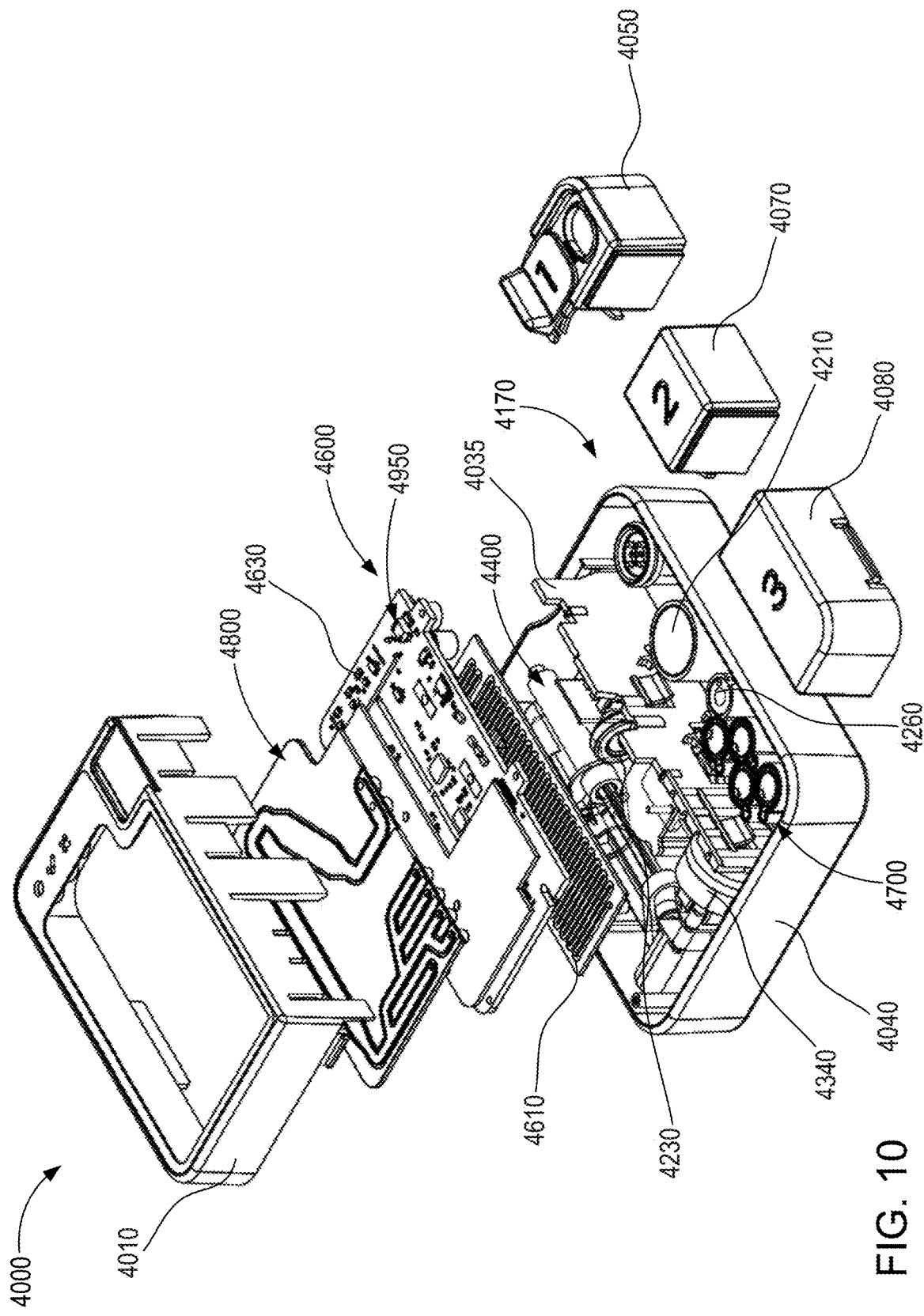
FIG. 10 is an exploded view of the molecular diagnostic test device shown in FIGS. 6 and 7.

Referring to FIG. 10, the housing assembly 4001 includes the vertical manifold 4035, which provides both structural support and defines flow paths for various fluids that are conveyed within the device 4000. In particular, the vertical manifold 4035 defines a series of reagent passages through which reagents are conveyed from the reagent module 4700 to the detection module 4800. Additionally, the vertical manifold 4035 defines on or more vent passages to allow venting to facilitate fluid movement throughout the device 4000.

The housing assembly 4001 includes the sample transfer manifold 4100, which provides both structural support and defines flow paths for various fluids that are conveyed within the device 4000. In particular, the sample transfer manifold 4100 includes a sample input portion 4102, a wash portion 4103, an elution portion 4104, and a reagent portion 4105.

The sample preparation module 4200 includes a sample input module 4170, a wash module 4210, an elution module 4260, a filter assembly 4230, and various fluidic conduits (e.g., tubes, lines, valves, etc.) connecting the various components. The device 4000 also includes the lysing module 4300 and the amplification reagent (or mixing) module 4500, which, together with the sample preparation module 4200, performs the nucleic acid extraction and preparation of an amplification solution according to any of the methods described herein. Thus, although the sample preparation module 4200, the sample input module 4170, the inactivation module 4300, and the amplification reagent module 4500 are described as separate modules, in other embodiments, the structure and function of the sample preparation module 4200 can be included within or performed by the inactivation module 4300, the amplification reagent module 4500, and/or the sample input module 4170, and vice-versa. Similarly stated, any of the sample input modules, sample preparation modules, inactivation modules and/or lysing modules described herein can include any of the structure and/or perform any of the functions of the other modules to perform any of the methods of sample preparation or nucleic acid extraction described herein. By eliminating the need for external sample preparation and a cumbersome instrument, the device 4000 is suitable for use within a point-of-care setting (e.g., doctor's office, pharmacy or the like) or at the user's home, and can receive any suitable biological sample S1. The biological sample S1 (and any of the input samples described herein) can be any of the types of samples described herein.

Figure 11:
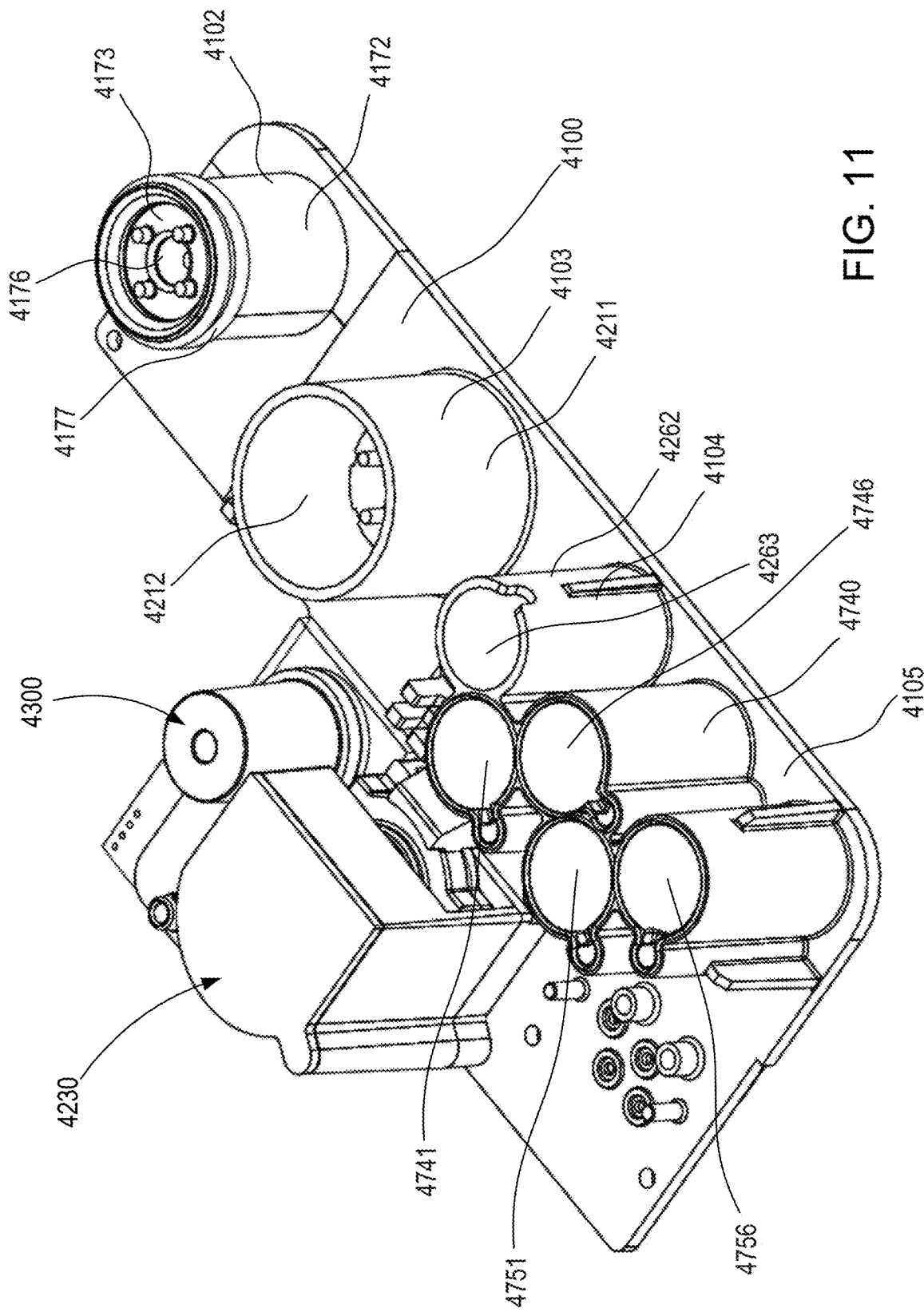
FIG. 11 is a perspective view of the molecular diagnostic test device shown in FIGS. 6 and 7, including a filter assembly and an inactivation assembly coupled thereto.

The sample input module 4170 is configured to receive a biological sample S1 containing a biological entity, and convey the biological sample toward the remaining elements of the sample preparation module 4200 (e.g., the filter assembly 4230). The sample input module 4170 includes the sample input portion 4102 of the sample transfer manifold 4100, the sample input (or first) actuator 4050, and the lid 4140. Referring to FIG. 11, the sample input portion 4102 of the sample transfer manifold 4100 includes a cylindrical housing 4172 and a cover. As shown, the top surface of the cylindrical housing 4172 (including the top surface 4173 and/or portions of the cover) and an inner surface of the first actuator 4050 define a sample input volume 4068, within which the biological sample is conveyed at the start of a test. The outer portion of the cylindrical housing 4172 includes one or more seals 4177 that slidingly engage the inner surface of the first actuator 4050 to form a fluid-tight seal. In some embodiments, the sample input volume 4068 or other portions of the sample input module 4170 can include a reagent (e.g., a positive control or other reagent as described herein).

The cylindrical housing 4172 defines a first (or vertical) fluid passage 4176 that is between (and fluid communication with) a sample input passage defined by the sample transfer manifold 4100 and that is in fluid communication with the wash module 4210 and the filter assembly 4230. In this manner, when the biological sample is compressed by the first actuator 4050 it is conveyed from the sample input volume 4068, through the first fluid passage and towards the filter assembly 4230.

The wash module 4210 is configured to convey a wash solution toward the remaining elements of the sample preparation module 4200 (e.g., the filter assembly 4230). In some embodiments, the wash module 4210 is configured such that it cannot be actuated out of the desired sequence of operations. Specifically, in some embodiments, the wash module 4210 is configured to be locked until after the biological sample has been conveyed to the sample preparation module 4200. The wash module 4210 includes the wash portion 4103 of the sample transfer manifold 4100, the wash (or second) actuator 4070, and a wash container. Referring to FIG. 11, the wash portion 4103 of the sample transfer manifold 4100 includes a cylindrical housing 4211 and a top surface (or cover) (not shown). The upper portion of the cylindrical housing 4211 defines a volume 4212 within which a wash container (not shown) is disposed. The wash container can be a sealed wash container that allows the sample wash solution to be stored for long periods of time (e.g., 6 months or longer). The wash solution within the wash container can be any suitable solution. The wash module 4210 is actuated by the wash (or second) actuator 4070

As described herein, the biological sample and the wash solution are conveyed through the filter assembly 4230. The filter assembly is configured to receive an elution buffer (via a backflush operation) to convey the desired particles (and the elution buffer) to the lysing module 4300. After the filtering operation, the elution buffer and the captured particles flow out of the filter assembly 4230 and toward the lysing module 4300 via a sample outlet port.

The elution module (or assembly) 4260 of the sample preparation module 4200 is contained within the housing, and defines an elution volume within which an elution composition is stored. The elution composition can be any of the elution compositions described herein. In some embodiments, the elution composition can include proteinase K, which allows for the release of any bound cells and/or nucleic acid molecules (e.g., DNA) from the filter membrane. The output from the elution module 4260 can be selectively placed in fluid communication with the filter assembly 4230, when the filter assembly is toggled into a backflow configuration, as described above. Thus, the elution module 4260 can include any suitable flow control devices, such as check valves, duck-bill valves, or the like to prevent flow back towards and/or into the elution volume.

In some embodiments, the elution module 4260 is configured such that it cannot be actuated out of the desired sequence of operations. Specifically, in some embodiments, the elution module 4260 is configured to be locked until after the biological sample has been conveyed to the sample preparation module 4200 and the wash operation (described above) has occurred. The elution module 4260 includes the elution portion 4104 of the sample transfer manifold 4100, the reagent (or third) actuator 4080, and an elution plunger (not shown). Referring to FIG. 11, the elution portion 4104 of the sample transfer manifold 4100 includes a cylindrical housing 4262 that defines an elution volume 4263 within which the elution buffer (or composition) is contained. The elution module 4260 is actuated by the reagent (or third) actuator 4080.

The lysing module 4300 includes a chamber body and a heater. In use, the sample (e.g., the filtered sample) is conveyed into the chamber body and heated to a first temperature within a lysing temperature range to lyse certain constituents in the solution or de-activate the enzymes present in input fluid after lysis occurs. In some embodiments, the lysing module 4300 can be used in conjunction with RT-PCR and can beat or maintain the solution at a temperature to release a ribonucleic acid (RNA) molecule within the solution.

After the lysing and/or inactivation operations, the output from the lysing module 4300 can be conveyed into the mixing module (also referred to as the amplification reagent module) 4500, which mixes the output of inactivation module 4300 with the reagents to produce an amplification solution. In some embodiments, the amplification reagent module 4500 contains a primer set targeting a single nucleotide polymorphism (SNP) locus in a polynucleotide of the biological sample S1. The SNP primer set P can include any of the SNP primer sets shown and described herein. In some embodiments, the primer set P can also target a locus in a polynucleotide associated with a target pathogen (e.g., organism, bacteria). Thus, in some embodiments, the device (and methods using the device) can produce one amplicon through which the presence of the organism and whether the organism is resistant or susceptible to a treatment can be detected. In other embodiments, the device (and methods using the device) can produce two or more amplicons through which the presence of the organism and whether the organism is resistant or susceptible to a treatment can be detected. In some embodiments, the amplification reagent module 4500 is configured to reconstitute the reagent in a predetermined input volume, while ensuring even local concentrations of reagents in the entirety of the volume. In some embodiments, the mixing chamber module 4500 is configured to produce and/or convey a sufficient volume of liquid for the amplification module 4600 to provide sufficient volume output to the detection module 4800. The mixing module 4500 can be any suitable mixing module, such as those shown and described in International Patent Publication No. WO2016/109691, entitled "Devices and Methods for Molecular Diagnostic Testing," which is incorporated herein by reference in its entirety The fluidic drive (or transfer) module 4400 can be a pump or series of pumps configured to produce a pressure differential and/or flow of the solutions within the diagnostic test device 4000. Similarly stated, the fluid transfer module 4400 is configured to generate fluid pressure, fluid flow and/or otherwise convey the biological sample and the reagents through the various modules of the device 4000. The fluid transfer module 4400 is configured to contact and/or receive the sample flow therein. Thus, in some embodiments, the device 4000 is specifically configured for a single-use to eliminate the likelihood that contamination of the fluid transfer module 4400 and/or the sample preparation module 4200 will become contaminated from previous runs, thereby negatively impacting the accuracy of the results. The fluid transfer module 4500 can be any suitable fluid transfer module, such as those shown and described in International Patent Publication No. WO2016/109691, entitled "Devices and Methods for Molecular Diagnostic Testing," which is incorporated herein by reference in its entirety.

After being mixed within the amplification reagent module 4500, the prepared sample is then conveyed to the amplification module 4600 (as shown by the arrow EE in FIG. 5). The amplification module 4600 includes a flow member 4610 and a heater 4630. The flow member 4610 can be any suitable flow member that defines a volume or a series of volumes within which the that prepared solution can flow and/or be maintained to amplify the target nucleic acid molecules within the solution. The heater 4630 can be any suitable heater or group of heaters coupled to the flow member 4610 that can beat the prepared solution within the flow member 4610 to perform any of the amplification operations as described herein.

In some embodiments, the flow member 4610 defines a single volume within which the prepared solution is maintained and heated to amplify the nucleic acid molecules within the prepared solution. In other embodiments, the flow member 4610 can define a "switchback" or serpentine flow path through which the prepared solution flows. Similarly stated, the flow member 4610 defines a flow path that is curved such that the flow path intersects the heater 4630 at multiple locations. In this manner, the amplification module 4600 can perform a "flow through" amplification reaction where the prepared solution flows through multiple different temperature regions.

Although the amplification module 4600 is generally described as performing a thermal cycling operation on the prepared solution, in other embodiment, the amplification module 4600 can perform any suitable thermal reaction to amplify nucleic acids within the solution. In some embodiments, the amplification module 4600 (and any of the amplification modules described herein) can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process The detection methods enabled by the device 4000 include sequential delivery of the detection reagents and other substances within the device 4000. Further, the device 4000 is configured to be an "off-the-shelf" product for use in a point-of-care location (or other decentralized location), and is thus configured for long-term storage. Accordingly, the reagent storage module 4700 is configured for simple, non-empirical steps for the user to remove the reagents from their long-term storage containers, and for removing all the reagents from their storage containers using a single user action. In some embodiments, the reagent storage module 4700 and the rotary selection valve 4340 are configured for allowing the reagents to be used in the detection module 4800, one at a time, without user intervention.

Specifically, the device 4000 is configured such that the last step of the initial user operation (i.e., the depressing of the reagent actuator 4080) results in dispensing the stored reagents. This action crushes and/or opens the sealed reagent containers present in the assembly and relocates the liquid for delivery. The rotary venting selector valve 4340 allows the reagent module 4700 to be vented for this step, and thus allows for opening of the reagent containers, but closes the vents to the tanks once this process is concluded. Thus, the reagents remain in the reagent module 4700 until needed in the detection module 4800. When a desired reagent is needed, the rotary valve 4340 opens the appropriate vent path to the reagent module 4700, and the fluidic drive module 4400 applies vacuum to the output port of the reagent module 4700 (via the detection module 4800), thus conveying the reagents from the reagent module 4700. The reagent module 4700 and the valve 4340 can be similar to the reagent modules and valves shown and described in International Patent Publication No. WO2016/109691, entitled "Devices and Methods for Molecular Diagnostic Testing," which is incorporated herein by reference in its entirety.

The detection module 4800 is configured to receive output from the amplification module 4600 and reagents from the reagent module 4700 to produce one or more colorimetric changes to indicate presence or absence of target pathogen (e.g., bacteria, virus, or organism) in the initial input sample and whether the target pathogen is resistant to or susceptible to a treatment regimen (e.g., antibiotics). The detection module 4800 also produces one or more colorimetric signals to indicate the general correct operation of the test (positive control and negative control). In some embodiments, color change induced by the reaction is easy to read and binary, with no requirement to interpret shade or hue. In other embodiments, the electronic system 4950 of the device includes a digital read module implemented in at least one of a memory or a processing device that determines the presence the one or more colorimetric outputs produced by the detection module 4800. For example, in some embodiments, the electronic system 4950 can include at least one light source and at least one light detector and the digital detection module can perform an algorithm based on detected light attenuated by or reflecting from a detection surface to determine the presence of a color change on the detection surface. In some embodiments the electronic system 4950 can include any of the components and perform any of the features of the electronic system 2900 described below.

Figure 12:
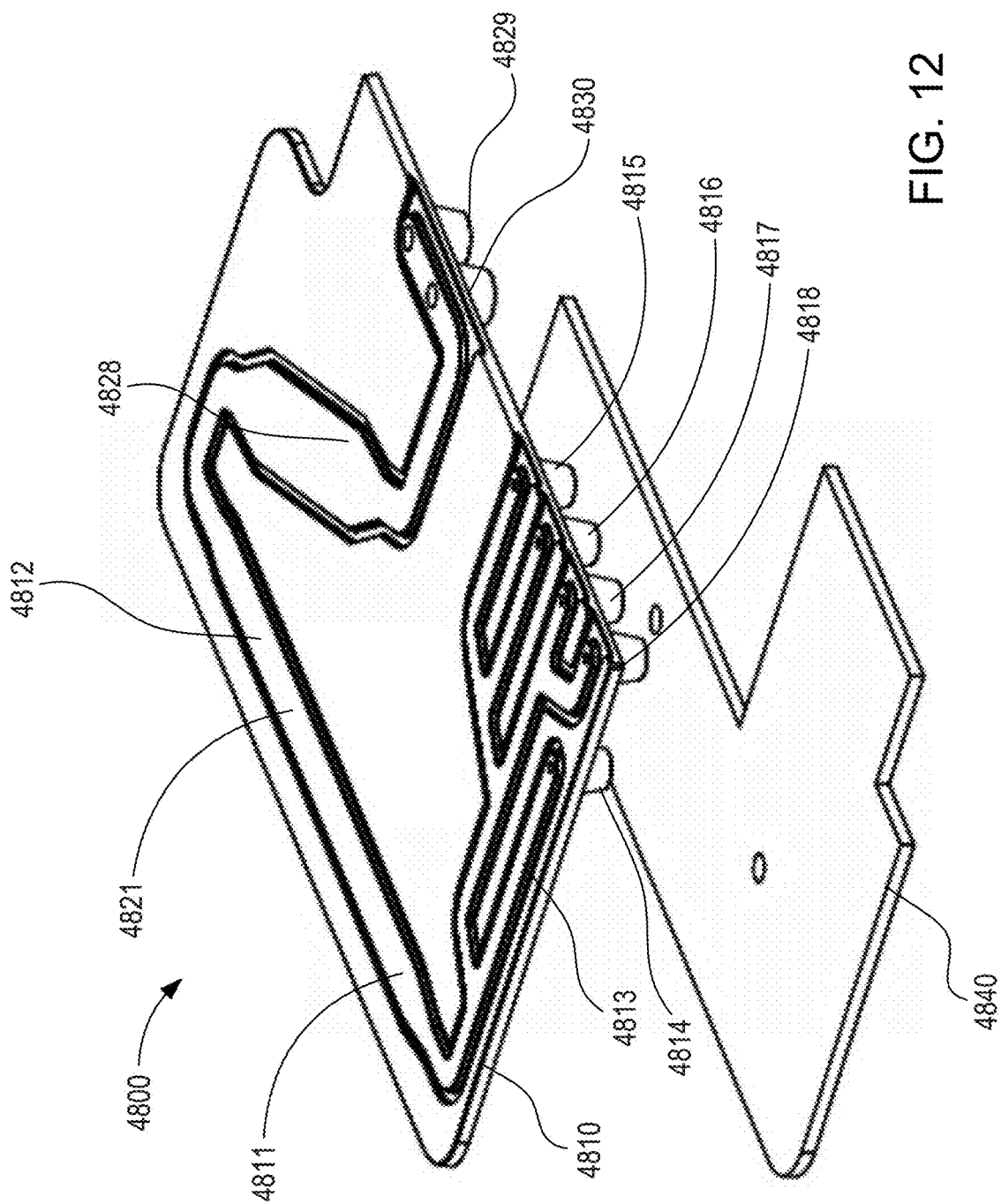
FIGS. 12 and 13 are a perspective exploded view and a front view, respectively, of a detection module of the molecular diagnostic test device shown in FIGS. 6 and 7.
Figure 13:
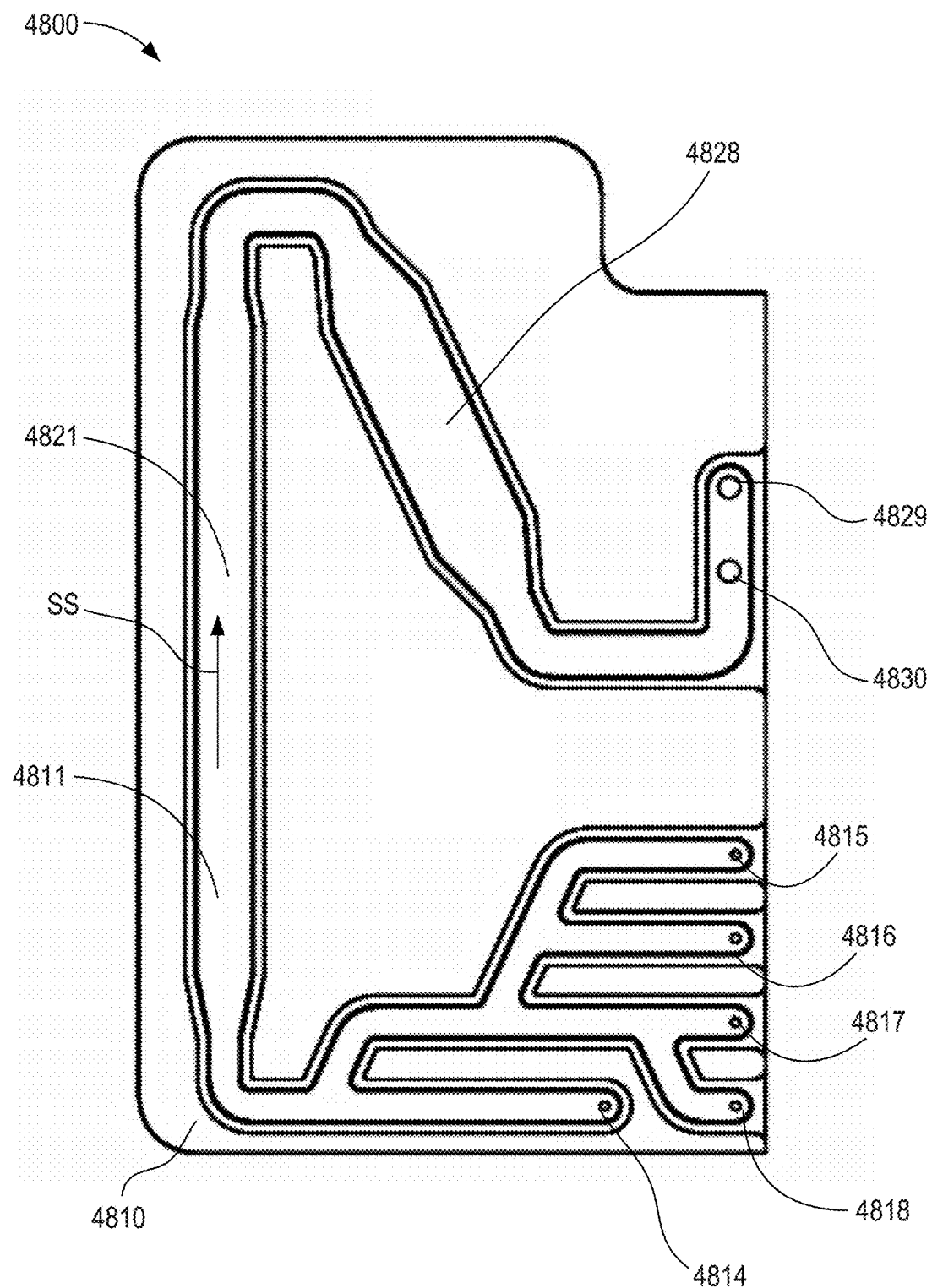

Referring to FIGS. 12 and 13, the detection module includes a lid (not shown), a detection housing 4810 and a heater 4840. The heater 4840 can be similar to any of the circuit board heaters described herein and also shown and described in International Patent Publication No. WO2016/109691, entitled "Devices and Methods for Molecular Diagnostic Testing," which is incorporated herein by reference in its entirety. The lid and the detection housing 4810 form a flow cell for detection. The housing 4810 defines a detection chamber/channel 4812 having a sample inlet portion 4813, a reagent inlet portion, a detection portion 4821, and an outlet portion 4828. The sample inlet portion 4813 includes the sample inlet port 4814, which is fluidically coupled to the outlet of the amplification module 4600 and receives the amplified sample. The reagent inlet portion includes a first reagent inlet port 4815, a second reagent inlet port 4816, a third reagent inlet port 4817, and a fourth reagent inlet port 4818. The first reagent inlet port 4815 is coupled to the reagent module 4700 via the vertical manifold 4035. Thus, in use a first reagent (e.g., a detection reagent, such as the first reagent R1 described above with reference to the reagent module 1700) can be conveyed into the detection channel 4812 via the first reagent inlet port 4815. The second reagent inlet port 4816 is coupled to the reagent module 4700 via the vertical manifold 4035. Thus, in use a second reagent (e.g., a wash solution) can be conveyed into the detection channel 4812 via the second reagent inlet port 4816. The third reagent inlet port 4817 is coupled to the reagent module 4700 via the vertical manifold 4035. Thus, in use a third reagent (e.g., a detection reagent, such as the second reagent R2 described above with reference to the reagent module 1700) can be conveyed into the detection channel 4812 via the third reagent inlet port 4817. The fourth reagent inlet port 4818 is coupled to the reagent module 4700 via the vertical manifold 4035. Thus, in use a fourth reagent (e.g., a second flow of a detection reagent, such as the second reagent R2 described above with reference to the reagent module 700) can be conveyed into the detection channel 4812 via the first reagent inlet port 4818.

The detection channel 4812 includes an entrance portion 4811, a detection portion 4821, and outlet portion 4828. The detection portion (or "read lane") 4821 is defined, at least in part by, and/or includes a series of detection surfaces. The detection surfaces 4821 include a series of capture probes to which the target amplicon(s) produced during amplification can be bound when the detection solution flows across the detection surface 4821. For example, the capture probes may include one or more allele-specific probes, one or more capture probe that bind the target amplicon outside the SNP locus, and/or one or more capture probes that bind an second target amplicon for the same organism. In some embodiments, the detection surfaces 4821 are configured for multiplex detection and/or drug-sensitivity determination using multiple SNP loci and/or multiple target organisms. The capture probes can be any suitable probes formulated to capture or bind to the target amplicon, such as those described above with respect to the detection module 1800 or any other probes described herein.

Although the device 4000 is described as including a filter assembly 4230, in some embodiments, a sample preparation device need not include a filter or filter assembly. For example, in some embodiments, the sample input may be directly linked to a lysing/inactivation chamber, similar to the lysing chamber 4300 as shown above. Advantages of a device without a filter assembly include lower pressures in the device, no risk of breaking a filter, fewer parts, fewer reagents required, higher recovery of target organisms from the clinical sample matrix and higher recovery of DNA from target organisms. In such embodiments, a device differs from the device 4000 in that the sample is flowed from the input module 4170 directly to the lysing module 4300. In some embodiments, the sample may be lysed by heating without need for a specialized lysis buffer or lysis enzymes. Any proteases or nucleases released from the cells of the sample will be inactivated by heating. For example, a sample may be flowed into the lysing module and held until the module reaches a set temperature (for example greater than 90C) and then flowed through an inactivation segment. In the inactivation segment, the sample is rapidly heated to 95C causing the cells in the sample to lyse and proteins from within the cells to be inactivated.

The device 4000 can be used to perform any of the methods described herein. To use the device, a biological sample is first placed into the sample input volume 4068, as described above. The lid 4140 is then moved to it closed position, thereby sealing the sample input volume 4068. After the lid 4140 is closed, the first actuator 4050 can be manipulated to actuate the sample input module 4170. Movement of the first actuator 4050 compresses the sample input volume 4068 and pushes the sample to the filter assembly 4230. The second actuator 4070 can then be depressed. This causes the wash solution to be conveyed into the filter assembly 4230, as described above. The third actuator 4080 can then be depressed to actuate the filter assembly 4230 and also causes the elution solution to be conveyed into the filter assembly 4230, as described above. The movement of the third actuator 4080 also releases the reagents from the reagent canisters. In some embodiments, the device 4000 can be used to detect the presence of a target organism and whether the target organism is susceptible to a treatment regimen or resistant to the treatment regimen.

In some embodiments, any of the detection modules described herein can include a set of probes designed to bind to one or more genetic loci (loci) in a manner that allows for detection of the target organism and whether the target organism is susceptible to a treatment regimen or resistant to the treatment regimen over a wide range of concentrations of organism typically found in the biological sample (e.g., vaginal, rectal, nasal pharyngeal swabs, urine, blood or other commonly acquired human specimens). For example, certain biological samples may have a very low concentration of the target organism that, even after amplification, produces a low concentration of the target amplicon for detection. To accommodate detection of low amplicon concentrations, a probe can be designed to ensure a high level of capture efficiency (i.e., the probes can have a strong binding to the amplicon, e.g. high $T_m$). The inclusion of a probe having a high level of capture efficiency, however, can also result in undesirable non-specific binding. Non-specific binding can reduce the accuracy of the test, for example, when a biological sample produces a high concentration of a target amplicon and a portion of the target amplicon is non-specifically bound to a probe to which binding is not desired. For example, when testing for resistance or susceptibility to a target organism (e.g., NG) to a treatment regimen (e.g., ciprofloxacin), using two probes and two separate detection surfaces (e.g., one for detection of a first target allele within the target organism associated with resistance to a treatment and the other for detection of a second target allele within the target organism associated with susceptibility to the treatment) can facilitate detection over a wide range of amplicon concentrations and with a high sensitivity and specificity.

Figure 14:
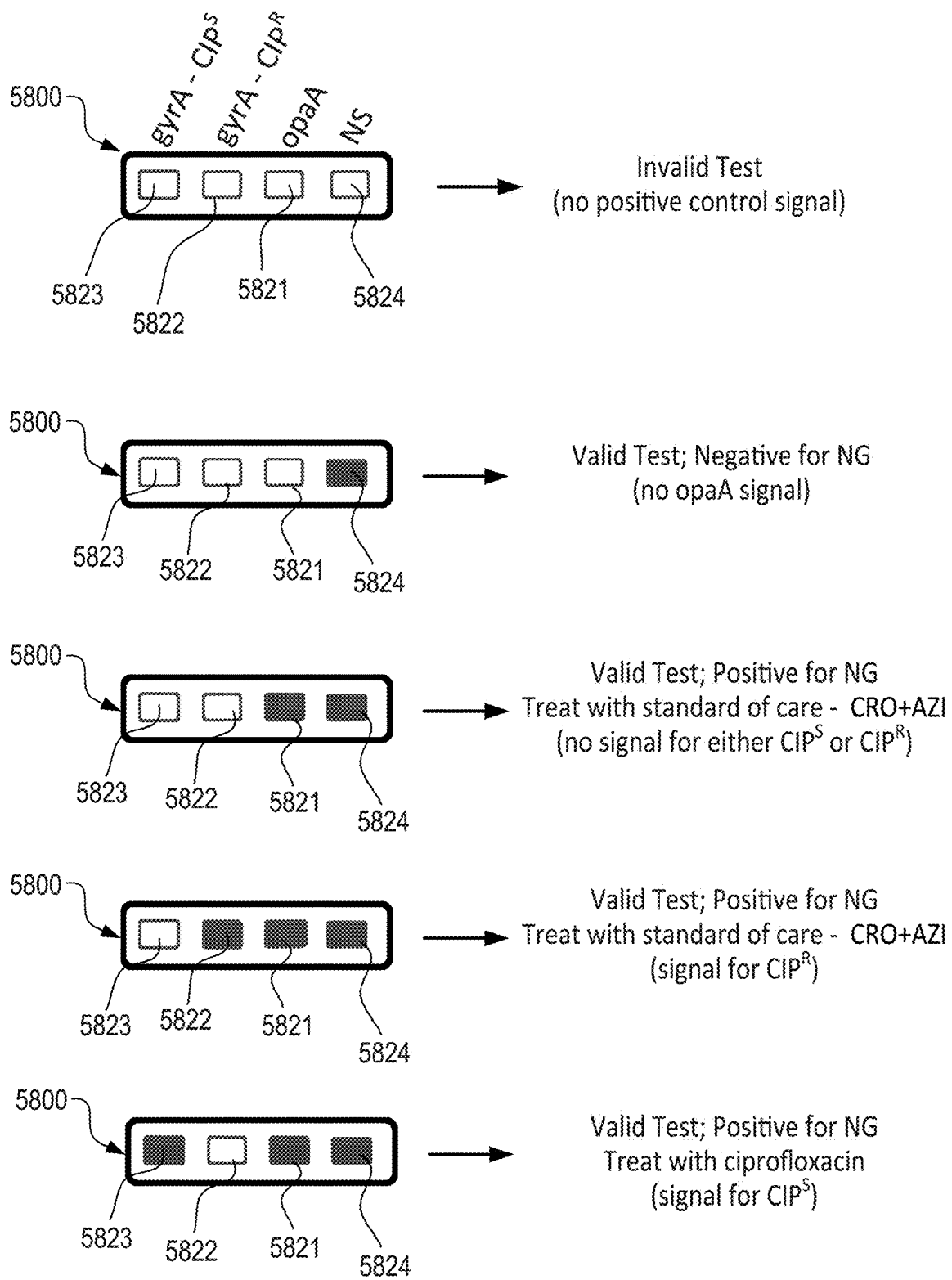
FIG. 14 is a schematic illustration or a detection module including a set of probes, according to an embodiment, in various detection configurations.

For example, FIG. 14 shows a schematic illustration of a detection module 5800 according to an embodiment that includes a set of detection surfaces that each contain a probe adhered thereto. Although the detection module 5800 is described as being used to detect the presence of NG and whether the NG strain is resistant to or susceptible to ciprofloxacin, in other embodiments, the detection module 5800 can be used in any of the devices and for any of the methods described herein. Moreover, although the structural details of the detection module 5800 are not shown in FIG. 14, the detection module 5800 can include similar structure as shown for any of the detection modules described herein (e.g., the detection module 5800 can include a heater and/or a flow channel as shown in the detection module 4800). As shown, the detection module 5800 includes a control detection surface 5824, a first detection surface 5821, a second detection surface 5822, and a third detection surface 5823. The control detection surface 5824 includes a control probe adhered thereto that is designed to bind to a genetic locus in a polynucleotide associated with the positive control substance. In this embodiment, the positive control substance is *N. subflava*, (NS). The first detection surface 5821 includes a first probe adhered thereto and that is designed to permit annealing or hybridization of a target amplicon with sufficient specificity to permit detection of the presence (or absence) of the target amplicon indicating the presence of NG. Similarly stated, the first probe is designed to bind to a first genetic locus in a polynucleotide associated with NG. As indicated in FIG. 14, in some embodiments, the target amplicon for detection of NG strains can be the opaA amplicon, and the first probe can be specific to the opaA amplicon.

The second detection surface 5822 includes a second probe adhered thereto and designed to permit annealing or hybridization of a target amplicon with sufficient specificity to permit detection of the presence (or absence) of the target amplicon if a first allele is present (or absent) in an allele-specific manner. As shown, the first allele is associated with resistance of NG to ciprofloxacin (identified as $CIP^R$, the first allele being referred to as a "—R allele"). Similarly stated, the second probe is designed to bind to a second genetic locus if the second genetic locus comprises the first target allele associated with resistance of NG to ciprofloxacin. As indicated in FIG. 14, in some embodiments, the target amplicon for detection of resistance or susceptibility can be the gyrA gene of NG. Specifically, ciprofloxacin-susceptible isolates of NG harbor a single nucleotide polymorphism (SNP) at codon 91 of the gyrA gene (gyrA Ser91). Although mutations in other codons (gyrA Asp95) and genes (parC) have been detected, mutations in the gyrA Ser91 codon are necessary and sufficient to confer ciprofloxacin resistance. Thus, the first target allele for $CIP^R$ is an allele encoding the ciprofloxacin-sensitive gyrA Ser-91 genotype.

The third detection surface 5823 includes a third probe adhered thereto and designed to permit annealing or hybridization of a target amplicon with sufficient specificity to permit detection of the presence (or absence) of the target amplicon if a second allele is present (or absent) in an allele-specific manner. As shown, the second allele is associated with susceptibility of NG to ciprofloxacin (identified as $CIP^S$, the second allele being referred to as a "—S allele"). Similarly stated, the third probe is designed to bind to the target amplicon if the target amplicon comprises the second target allele associated with susceptibility of NG to ciprofloxacin. As indicated in FIG. 14, in some embodiments, the target amplicon for detection of resistance or susceptibility can be the gyrA gene of NG; the first target allele for $CIP^R$ is a ciprofloxacin-resistant gyrA (e.g., gryA-Phe-91, gyrA Tyr-91, gyrA Asp-95 and gyrA Gly-95) codon and the second target allele for $CIP^S$ is the ciprofloxacin-susceptible gyrA Ser-91 codon.

The detection module 5800 enables a 4-plex assay for detection of NG and whether the NG strain is resistant to or susceptible to ciprofloxacin. As shown in FIG. 14, the absence of a positive control signal indicates an invalid test and the presence of a positive control signal indicates a valid test result. The various combinations of signals produced from the first detection surface 5821, the second detection surface 5822, and the third detection surface 5823 can produce results directing the user to an appropriate treatment regimen. In some embodiments, the second probe (adhered to the second detection surface 5822) and the third probe (adhered to the third detection surface 5823) can be designed to facilitate accurate test results over a wide range of NG concentration. For example, in some embodiments the second probe (for detecting $CIP^R$) can be a "weak" probe (lower $T_m$) and the third probe (for detecting $CIP^S$) can be a "strong" probe. Similarly stated, the device may be configured to generate no signal for either $CIP^S$ or $CIP^R$ at low input concentrations or when amplification is inefficient (causing default to administration of standard of care CRO+AZI); yet to sensitively detect $CIP^S$ NG at high input concentrations or efficient amplification, without signal from the weak second probe (for detecting $CIP^R$). Advantageously, asymmetric probes have a low false positive rate at high concentrations because the weak second probe generates signal if any resistant organism is present; and also a low false positive rate at low concentrations because negative signal from both second probe and third probe indicates administration of standard of care despite an indeterminate result for resistance or susceptibility.

The inclusion of two probes and detection surfaces (one for $CIP^R$ and the other for $CIP^S$) along with mismatched probes can improve the sensitivity and specificity for detecting the presence of NG and whether the NG strain is susceptible to treatment via ciprofloxacin. For example, in treating NG the current standard of care is to treat for a drug resistant strain (e.g., CRO+AZI), due to the increased amount of NG strains that are resistant to ciprofloxacin. As such, when the detection module 5800 (and the associated methods) detects NG, the standard of care for $CIP^R$ should be applied unless there is a very high certainty that the NG strain is susceptible to the alternative treatment (ciprofloxacin). Similarly stated, it desirable for the detection module 5800 (and associated methods) to have a high specificity for detecting whether the NG strain is susceptible to ciprofloxacin. Additionally, it is desirable that the test accurately indicates when a susceptible NG strain is present. If, for example, the test misses a large number of susceptible NG strains and instead directs the current standard of care, the value of the test is limited. As such, the second probe is designed minimize the likelihood of non-specific binding with the —S allele, which would erroneously produce a drug resistant signal from the second detection surface 5822 for an NG strain that is actually susceptible to treatment with ciprofloxacin. Such non-specific bind is more likely to occur when there is a high concentration of the susceptible NG in the biological sample and/or the output solution from amplification. Thus, the second probe is designed to be "weak"— i.e. to have a low $T_m$ (for both its allele—$CIP^R$—and the antiallele—$CIP^S$) in comparison to the temperature of the detection chamber and in comparison to the $T_m$ of the third probe (for its allele—$CIP^S$). The third probe advantageously has a low $T_m$ for its ant allele—$CIP^R$. In contrast, the third probe is designed maximize the likelihood of producing a signal from the third detection surface 5823 even with low concentrations of the susceptible NG. Thus, the third probe is designed to be "strong" (i.e. higher $T_m$, such as a $T_m$ of about the temperature of the detection chamber).

Although the inclusion of a weak second probe on the second detection surface 5822 can result in an insufficient signal when there is a low concentration of the NG strain that is drug resistant, the use of the third detection surface (with the third probe) to test for the —S allele reduces the likelihood that the test will erroneously identify the NG as susceptible, even though the third probe is a "strong" probe. Specifically, if the concentration of the —R allele is low enough such that an insufficient signal is produced from the second detection surface 5822, then such concentration is also unlikely to produce a sufficiently high signal from the third detection surface 5823 as a result of non-specific binding to the third probe. Moreover, as described below, in some embodiments, the signals from the second detection surface 5822 and the third detection surface 5823 are compared and the device will only indicate a "susceptible" result if a difference between or ratio of the signal produced by the third detection surface 5823 and the signal produced by the second detection surface 5822 exceeds a threshold.

In some embodiments, the detection module 5800, as well as any other detection modules, probe designs, and methods described herein can produce a result having a sensitivity of at least 85 percent for detecting the presence of NG and a specificity of at least 90 percent for detecting whether the NG strain is susceptible to ciprofloxacin. In other embodiments, the detection module 5800, as well as any other detection modules, probe designs, and methods described herein can produce herein can produce a result having a sensitivity of at least 90 percent for detecting the presence of NG and a specificity of at least 95 percent for detecting whether the NG strain is susceptible to ciprofloxacin. In other embodiments, the detection module 5800, as well as any other detection modules, probe designs, and methods described herein can produce herein can produce a result having a sensitivity of at least 90 percent for detecting the presence of NG and a specificity of at least 90 percent for detecting whether the NG strain is susceptible to ciprofloxacin. In other embodiments, the detection module 5800, as well as any other detection modules, probe designs, and methods described herein can produce herein can produce a result having a sensitivity of at least 95 percent for detecting the presence of NG and a specificity of at least 90 percent for detecting whether the NG strain is susceptible to ciprofloxacin.

The detection module 5800, as well as any other detection modules, probe designs, and methods described herein can produce an accurate result over a wide range of concentration of the target organism (as measured in either the biological sample or in the amplified product. For example, in some embodiments, an amplification module can produce an output solution having between about 3 nM and about 10 nM of the amplified polynucleotide. In some embodiments, an amplification module can produce an output solution having between about 0.5 nM and about 200 nM of the amplified polynucleotide, in some embodiments, an amplification module can produce an output solution having between about 0.1 nM and about 200 nM of the amplified polynucleotide.

In an aspect, the disclosure provides, a molecular diagnostic device, comprising a sample preparation module configured to receive a biological sample, wherein the biological sample comprises a polynucleotide; a reagent module containing a primer set targeting a single nucleotide polymorphism (SNP) locus in the polynucleotide; an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele.

In some embodiments, the primer set is designed to flank the SNP locus.

In some embodiments, a length of a target region flanked by the primer set is between about 60 and about 140 base pairs.

In some embodiments, a length of a target region flanked by the primer set is between about 80 and about 120 base pairs.

In some embodiments, the target amplicon comprises minimal secondary structure.

In some embodiments, wherein the primer set designed to target a SNP locus comprises: i) an upstream oligonucleotide primer substantially complementary to an upstream primer binding site at the 5' terminus of the target region on the antisense strand; and ii) a downstream oligonucleotide primer substantially complementary to a downstream primer binding site at the 3' terminus of the target region on the sense strand.

In some embodiments, the molecular diagnostic device comprises a temperature controller configured to maintain the temperature of the detection module at at about 5° C., about 10° C., or about 15° C. less than the melting temperature of the first probe.

In some embodiments, the detection module comprises a temperature controller configured to maintain a predetermined temperature for the detection module, and wherein the first probe is designed to have a melting temperature at about 5° C., about 10° C., or about 15° C. less than the predetermined temperature.

In some embodiments, the probe is substantially complementary to a probe binding site comprising the SNP locus, and comprises a nucleotide matched the target allele.

In some embodiments, the probe comprises at most two nucleotide mismatches to the probe binding site.

In some embodiments, the probe is perfectly complementary to the probe binding site.

In some embodiments, the probe does not overlap the primer set design to target the SNP locus.

In some embodiments, the detection module comprises a second probe substantially complementary to a second probe binding site, wherein the second probe binding site does not comprise the SNP locus.

In some embodiments, the second probe binding site does not overlap the binding site of the first probe. In some embodiments, the binding site for the first probe and the binding site for the second probe have partial overlap (e.g., overlap of 1 nt, 2 nt, 3 nt, or more). In some embodiments, the binding site for the second probe does not comprise the SNP locus, as the second probe is designed not to discriminate between alleles at the SNP locus.

In some embodiments, the detection module comprises a second probe substantially complementary to a second probe binding site within the target amplicon, wherein the second probe binding site does not overlap the binding site of the first probe.

In some embodiments, the target allele is a drug-resistance allele.

In some embodiments, the molecular diagnostic device specifically detects the drug-resistance allele in the biological sample.

In some embodiments, the allele is a drug-sensitivity allele.

In some embodiments, the molecular diagnostic device specifically detects the drug-resistance allele in the biological sample.

In some embodiments, the SNP locus is within a gyrA region.

In some embodiments, the primer set is designed to flank the gyrA 91 locus.

In some embodiments, a length of the gyrA region flanked by the primer set is between about 60 and about 140 base pairs.

In some embodiments, a length of the gyrA region flanked by the primer set is between about 80 and about 120 base pairs.

In some embodiments, a length of the gyrA region flanked by the primer set includes a secondary structure.

In some embodiments, the first probe is designed to maximize binding to the wild type, ciprofloxacin-sensitive gyrA Ser-91 genotype while minimizing binding to other SNPs at a gyrA Ser-91 site that confers a drug resistance.

In some embodiments, the first probe is substantially complementary to a first probe binding site comprising the codon encoding gyrA Ser-91, and wherein the first probe comprises a nucleotide that matches an allele encoding ciprofloxacin-sensitive gyrA Ser-91 genotype.

In some embodiments, the first probe discriminates between an allele encoding the ciprofloxacin-sensitive gyrA Ser-91 genotype and the antiallele encoding the gyrA Ser-91 site that confers resistance to ciprofloxacin.

As used here, the term "discriminates" refers to the ability or capacity of a device to determine the presence of a particular SNP of interest within an amplified region of sequence. For example, the device may produce an intensity of signal from the SNP-specific capture probe that indicates the presence of the target allele at the SNP locus in the target amplicon (or other polynucleotide) introduced into the detection module (whether the target amplicon is produced on a device having both amplification and detection module; supplied to a device having a detection module but no amplification module; or transferred from a device having an amplification module to a device having a detection module). In some embodiments, the signal (e.g., a colorimetric change) produced by the device at test spot (e.g., detection surface detection surface 4821) having the capture probe is compared to the signal produced by the same or equivalent device when the target amplicon (or other polynucleotide) lacking the target allele at the SNP locus is provided to the detection module. Stated differently, response criteria can be set by standardization of signal intensity from similarly manufactured devices. The control probe is an optimal feature of the device. In some embodiments, the signal produced by the device from the test spot is compared to the signal produced by the device at a control spot (e.g., a detection surface 4821) having a control capture probe. For example, the device may be engineered or calibrated to produce a similar or substantially equal signal at the two detection surfaces (capture probe and control capture probe) as an indicator for presence of the target allele; and to produce a reduced signal from the capture probe, compared to the control capture probe, where the target amplicon (or other polynucleotide) lacks the target allele at the SNP locus.

Stated different, the signal from the two detection surfaces may be similar or substantially equal when the biological sample comprising a polynucleotide from a drug-sensitive (or drug-resistant) pathogen (e.g. an antibiotic-sensitive bacteria); and different when the biological sample comprising a polynucleotide from a drug-resistant (or drug-sensitive) pathogen (e.g. an antibiotic-resistant bacteria). Thus, in some embodiments of the devices and methods of the disclosure, the device produces a test signal in response to a test polynucleotide that differs sufficiently in comparison from the reference signal produced in response to a reference polynucleotide so that the test signal and be distinguished from the reference signal, permitting an instrument or user to distinguish between a test polynucleotide have a characteristic (e.g., presence of an allele) and a test polynucleotide not having that characteristic (e.g., absence of an allele). Without being bound by theory, the control probe may serve, in some embodiments, one or more of at least three roles: 1) to assure that the target (e.g., gyrA) amplicon was in fact generated by the device; 2) to permit a user (or the device itself) to compare signal intensity between the SNP-specific capture probe and the control capture probe in order to make a call: of "SNP present" or "SNP absent"; and 3) to serve to detection the presence of an organism (regardless of presence of absence of the SNP) (e.g., when the user does not intend to determine drug resistance but merely wishes to employ the device for detection of the pathogen).

In some embodiments, the first probe is characterized by a thermodynamic fulcrum and/or melting temperature of about 52° C.

In some embodiments, the first probe comprises between 12 and 25 nucleotides.

In some embodiments, the first probe comprises between 18 and 22 nucleotides.

In some embodiments, the first probe has a melting temperature of between 50° C. and 60° C.

In some embodiments, the first probe comprises, consists essentially of, or consists of a sequence selected from any one of SEQ ID NO: 13-19.

In some embodiments, the second probe comprises between 12 and 25 nucleotides.

In some embodiments, the second probe comprises between 18 and 22 nucleotides.

In some embodiments, the second probe has a melting temperature of between 50° C. and 60° C.

In some embodiments, the second probe comprises, consists essentially of, or consist of a sequence selected from any one of SEQ ID NO: 21 or 23.

In some embodiments, the molecular diagnostic device detects the allele in a biological sample comprising at least about 0.5 nM, at least about 1 nM, at least about 1.5 nM, at least about 2 nM, at least about 6 nM, at least about 8 nM, at least about 10 nM, or at least about 15 nM of the polynucleotide comprising the SNP locus if the SNP locus comprises the allele.

In some embodiments, the molecular diagnostic device determines whether a subject suspected of having a drug-sensitive bacterial infection has a drug-sensitive bacterial infection.

In some embodiments, the molecular diagnostic device determines whether a subject suspected of having a drug-resistant bacterial infection has a drug-resistant bacterial infection.

In another aspect, the disclosure a provides method, comprising a) introducing into any of the molecular diagnostic devices of the disclosure a biological sample from a subject having or suspected of having a disease or disorder characterized by one or more SNPs associated with susceptibility to a treatment, wherein the biological sample comprising a polynucleotide from the subject, b) administering the treatment if the molecular diagnostic device indicates the polynucleotide comprises a SNP locus comprising an allele associated with susceptibility to the treatment.

In some embodiments, the disease or disorder is a bacterial infection.

In another aspect, the disclosure a method, performed in a molecular diagnostic device comprising a sample preparation module configured to receive a biological sample, wherein the biological sample comprises a polynucleotide from a target bacteria; a reagent module containing a primer set targeting a single nucleotide polymorphism (SNP) locus in the polynucleotide; an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele; the method comprising amplifying a target amplicon from the polynucleotide from the target organism; optionally, amplifying a second target amplicon from the polynucleotide from the target organism; reacting the first target amplicon with a first probe to produce a first signal indicating susceptibility of the target organism to drug; optionally, reacting the first target amplicon with a second probe to produce a second signal indicating presence of the target organism in the biological sample and/or amplification of the target amplicon; and optionally, reacting the second target amplicon with a third probe to produce a third signal indicating presence of the target organism in the biological sample and/or amplification of either or both of the first target amplicon and the second target amplicon.

In some embodiments, the amplifying the first gene and the amplifying the second gene are performed simultaneously within a stand-alone device.

In some embodiments, the first signal, second signal, and/or third signal are produced without performing any melting curve analysis.

In some embodiments, the target organism is *Neisseria gonorrheae* (NG); the SNP locus is within the gyrA gene of NG; the amplifying the target amplicon comprises mixing a biological sample with a primer set designed to target a gyrA region; and thermal cycling the mixture of the biological sample and the primer set between a first temperature and a second temperature at a rate sufficient to produce the first target amplicon and optionally the second target amplicon.

In another aspect, the disclosure provides a method, performed in a molecular diagnostic device comprising a sample preparation module configured to receive a biological sample, wherein the biological sample comprises a polynucleotide from a target organism; a reagent module containing a primer set targeting a single nucleotide polymorphism (SNP) locus in the polynucleotide; an amplification module including a reaction volume and a heater, the reaction volume configured to receive the biological sample and an amplification solution comprising the primer set, the heater configured to convey thermal energy into the reaction volume to amplify the polynucleotide to produce an output containing a target amplicon comprising the SNP locus; and a detection module configured to receive the target amplicon, the detection module including a probe designed to bind to the SNP locus of the target amplicon if the SNP locus comprises a target allele, while minimizing binding to the SNP locus of the target amplicon if the SNP locus comprises an alternative allele; the method comprising: performing a molecular diagnostic test on the biological sample to determine A) the presence of a target organism and B) the presence of the target allele within the target organism that confers resistance to a first antibiotic; and administering, based on a result of the molecular diagnostic test, a second antibiotic.

Figure 15:
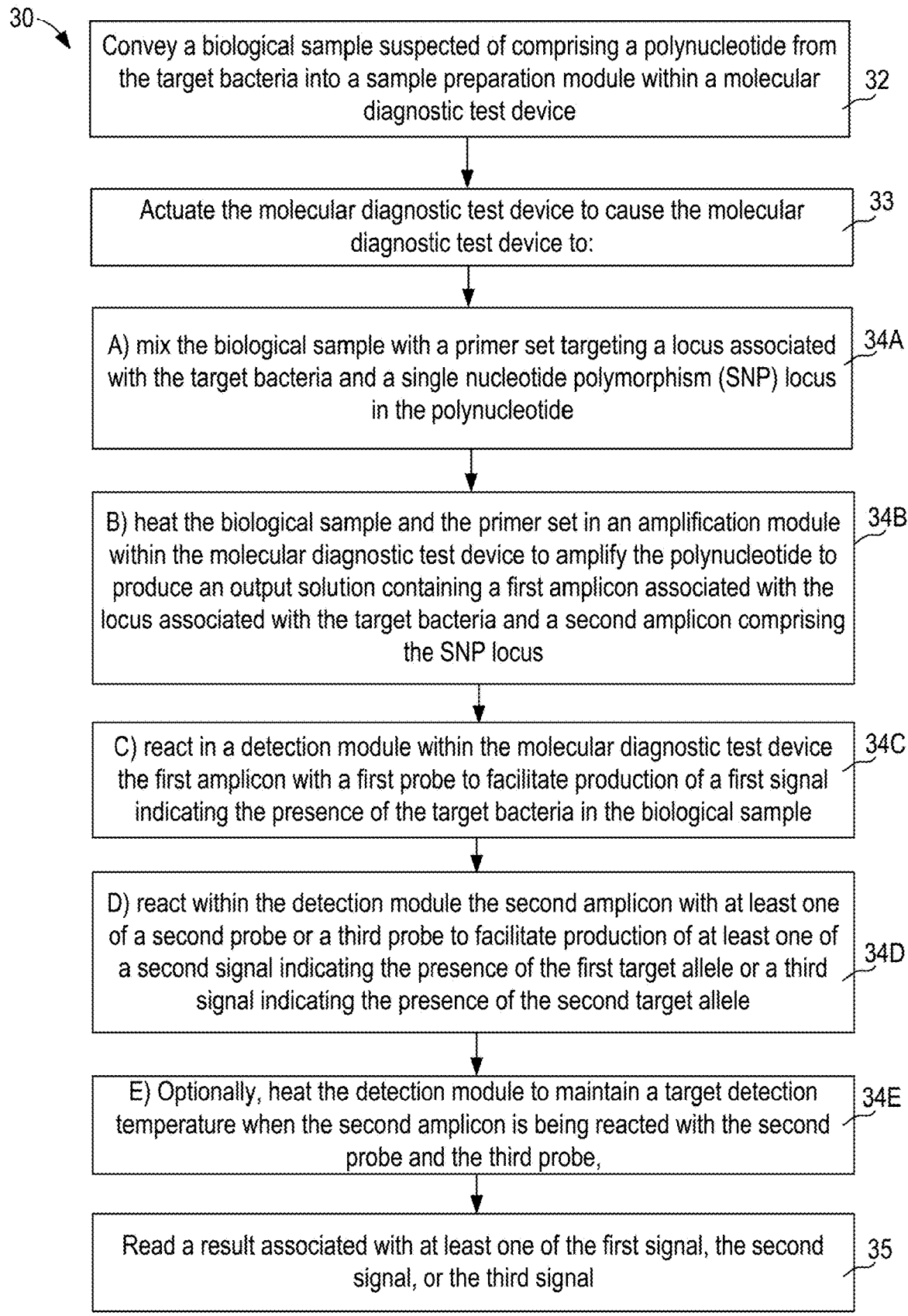
FIG. 15 is a flow chart of a method for detecting a target organism and whether the target organism is susceptible to a treatment regimen or resistant to the treatment regimen using a combined test, according to an embodiment.

FIG. 15 is a flow chart of a method 30 of detecting a target organism and whether the target organism is susceptible to a treatment regimen or resistant to the treatment regimen using a molecular diagnostic test device, according to an embodiment. The method 30 is described in connection with the molecular diagnostic test device 1000 (also referred to as a "test device" or "device") shown in in FIGS. 2-4. Although shown and described as being performed with the test device 1000, the method 30 and any of the methods described herein can be performed on any suitable molecular diagnostic device, such as any of the diagnostic devices shown and described herein or in International Patent Publication No. WO2016/109691, entitled "Devices and Methods for Molecular Diagnostic Testing," International Patent Publication No. WO2017/185067, entitled "Printed Circuit Board Heater for an Amplification Module," International Patent Publication No. WO2018/005870, entitled "Devices and Methods for Detection of Molecules Using a Flow Cell," International Patent Application No. PCT/US17/40112, entitled "Devices and Methods for Nucleic Acid Extraction," and International Patent Publication No. WO2019/060117, entitled "Portable Molecular Diagnostic Test Device and Methods for the Detection of Target Viruses," each of which is incorporated herein by reference in its entirety.

The method 30 includes conveying a biological sample suspected of comprising a polynucleotide from the target organism into a sample preparation module within the molecular diagnostic test device, at 32. The molecular diagnostic device can be the device 1000 and can include a sample preparation module, an amplification module and a detection module. The method further includes actuating the device, at 33. Actuation of the device causes the device to perform a series of operations to produce a result indicating whether the target organism is present and whether it is susceptible to a treatment regimen or resistant to the treatment regimen.

Specifically, the device mixes the biological sample with a primer set targeting a locus in a polynucleotide associated with the target organism and a single nucleotide polymorphism (SNP) locus in the polynucleotide, at 34A. The biological sample and the primer set are then healed in the amplification module to amplify the polynucleotide to produce an output solution containing a first amplicon associated with the locus in a polynucleotide associated with the target organism and a second amplicon comprising the SNP locus, at 34B. The device then reacts, in the detection module, the first amplicon with a first probe to facilitate production of a first signal indicating the presence of the target organism in the biological sample, at 34C. The second amplicon is reacted within the detection module with at least one of a second probe or a third probe to facilitate production of at least one of a second signal indicating the presence of a first target allele within the target organism associated with resistance to the treatment or a third signal indicating the presence of a second target allele within the target organism associated with susceptibility to the treatment, at 34D. The detection module can be an of the detection modules described herein. The first probe, the second probe, and the third probe can be any of the probes described herein.

In some embodiments, the device can optionally heat the detection module and the contents therein to maintain a target detection temperature when the second amplicon is being reacted with the second probe and the third probe, at 34E.

The method further includes reading a result associated with at least one of the first signal, the second signal, or the third signal. The reading can be performed by any of the methods described herein, and can be performed, for example, by visually inspecting a detection surface or electronically reading a detection surface.

In some embodiments, the detection module of the present invention do not contain a microarray or SNP array. The detection modules of the invention generally comprise at most ten detection surfaces. Some embodiments may have as many as twenty detection surfaces. Microarrays and SNP arrays and the like employ more probes and detection surfaces than the present devices. Generally a larger surface is required to accommodate a microarray or SNP array than provided by the present devices. Due to the smaller spot size used in microarrays and SNP arrays, the signal generated from them is much lower than generated by the present devices. Microarrays and SNP arrays are generally limited to fluorescent or radiographic detection to generate sufficient signal. The devices disclosed herein exclude the expensive and cumbersome detection methods used with arrays, such as lasers and radiosensitive film. By contrast, the present devices achieve detectable signal from comparatively low input amounts using detection methods that are, in some embodiments, inexpensive and/or compatible with single use.

In some embodiments, any of the devices described herein can include an electronic system that detects the presence of the colorimetric signals produced by the detection module therein (e.g., the detection module 1800, the detection module 4800, the detection module 5800, or any of the other detection modules described herein). Converting the color change produced by the chemical reactions into a digital result remove end-user ambiguity when interpreting test results. In some embodiments, the electronic system or a detection circuit therein can include one or more light emitting devices and one or more photodetectors and a computer-implemented module that determines a characteristic of the light associated with the detection surfaces of the detection module. For example, in some embodiments, a computer-implemented module can determine an amount of light attenuation through the detection surface(s). As the detection surface(s) changes color (as a result of the reactions described above), the amount of an incident light that passes through the detection surface will be reduced. By detecting the reduction in the light, the detection circuit can produce a digital signal that indicates the presence of the colorimetric signal produced by the detection surfaces.

Figure 16:
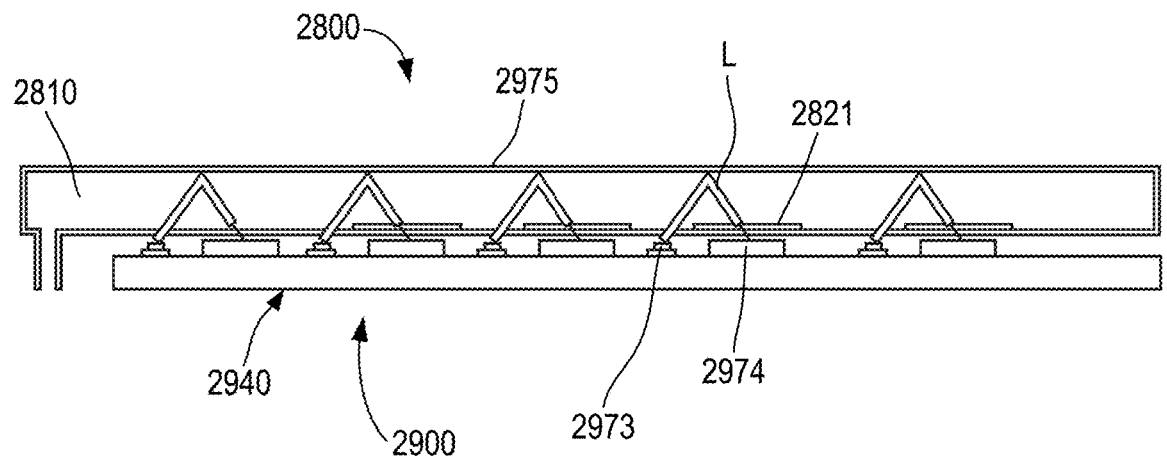
FIGS. 16 and 17 are schematic illustrations of a detection module and a portion of an electronic system of a molecular diagnostic test device, according to an embodiment.
Figure 17:
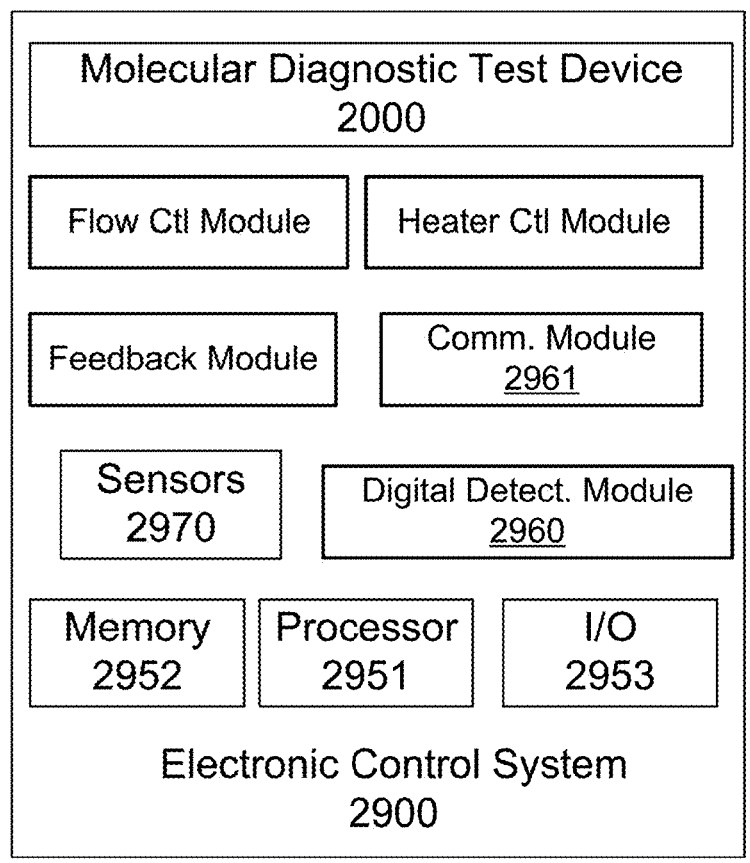

For example, FIGS. 16 and 17 are schematic illustrations of a portion of molecular diagnostic test device 2000 according to an embodiment that includes digital detection capability. The device 2000 includes a detection module 2800 and an electronic system 2950. Although not shown in FIGS. 16 and 17, the device 2000 can include any of the modules described herein, such as sample preparation module 4200, a reagent module 4700, and an amplification module 4600.

Similarly stated, the detection module 2800 and the electronic system 2900 can be included in any of the other test devices shown herein.

The detection module 2800 includes a flow cell 2810 that includes a set of detection surfaces 2821 (only one detection surface is identified in FIG. 16). The flow cell can be similar to the structure of the lid and the detection housing 4810 as shown above and the detection surfaces 2821 can be similar to any of the detection surfaces described above. For example, the detection surfaces 2821 can be correspond to the control detection surface 5824, the first detection surface 5821, the second detection surface 5822, and the third detection surface 5823 described herein, and can have probes adhered thereto. The probes can bind to target amplicon(s), as described herein, and subsequent reaction with one or more reagents can produce a colorimetric output (also referred to as a color signal) from one or more of the detection surfaces 2821.

The electronic system 2900 includes a printed circuit board 2940 and a series of light-emitting diodes (LEDs) 2973 and photodiodes 2974 (only one pair of LEDs and photodiodes is identified). The printed circuit board 2940 can be similar to or a portion of the printed circuit board/heater 4840 described above. In other embodiments, the printed circuit board 2940 can be similar to or a portion of the printed circuit board/heater 4630 described above. The printed circuit board 2940 can include a heater, a processor, and/or any other electrical components necessary for the detection module 2800 and the electronic system 2900 (or portions thereof) to operate as desired. For example, the electrical components can be resistors, capacitors, inductors, switches, microcontrollers, microprocessors and/or the like. Moreover, the detection circuit 2860 and the printed circuit board can be electrically coupled to a control module (or processor) for the overall device, such as the control module 4850 described above.

As shown, the LEDs and photodiodes are arranged on one side of the flow cell 2810, with one pair corresponding to each of the detection surfaces 2821. In this manner, when the LED is actuated, it will produce a light beam L that is reflected from the reflective member 2975 and back through the flow cell 2810 and detection surface 2821. The photodiode directly under the detection surface 2821 to be measured will receive the reflected light signal. By positioning the LEDs and photodiodes in the manner (e.g., with a photodiode directly under each detection surface), substantially all light detected by the photodiode will be from the light beam L that passes through the detection surface 2821. In this manner, when the target nucleic acid is present, it will bind to the probe (as described above). Addition of the reagent, which can be a precipitating substrate formulated to produce an insoluble colored particle when the reagent is contacted with a catalyzing agent, then produces a colored "spot" on the detection surface. As the reaction proceeds, the light beam from the LED will be attenuated as it passes through the spot, thereby yielding a reduced signal from the photodiode. Accordingly, by monitoring the signal from the photodiode, the digital detection module 2960 (described below) can determine when a color spot has sufficiently formed to produce a positive result.

The reflective member 2975 can be any suitable material coupled to the top of the flow cell 2810 (i.e., the side that opposite the printed circuit board). For example, in some embodiments, the reflective member 2975 can be planar, white material that reflects a high percentage of the incident light (from the LEDs) through the flow cell 2810 and the detection surface 2821. In some embodiments, the reflective member 2975 can be tuned to (or associated with) a particular light wavelength.

In some embodiments, the detection module 2800 can include any suitable shielding or light noise attenuation mechanisms to reduce light other than emitted by the desired LED 2973 from reaching the desired photodiode 2974. For example, in some embodiments, the detection module 2800 can include shield that surrounds the area associated with each of the detection surfaces 2821 between the bottom of the flow cell and the photodiode. In other embodiments, the detection module 2800 can include a cover or light shroud around substantially all of the detection module to reduce the likelihood that external light will impact the detection circuit 2860.

In yet other embodiments, the detection circuit 2860 actuates (or applies power to) only one LED at a time. In this manner, light from an adjacent LED will not affect the photodiode signal associated with a particular detection surface 2821. Specifically, the detection circuit 2860 can multiplex the readings by continuously cycling through each pair of photodiodes and LEDs. The cycling frequency can be any suitable value, and can be selected to accurately assess the rate of formation of the color spot.

In other embodiments, the LEDs 2973 and photodiodes 2974 can be arranged in any suitable configuration. Moreover, although the detection circuit 2860 is shown as having a photodiode underneath (or aligned with) the detection surface 2821 and the LED offset from the detection surface, in other embodiments, the LED can be aligned with the detection surface 2821 and the photodiode can be offset from the detection surface 2821. In other embodiments, a detection circuit can include one LED for each detection surface but only one photodiode (or light detection device) that detects light. In such embodiments, the detection module can include a scattering mechanism (not shown) that scatters a portion of the light towards the photodiode where each LED is producing the light when powered separately from other LEDs. In other embodiments, a detection circuit can include one photodiode under each of the detection surfaces but only one LED. In such embodiments, the detection module can include a scattering mechanism (not shown) that shines the light from the single LED incident upon all of the detection surfaces. Such embodiments would be well-suited for reading from all photodiodes simultaneously.

Although the detection module 2800 is shown as including both the LEDs 2973 and the photodiodes 2974 on one side of the flow cell and a reflective member 2975 on the other side, in other embodiments, a detection circuit can include an LED on one side of the flow cell 2810 and the photodiode directly opposed, on the other side of the flow cell 2810.

As described above, in some embodiments, the use of shielding and/or alignment can reduce light noise and can also limit part-to-part variability. Accordingly in some embodiments, the printed circuit board 2940 can include one or more alignment features (e.g., pins, protrusions, openings) that facilitate alignment with the flow cell 2810. In this manner, the detection surfaces 2821 can be aligned with the LED/photodiode pairs.

FIG. 17 is a schematic illustration of the molecular diagnostic test device 2000, showing various hardware and software modules of the electronic system 2900, including the digital detection module 2960. As noted above, the molecular diagnostic test device 2000 can be any of the molecular diagnostic test devices described herein. The molecular diagnostic test device 2000 can be a stand-alone device similar to the molecular diagnostic test device 4000 described herein. The molecular diagnostic test device 2000 includes or is attached to the electronic control system 2900. In some embodiments, the electronic control system 2900 can be coupled to and/or within a housing of the molecular diagnostic test device 2000, and can include one or more printed circuit boards, processors, and/or subsystems. For example, the electronic control system 2900 can include the amplification module printed circuit board heater 4630 (including the electronic control module/processor 4950), the detection module heater 4840, and the printed circuit board 2940. The electronic control system 2900 includes at least one processor 2951, at least one memory 2952, one or more sensors (collectively identified as 2970), and an input/output subsystem 2953. The electronic control system 2950 also includes a communication module 2961 and a digital detection module 2960. The electronic control system 2950 also includes other modules for controlling the device (e.g., a flow control module, a heater control module, and a feedback module. Although shown as including each of these application modules, in other embodiments, an electronic control system need not include all (or any) of these modules, and can include any other modules described herein.

The processor 2951, and any of the processors described herein can be any suitable processor for performing the methods described herein. In some embodiments, processor 2951 can be configured to run and/or execute application modules, processes and/or functions associated with the molecular diagnostic test device 2000. For example, the processor 2951 can be configured to run and/or execute the communication module 2961, the digital detection module 2960, and/or any of the other modules described herein, and perform the methods associated therewith. The processor 2951 can be, for example, a Field Programmable Gate Array (FPGA), an Application Specific Integrated Circuit (ASIC), a Digital Signal Processor (DSP), and/or the like. The processor 2951 can be configured to retrieve data from and/or write data to memory, e.g., the memory 2952.

The memory 2952 can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. In some embodiments, the memory 2952 stores instructions to cause the processor 2951 to execute modules, processes and/or functions associated with the molecular diagnostic test device 2000. For example, the memory 2952 can store instructions to cause the processor 2951 to execute any of the application modules described herein, and perform the methods associated therewith.

The sensor(s) 2970 included within the electronic control system 2950 can include any number of switches, optical/light input sensors, temperature sensors, contact sensors, and/or any other suitable input device. The sensor(s) 2970 can include any of the sensors described herein. Specifically, the sensor(s) 2970 can include one or more pairs of LEDs 2973 and photodiodes 2974, as described above.

The input/output subsystem 2953 (which functions as a user interface) can include any suitable components for conveying information to, and in some embodiments, receiving information from, a user. For example, in some embodiments, the input/output subsystem 2953 can include one or more light output devices (e.g., LEDs) that produce a light signal that can be easily seen by the user to read the device. For example, in some embodiments, the input/output subsystem 2953 can include a red LED that emits red light from an opening in the device housing when an invalid test has occurred (e.g., when no signal is detected from the control detection surface, see, e.g., the first condition shown in FIG. 14). The input/output subsystem 2953 can also include a green LED that emits green light from an opening in the device housing when a signal from the control detection surface has been detected, indicating that a valid test has occurred (see. e.g., the second-fifth conditions shown in FIG. 14).

In some embodiments, the input/output subsystem 2953 can include LEDs that are aligned with one of the control windows or control openings defined by the housing. For example, referring to FIGS. 6 and 7, the input/output subsystem 2953 can include LEDs aligned with each of the openings 4011 corresponding to one of the conditions to be detected by the test device. For example, the input/output subsystem 2953 can include an LED positioned to emit light through the opening adjacent the "target organism" indicium on the housing 4010. Thus, when the digital detection module 2960 detects the presence of a signal from the detection surface from which a colorimetric signal is produced when the target organism is present in the biological sample, the LED will emit light adjacent the "target organism" indicium on the housing 4010. For example, when any of the third through fifth conditions shown in FIG. 14 occur, the LED will emit light adjacent the "target organism" indicium.

The input/output subsystem 2953 can include an LED positioned to emit light through the opening adjacent the "drug resistant" indicium on the housing 4010. Thus, when the digital detection module 2961 detects the presence of a signal from the detection surface from which a colorimetric signal is produced when the —R allele is present in the biological sample, the LED will emit light adjacent the "drug resistant" indicium on the housing 4010. For example, when the fourth condition shown in FIG. 14 occurs, the LED will emit light adjacent the "drug resistant" indicium. The input/output subsystem 2953 can include an LED positioned to emit light through the opening adjacent the "susceptible to drug" indicium on the housing 4010. Thus, when the digital detection module 2960 detects the presence of a signal from the detection surface from which a colorimetric signal is produced when the —S allele is present in the biological sample, the LED will emit light adjacent the "susceptible to drug" indicium on the housing 4010. For example, when the fifth condition shown in FIG. 14 occurs, the LED will emit light adjacent the "susceptible to drug" indicium.

In other embodiments, the input/output subsystem 2953 can produce any suitable electronic output to be read by the user. Such electronic outputs can include an audible output (e.g., produced by a speaker), a haptic (vibratory) output, a light output (e.g., as described herein), and a wireless signal.

In some embodiments, the input/output subsystem 2953 can include a monitor or screen that displays visual elements to a user. The screen can be a touch screen upon which a series of graphical user interface elements (e.g., windows, icons, input prompts, graphical buttons, data displays, notification, or the like) can be displayed. In some embodiments, the graphical user interface elements (not shown) are produced by a user interface module. In such embodiments, the user can also enter information into the electronic system 2900 via the input/output subsystem 2953.

The communication module 2961 can be a hardware and/or software module (stored in memory 2952 and/or executed in the processor 2951). The communication module 2961 is configured to receive an indication (e.g., from the sensor(s)) and/or test result information from the digital detection module 2960 and transmit an output signal associated with the test result. The output signal(s) are produced to the user via the input/output subsystem 2953, as described above.

Figure 18:
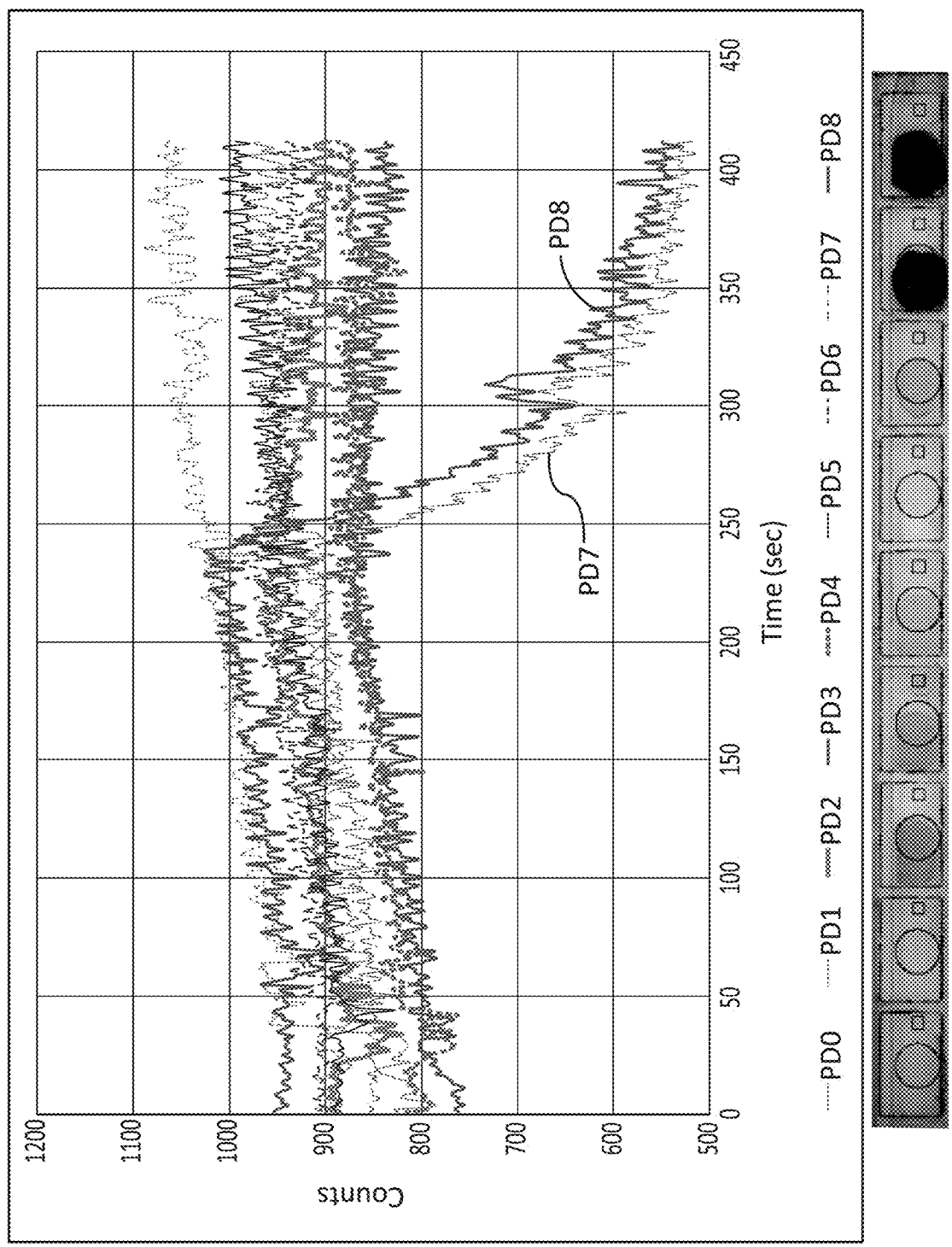
FIG. 18 is a plot showing a series of light signals (each corresponding to a detection surface) produced by an electronic system of a molecular diagnostic test device, according to an embodiment.

The digital detection module 2960 can be a hardware and/or software module (stored in memory 2952 and/or executed in the processor 2951). The digital detection module 2960 is configured to receive a signal (e.g., from one or more photodiodes 2974) and determine, based on the signal, whether a color signal from the corresponding detection surface is present. Functions of the digital detection module 2960 are described with respect to the plots shown in FIGS. 18 and 19 and the flow chart shown in FIG. 20. FIG. 18 is a plot showing a series of light signals (each corresponding to a detection surface 2821) produced by an electronic system (e.g., the electronic system 2900) of a molecular diagnostic test device (e.g., the device 2000) as a function of time. Specifically, FIG. 18 shows nine different light signals (in units of raw voltage counts), each corresponding to a different photodetector adjacent a detection surface (identified as photodetectors PD0 through PD8). As described herein, when the reagent (e.g., the substrate) is introduced into the detection module, a colorimetric signal (referred to as a "color spot") will form on those detection surfaces to which the target amplicon(s) have been bound by the capture probe. FIG. 18 shows a very strong color signal on the detection surfaces associated with photodetectors PD7 and PD8. Because the light beam L (see FIG. 16) is attenuated by the strong color, the light signals for PD7 and PD8 drop significantly as the color is formed. Because the colorimetric signals take time to form on the detection surface, the reduction in the light signal is not instantaneous, but occurs over time after the introduction of the reagent (which occurs at about a time of 250 seconds).

The presence of a color signal from other detection surfaces, however, is not as readily apparent. For example, the detection surfaces associated with photodetectors PD2, PD3, PD4, and PD6 appear to show some level of color, possibly indicating the presence of the target amplicon(s). Such low levels of color could be the result of a low concentration of the polynucleotide. The digital detection module 2960 can employ any suitable algorithm to accurately and repeatably detect the presence of a colorimetric signal from the detection surfaces. In some embodiments, the digital detection module 2960 can subtract a background measurement taken through a "background" portion of the detection module 2800 where no colorimetric signal is formed. The digital detection module 2960 can then receive a light signal associated with a detection surface over a period of time (i.e., after the introduction of the reagent) and produce an output indicating the presence of a color signal if the value of the light signal drops below a predetermined threshold. In some embodiments, the digital detection module 2960 can indicate the presence of a color signal when the value of the light signal decreases by more than a threshold amount (e.g., measured either as an amount of raw counts or voltage, or in other embodiments, as a percentage drop in the light signal). In some embodiments, for example, the digital detection module 2960 can indicate the presence of a color signal when the value of the light signal decreases by at least 25 percent over a predetermined time period.

Figure 19:
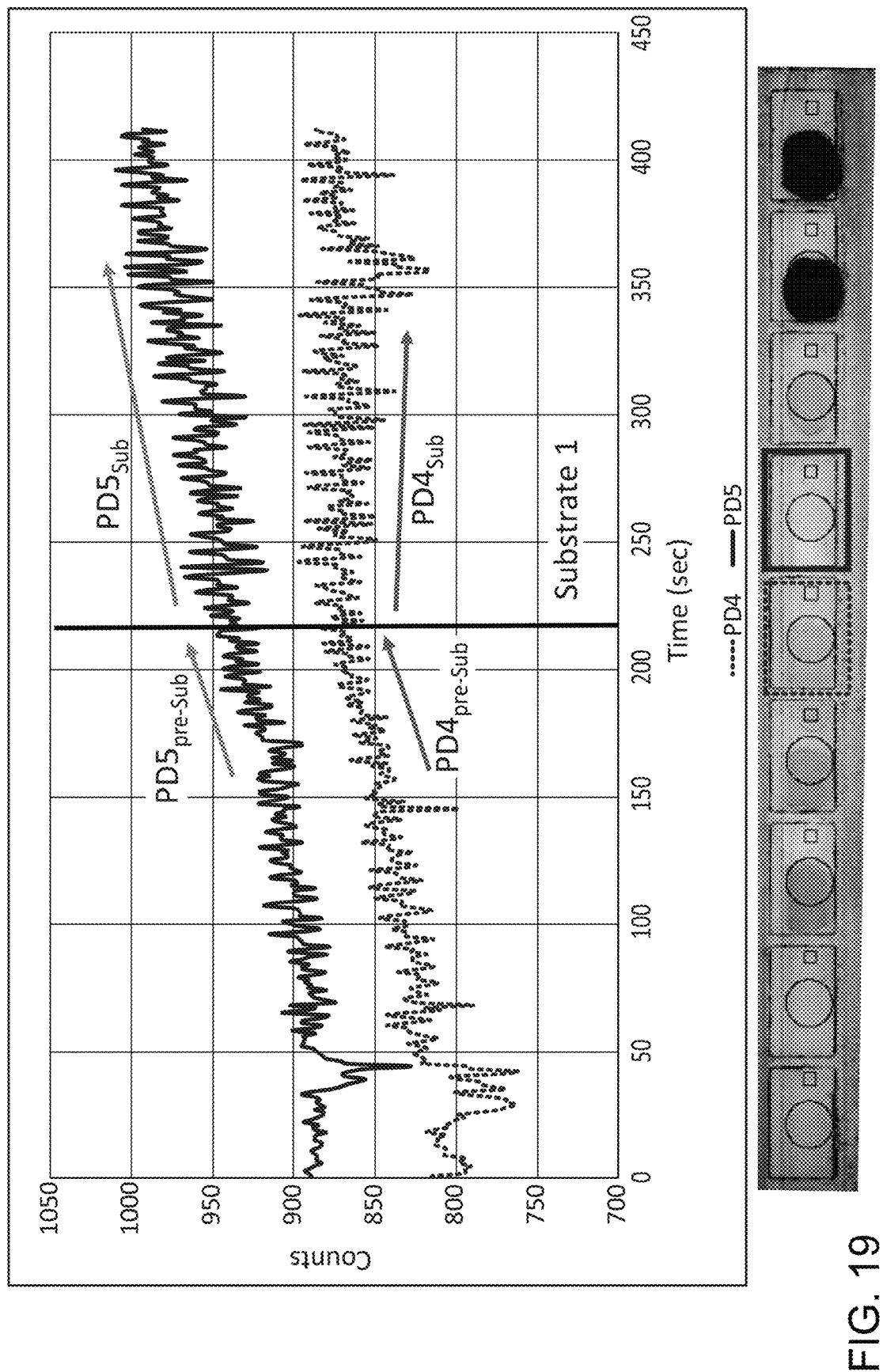
FIG. 19 is a plot showing two of light signals (each corresponding to a detection surface) to illustrate a digital detection algorithm according to an embodiment.

In other embodiments, the detection module 2960 can determine the presence of a color signal based on the slope (or rate of change) of the light signal from the photodetector. Because the intensity of the measured light beam is a function of the temperature of the LED 2973 and/or the photodiode 2974, in the absence of any color the magnitude of the light signal is not constant. Specifically, as shown in FIGS. 18 and 19, because device 2000 is generally cooling down during the detection operation (due to the completion of the amplification heating), the light signals generally increase as a function of time. In some embodiments, the detection module 2960 first determines a baseline slope of the light signal during the time period before the substrate is introduced into the flow cell. This is shown in FIG. 19 as the slopes identified as $PD4_{pre-sub}$ and $PD5_{pre-sub}$. Because device 2000 is cooling, the slope during this time period is generally positive (reflecting an increase in the light signal). The detection module 2960 then determines a slope of each light signal during the time period after the substrate is introduced into the flow cell. This is shown in FIG. 19 as the slopes identified as $PD4_{sub}$ and $PD5_{sub}$. If there is little attenuation (as shown for PD5), the light signal will continue to increase, and the slope $PD5_{sub}$ will remain positive. If, however, a color spot begins to form on the detection surface (as shown for PD4), the slope will decrease, and often become negative (as shown by the slope $PD4_{sub}$). The digital detection module 2960 can produce an output indicating the presence of a color signal if the value of the slope of the light signal drops below a predetermined threshold (or decreases from its starting amount by more than a predetermined amount or percentage). In other embodiments, the digital detection module 2960 can produce an output indicating the presence of a color signal if the value of the slope of the light signal decreases by more than a threshold amount. For example, in some embodiments, the digital detection module 2960 can produce an output indicating the presence of a color signal if the difference between the slope of the light signal during the second time period (i.e. after conveying the substrate) and the slope of the light signal during the first time period (i.e. before conveying the substrate) exceeds a threshold value.

Figure 20:
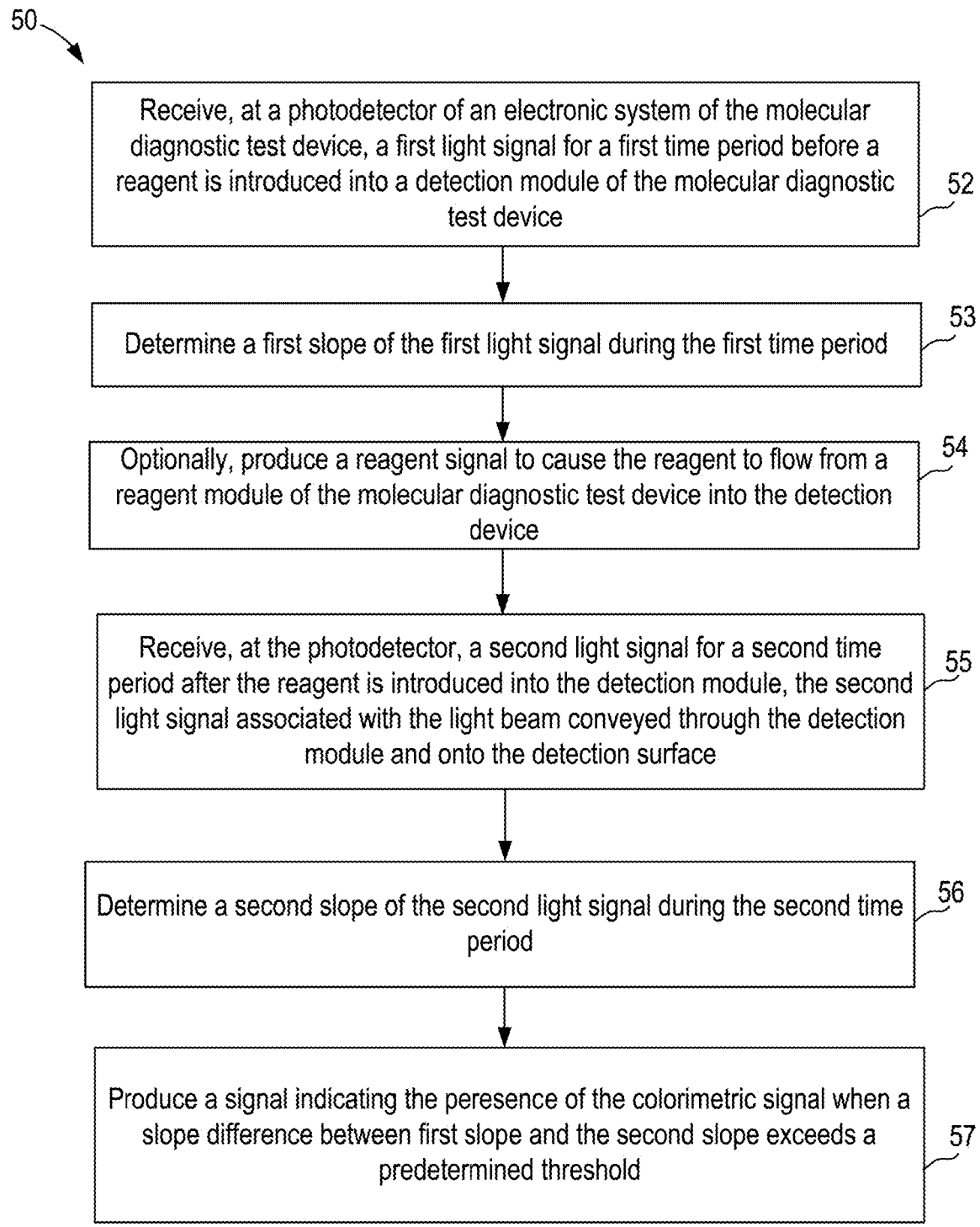
FIG. 20 is a flow chart of a method for detecting the presence of a colorimetric signal, according to an embodiment.

FIG. 20 is a flow chart of a computer-related method 50 of detecting a target organism and whether the target organism is susceptible to a treatment regimen or resistant to the treatment regimen using a molecular diagnostic test device, according to an embodiment. The method 50 is described in connection with the molecular diagnostic test device 2000 (also referred to as a "test device" or "device") shown in in FIGS. 16-17. Although shown and described as being performed with the test device 2000, the method 50 and any of the methods described herein can be performed on any suitable molecular diagnostic device, such as any of the diagnostic devices shown and described herein or in International Patent Publication No. WO2016/109691, entitled "Devices and Methods for Molecular Diagnostic Testing," International Patent Publication No. WO2017/185067, entitled "Printed Circuit Board Heater for an Amplification Module," International Patent Publication No. WO2018/005870, entitled "Devices and Methods for Detection of Molecules Using a Flow Cell," International Patent Application No. PCT/US17/40112, entitled "Devices and Methods for Nucleic Acid Extraction," and International Patent Publication No. WO2019/060117, entitled "Portable Molecular Diagnostic Test Device and Methods for the Detection of Target Viruses," each of which is incorporated herein by reference in its entirety.

The method 50 includes receiving, at a photodetector of an electronic system of the molecular diagnostic test device, a first light signal for a first time period before a reagent is introduced into a detection module of the molecular diagnostic test device, at 52. The molecular diagnostic device can be the device 2000 and the electronic system can be the electronic system 2900, which includes the digital detection module 2960. A first slope (i.e., rate of change) of the first light signal during the first time period is determined, at 53. The determining the first slope can be performed by a digital detection module, similar to the digital detection module 2960 described above. The digital detection module can perform any suitable digital filtering, data smoothing, or other processes to manipulate the light signal (e.g., similar to the light signals shown in FIGS. 17 and 18) to determine the first slope.

In some embodiments, the electronic system can also control operations of the device, such as the heating (for amplification), the flow module (to move the biological sample and/or reagents within the device), and the detection operation. For example, in some embodiments, the method 50 optionally includes producing a reagent signal to cause the reagent to flow from a reagent module of the molecular diagnostic test device into the detection device, at 54. The reagent signal can be, for example, a signal to a valve (e.g., the valve 4340) and/or the fluidic drive module (e.g., the fluidic drive module 4400) to cause a detection reagent to be conveyed from the reagent storage module (e.g., the reagent storage module 4700) into the detection module.

The method 50 further includes receiving, at the photodetector, a second light signal for a second time period after the reagent is introduced into the detection module, at 55. The second light signal associated with the light beam conveyed through the detection module and onto the detection surface. A second slope (i.e., rate of change) of the second light signal during the second time period is determined, at 56. The determining the second slope can be performed by a digital detection module, similar to the digital detection module 2960 described above. The digital detection module can perform any suitable digital filtering, data smoothing, or other processes to manipulate the light signal (e.g., similar to the light signals shown in FIGS. 17 and 18) to determine the second slope.

A signal indicating the presence of the colorimetric signal is produced when a slope difference between first slope and the second slope exceeds a predetermined threshold, at 57.

In addition to accurately determining the presence of a color signal from each of the detection surfaces, in some embodiments, the digital detection module 2960 evaluates the signal(s) produced by each of the series of detection surfaces (see, e.g., the detection surfaces 5821, 5822, 5823, and 5824 in FIG. 14) to produce a "yes/no" decision for whether the target organism (e.g., NG) is present and whether it is susceptible to a treatment regimen (e.g., NG that is susceptible to ciprofloxacin). In this manner, the digital detection module 2960 can eliminate user subjectivity from interpreting test results, which can potentially produce errors when the detection surfaces produce a low color output. (i.e., a lightly-colored signal, such as the signal identified as PD4 in FIG. 19).

In some embodiments, the digital detection module can evaluate difference between a light signal associated with the detection surface for the —S allele and the —R allele and determined, based on the difference whether the test result should identify the organism strain as either "susceptible" or "resistant." For example, when evaluating for the presence and treatment for NG, when the detection module 2800 (and the associated methods) detects NG, the standard of care for $CIP^R$ should be applied unless there is a very high certainty that the NG strain is susceptible to the alternative treatment (ciprofloxacin). Thus in instances where both the detection surface for the —R allele (e.g., the second detection surface 5822 shown in FIG. 14) and the detection surface for the —S allele (e.g., the third detection surface 5823 shown in FIG. 14) are very light signals, the test should produce a result prescribing the standard of care (e.g., CRO+AZI). Thus, in some embodiments, the digital detection module 2960 can evaluate a difference between or a ratio between the light signals associated with the detection surfaces.

Figure 21:
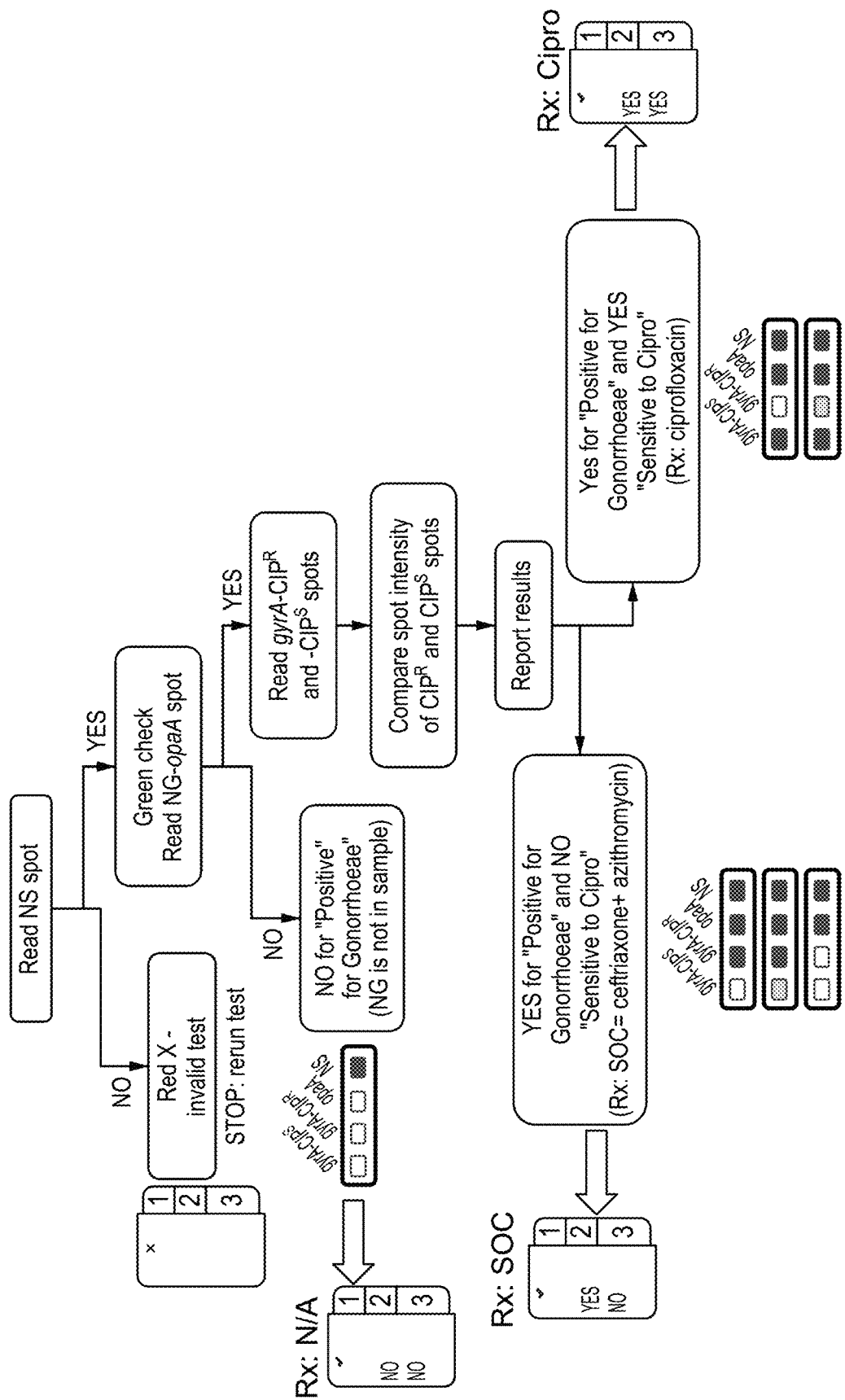
FIG. 21 is a schematic illustration of a method detecting NG and whether the NG is susceptible to a treatment regimen or resistant to the treatment regimen using a combined test, according to an embodiment.

FIG. 21 is a schematic diagram of an algorithm of determining whether NG is present and whether the strain of NG (if present) is susceptible to or resistant to ciprofloxacin according to an embodiment. As shown, if the NS spot is undetectable the device will return a red X, indicating that the test is invalid. If the NS spot is present, the digital detection algorithm proceeds to evaluate the opA spot. (Step 2: Read opaA spot). If the opaA spot is absent, the device returns a green check indicating that the test was valid and that the sample is negative for NG. The user will see a NO/NO result for "Positive for Gonorrhoeae"/"Sensitive to Ciprofloxacin." If, however, the opaA spot is present, the digital detection algorithm proceeds to evaluate the gyrA-CIPR and -CIPS spots. (Step 3: Read and compare gyrA-CIPR and -CIPS spot intensity). If the gyrA-CIPS spot is either absent or of a lower intensity than the gyrA-CIPR spot, the device will return a green check indicating a valid test along with an output indicating YES/NO (meaning that the "standard of care" is the recommended treatment). Additionally, if both gyrA-CIPR and -CIPS spots are absent (or the same intensity), the result will also be YES/NO. Biasing the call logic in this manner, ensures that all patients that test positive for NG receive the most conservative treatment, ensuring that a patient presenting with a low microbial load of cipro-R strain is not treated with ciprofloxacin (minimizing false positives). If the gyrA-CIPR spot is either absent or lower intensity that gyrA-CIPS probe, the device will return a green check indicating a valid test along with an output indicating YES/YES (meaning that the recommended treatment is ciprofloxacin).

Any of the sample input modules, sample preparation modules, amplification modules, heater assemblies, and detection modules shown and described herein can be used in any suitable diagnostic device. Such devices can include, for example, a single-use device that can be used in a point-of-care setting and/or in a user's home. Similarly stated, in some embodiments, the device (and any of the other devices shown and described herein) can be configured for use in a decentralized test facility. Further, in some embodiments, any of the sample input modules, sample preparation modules, amplification modules, heater assemblies, and detection modules shown and described herein can be included within a CLIA-waived device and/or can facilitate the operation of a device in accordance with methods that are CLIA waived. Similarly stated, in some embodiments, the sample input modules, the sample preparation modules, the amplification modules, and the detection modules shown and described herein can facilitate operation of a device in a sufficiently simple manner that can produce results with sufficient accuracy to pose a limited likelihood of misuse and/or to pose a limited risk of harm if used improperly. In some embodiments, the sample input modules, the sample preparation modules, the amplification modules, and the detection modules shown and described herein can be used in any of the diagnostic devices shown and described in International Patent Publication No. WO2016/109691, entitled "Devices and Methods for Molecular Diagnostic Testing," which is incorporated herein by reference in its entirety.

Although the amplification modules are generally described herein as performing a thermal cycling operation on the prepared solution, in other embodiment, an amplification module can perform any suitable thermal reaction to amplify nucleic acids within the solution. In some embodiments, any of the amplification modules described herein can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process The devices and methods described herein can be used to analyze any suitable type of biological sample, such as a tissue sample (e.g., a blood sample). In some cases, the biological sample comprises a bodily fluid taken from a subject. In some cases, the bodily fluid includes one or more cells comprising nucleic acids. In some cases, the one or more cells comprise one or more microbial cells, including, but not limited to, bacteria, archaebacteria, protists, and fungi. In some cases, the biological sample includes one or more virus particles. In some cases, the biological sample includes one or more microbes that causes a sexually-transmitted disease. A sample may comprise a sample from a subject, such as whole blood; blood products; red blood cells; white blood cells; buffy coat; swabs; urine; sputum; saliva; semen; lymphatic fluid; endolymph; perilymph; gastric juice; bile; mucus; sebum; sweat; tears; vaginal secretion; vomit; feces; breast milk; cerumen; amniotic fluid; cerebrospinal fluid; peritoneal effusions; pleural effusions; biopsy samples; fluid from cysts; synovial fluid; vitreous humor; aqueous humor; bursa fluid; eye washes; eye aspirates; plasma; serum; pulmonary lavage; lung aspirates; animal, including human, tissues, including but not limited to, liver, spleen, kidney, lung, intestine, brain, heart, muscle, pancreas, cell cultures, as well as lysates, extracts, or materials and fractions obtained from the samples described above or any cells and microorganisms and viruses that may be present on or in a sample. A sample may include cells of a primary culture or a cell line. Examples of cell lines include, but are not limited to 293-T human kidney cells, A2870 human ovary cells, A431 human epithelium, 1335 rat neuroblastoma cells, BHK-21 hamster kidney cells, BR293 human breast cells, CHO Chinese hamster ovary cells, CORL23 human lung cells, HeLa cells, or Jurkat cells. The sample may include a homogeneous or mixed population of microbes, including one or more of viruses, bacteria, protists, monerans, chromalveolata, archaea, or fungi. The biological sample can be a urine sample, a vaginal swab, a cervical swab, an anal swab, or a cheek swab. The biological sample can be obtained from a hospital, laboratory, clinical or medical laboratory.

In some embodiments, a method includes detecting, from a sample, an infecting microbe and a SNP that is associated with (or that determines) the antimicrobial susceptibility. Such samples can include, for example, blood, urine, sputum, cerebral spinal fluid, joint fluid, feces, pus, tissue, and swabs from urogenital sites, rectum, pharynx (and nasal pharynx), and conjunctivae.

The devices and methods described herein, however, are not limited to performing a molecular diagnostic test on human samples. In some embodiments, any of the devices and methods described herein can be used with veterinary samples, food samples, and/or environmental samples. Examples of environmental sources include, but are not limited to agricultural fields, lakes, rivers, water reservoirs, air vents, walls, roofs, soil samples, plants, and swimming pools. Examples of industrial sources include, but are not limited to clean rooms, hospitals, food processing areas, food production areas, food stuffs, medical laboratories, pharmacies, and pharmaceutical compounding centers. Examples of subjects from which polynucleotides may be isolated include multicellular organisms, such as fish, amphibians, reptiles, birds, and mammals. Examples of mammals include primates (e.g., apes, monkeys, gorillas), rodents (e.g., mice, rats), cows, pigs, sheep, horses, dogs, cats, or rabbits. In some examples, the mammal is a human. Further, the sample of the present invention is not limited to biological samples, the sample of the present invention may be environmental (air, water, soil, etc.), animal (see above), or plant (e.g., cells obtained from any portion of a plant where the species of plant is without limit).

In some embodiments, the sample is a processed or unprocessed food product. In other aspects, the food sample comprises at least one of meat, turkey, chicken and other poultry, milk, eggs, eggs products, dairy products, fresh or dried fruits and vegetables and their juices, grains, fish, seafood, pet food, baby food and infant formula. In another embodiment, the sample is a bacterial isolate, to confirm or identify the strain and its antibacterial resistance profile. It is anticipated that the organism-specific and antibiotic resistance (AR) probes in an array system can be used as a clinical diagnostics tool in hospitals, to aid in epidemiological research and tracking as well as for infection control.

In some embodiments, any of the amplification modules described can be configured to conduct a "rapid" PCR (e.g., completing at least 30 cycles in less than about 10 minutes), and rapid production of an output signal (e.g., via a detection module). Similarly stated, the amplification modules described herein can be configured to process volumes, to have dimensional sizes and/or be constructed from materials that facilitates a rapid PCR or amplification in less than about 10 minutes, less than about 9 minutes, less than about 8 minutes, less than about 7 minutes, less than about 6 minutes, or any range therebetween, as described herein.

In some embodiments, any of the devices and methods described herein can be a "rapid" PCR (e.g., completing at least 30 cycles in less than about 10 minutes) that provides sample-to-answer capability, without the need for an external instrument, in about 27 minutes, 25 minutes, 22 minutes, 20 minutes, or less. Similarly stated, the device can be a stand-alone device that does not require any external instrument to add reagents, manipulate actuators, mix constituents, or read the test result. In some embodiments, the device can be connected to an external power source (e.g., an A/C power source, which is not considered to be an "external instrument.").

In some embodiments, any of the amplification modules described herein can be configured to conduct RT-PCR. In some embodiments, the methods described herein comprise conducting RT-PCR. In some embodiments, the RT-PCR method is a one-step assay. One-step assays combine reverse transcription and PCR in a single tube and buffer using reverse transcriptase and DNA polymerase. In some embodiments, the RT-PCR method is a two-step assay. In two-step assays, reverse transcription and PCR steps are performed in separate tubes. RT-PCR methods utilize the enzyme reverse transcriptase to reverse transcribe RNA to cDNA. In some embodiments, the reverse transcriptase is thermostable. Suitable reverse transcriptases include viral, retroviral and bacterial enzymes. For example, the reverse transcriptase may be: Moloney Murine Leukemia Virus (M-MLV) RT, Human Immunodeficiency Virus (HIV) RT, Avian Sarcoma-Leukosis Virus (ASLV) RT, Rous Sarcoma Virus (RSV) RT, Avian Myeloblastosis Virus (AMV) RT, Avian Erythroblastosis Virus (AEV) Helper Virus MCAV RT, Avian Myelocytomatosis Virus MC29 Helper Virus MCAV RT, Avian Reticuloendotheliosis Virus (REV-T) Helper Virus REV-A RT, Avian Sarcoma Virus UR2 Helper Virus UR2AV RT, Avian Sarcoma Virus Y73 Helper Virus YAV RT, Rous Associated Virus (RAV) RT, and Myeloblastosis Associated Virus (MAV) RT. In some embodiments, the template for reverse transcription is total RNA. In some embodiments, the template for reverse transcription is mRNA.

In some embodiments, any of the amplification modules described herein can be configured to conduct real-time polymerase chain reaction (qPCR) combined with RT-PCR. This technique is called qRT-PCR. In some embodiments, the methods described herein comprise conducting qRT-PCR. In some embodiments, the methods described herein comprise conducting qRT-PCR. In some embodiments, the qRT-PCR method is a one-step assay. One-step assays combine reverse transcription and PCR in a single tube and buffer using reverse transcriptase and DNA polymerase. In some embodiments, the qRT-PCR method is a two-step assay. In two-step assays, reverse transcription and PCR steps are performed in separate tubes. qRT-PCR methods utilize the enzyme reverse transcriptase to reverse transcribe RNA to cDNA. In some embodiments, the reverse transcriptase is thermostable. Suitable reverse transcriptases include viral, retroviral and bacterial enzymes. For example, the reverse transcriptase may be: Moloney Murine Leukemia Virus (M-MLV) RT, Human Immunodeficiency Virus (HIV) RT, Avian Sarcoma-Leukosis Virus (ASLV) RT, Rous Sarcoma Virus (RSV) RT, Avian Myeloblastosis Virus (AMV) RT, Avian Erythroblastosis Virus (AEV) Helper Virus MCAV RT, Avian Myelocytomatosis Virus MC29 Helper Virus MCAV RT, Avian Reticuloendotheliosis Virus (REV-T) Helper Virus REV-A RT, Avian Sarcoma Virus UR2 Helper Virus UR2AV RT. Avian Sarcoma Virus Y73 Helper Virus YAV RT, Rous Associated Virus (RAV) RT, and Myeloblastosis Associated Virus (MAV) RT. In some embodiments, the template for reverse transcription is total RNA. In some embodiments, the template for reverse transcription is mRNA.

In some embodiments, any of the devices and methods described herein (and the methods can be performed rapidly: an integrated sample-to-result requiring only 10 to 15 seconds of hands-on time, giving a test result in less than about 25 minutes. The device and methods described herein are accurate and use the same PCR technology as market leading laboratory-based systems. The device and methods described herein allow for simultaneous detection of multiple pathogens. The device and methods described herein are single-use/disposable tests that eliminate instrument cleaning, servicing, and decontamination. The device and methods described herein are applicable for unlimited surge testing—one or many tests can be performed simultaneously/asynchronously.

In some embodiments, any of the devices described herein can be shelf-stable. Specifically, the devices described herein can have no special temperature or humidity requirements for transport and storage, thus easing stockpiling.

Any of the devices described herein can be easily and portably powered. Any of the devices can be powered by a wall adapter or battery, and are thus ideal for field use.

In some embodiments, a method of detection of NG and other STI's can be performed on a stand-alone device. The device is configured to detect (and the method includes detection of) all FDA required strains (70 strains of NG, 16 strains of CT, and 31 strains of TV). Moreover, the device (and the methods) have no cross-reactivity against 142 strains of phylogenetically related non-STI organisms typically found in the urogenital tract. The device is capable of, and the methods include detection of low concentrations of CT (50-150 EB/ml), NG (50-150 cfu/ml), and TV (20 trophs/ml) typically found in patients with low microbial loads. For example, certain test results from 79 patient samples containing CT or NG, and 78 samples containing TV showed a sensitivity of 100% across all pathogens, and a specificity of 98% for CT and NG, and 94% for TV as compared to an FDA-approved NAAT device performed at a Planned Parenthood clinic.

Although the methods are described herein as being applicable to testing for STI's in other embodiments, the devices and methods described herein can be used to detect any infectious disease. For example, the methods and devices described herein can be used for detection of SNPs in bacteria, viruses, fungi, protozoa that confer resistance or susceptibility to antimicrobials and therefore which guide selection of the most effective medicine. Other methods can include the use of SNPs to genotype infecting microbes as companion or complementary diagnostics to accelerate clinical trials of new antimicrobials 02831 In some embodiments, the methods and devices described herein can be used to detect viruses, including Influenza viruses, Hepatitis C virus, Dengue virus, West Nile virus, Ebola virus, Lassa virus, Sudden acute respiratory syndrome coronavirus 2 (SARS-CoV-2), Sudden acute respiratory syndrome coronavirus (SARS-CoV), Middle East Respiratory Syndrome Coronavirus (MERS-CoV). In some embodiments, the methods and devices are used to detect SARS-CoV-2. In some embodiments, the SARS-CoV-2 sequence is found in the National Center for Biotechnology Information (NCBI) Virus SARS-CoV-2 Data Hub. In some embodiments, the methods and devices are used to detect a nucleic acid encoding a SARS-CoV-2 Spike (S) protein (UniProtKB-P0DTC2). In some embodiments, the methods and devices are used to detect a nucleic acid encoding a protein with at least 95%, at least 96%, at least 97%, at least 98%, or at least 99% similarity to the SARS-CoV-2 Spike (S) Protein (UniProtKB-P0DTC2). In some embodiments, the methods and devices are used to detect a nucleic acid encoding a SARS-CoV-2 S protein with between about 1 to about 20 amino acid mutations, for example, 1, 2, 3, 4, 5, 6, 7, 8, 9, 10, 11, 12, 13, 14, 15, 16, 17, 18, 19, or 20 mutations compared to the protein encoding the SARS-CoV-2 Spike (S) Protein (UniProtKB-P0DTC2) (SEQ ID NO: 1).

Any of the devices, compositions, and methods described herein can be used in connection with the diagnosis and/or treatment of any applicable disease, disorder, or condition. For example, in some embodiments, any of the devices, compositions, and methods described herein can be used to detect SNPs in tissue biopsies and/or blood to genotype cancers for diagnosis, prognostication, treatment (selection of optimal cancer drugs and biologicals), and/or to detect recurrence. In some embodiments, a method can include detection of SNPs to determine (or quantify) a hereditary risk of cancer. In some embodiments, a method can include modifying a treatment protocol in response to the detection. Similarly stated, in some embodiments, a method can include intensified screening (e.g., more frequent colonoscopies or mammograms) in response to the detected SNP.

In some embodiments, a method can include detection of SNPs in human DNA to determine (or quantify) the efficacy of a drug for treatment of an indication. Similarly stated, the methods described herein can be used to determine the effectiveness of a particular drug for a particular patient. In particular, because the SNP can affect drug metabolism (and thus drug dosing), the result can be used to predict an adverse reaction, or has prognostic significance, the methods described herein can be used as a part of a personalized medicine protocol to prescribe a drug and/or dosing regimen.

In some embodiments, a method can include detection of SNPs in maternal blood or amniotic fluid. In this manner, the method can include predicting or quantifying a risk profile for a fetus (e.g., to assess the risk for developmental abnormalities).

Although the methods have been described herein as being applicable to diagnostics, treatment, or other health care applications, in other embodiments, any of the devices, compositions, and methods described herein can be used for any suitable purposes, including food safety, agriculture, environmental preservation, and forensic applications. For example, in some embodiments, any of the devices, compositions, and methods described herein can be used to determine if a crime scene sample is genotypically identical to samples from a list of persons of interest. In other embodiments, any of the devices, compositions, and methods described herein can be used for genotyping to determine if two persons are genetically related, including for paternity assignment purposes.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or microinstructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools.

Additional examples of computer code include, but are not limited to, control signals, encrypted code, and compressed code.

The processor included within a control module (and any of the processors and/or controllers described herein) can be any processor configured to, for example, write data into and read data from the memory of the controller, and execute the instructions and/or methods stored within the memory. Furthermore, the processor can be configured to control operation of the other modules within the controller (e.g., the temperature feedback module and the flow module). Specifically, the processor can receive a signal including temperature data, current measurements or the like and determine an amount of power and/or current to be supplied to each heater assembly, the desired timing and sequence of the piston pulses and the like. For example, in some embodiments, the controller can be an 8-bit PIC microcontroller, which will control the power delivered to various heating assemblies and components within the amplification module 4600. This microcontroller can also contain code for and/or be configured to minimize the instantaneous power requirements on the power source.

In other embodiments, any of the processors described herein can be, for example, an application-specific integrated circuit (ASIC) or a combination of ASICs, which are designed to perform one or more specific functions. In yet other embodiments, the microprocessor can be an analog or digital circuit, or a combination of multiple circuits.

Any of the memory devices described herein can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the pressure feedback module and the position feedback module) can be implemented by the processor and/or stored within the memory.

Although various embodiments have been described as having particular features and/or combinations of components, other embodiments are possible having a combination of any features and/or components from any of embodiments as discussed above.

EXAMPLES

Example 1

An illustrative device was built to simultaneously (1) detect *N. gonorrhoeae* (NG) in a clinical sample, a vaginal swab; and (2) determine whether the NG, if present, is carries a single nucleotide polymorphism (SNP) associated with susceptibility to treatment with the drug ciprofloxacin (Cipro). This handheld device integrates polymerase chain reaction amplification of ompA and gyrA genes from NG in the clinical sample with amplification and detection of a positive control sequence from Neisseria subflava (NS). After introduction of a test solution into the device, the device sequentially adds the reagents necessary for PCR, thermocycles the sample, and conveys the output solution into a detection module. One primer in each pair was biotinylated to permit detection of amplicon.

The detection module was configured to contain three capture probes conjugated to a solid surface, in order: (A) a capture probe for the NS positive control; (B) a capture probe for ompA; (C) an allele-specific capture probe for gryA, Cipro-susceptible allele (gyrA-CIP$^S$), spotted in duplicate or triplicate; (D) an allele-specific capture probe for gryA, Cipro-resistant allele (gyrA-CIP$^R$), spotted in duplicate or triplicate; and in some configureations (E) a non-allele-specific capture probe for gyrA. Detection of biotinylated amplicon was achieved by introduction of streptavidin-conjugated horse radish peroxidase (HRP) followed by 3,3',5,5'-tetramethylbenzidine (TMB) substrate.

The device produces a signal visible to the naked eye as purple color produced by enzymatic conversion of TMB to 3,3',5,5'-tetramethylbenzidine diimine. An onboard electronic digital detection system was integrated into the device to enable automatic quantification and computational processing of the color signal. The device's firmware generates YES/NO calls for both (1) NG detection and (2) Cipro susceptibility.

Figure 22:
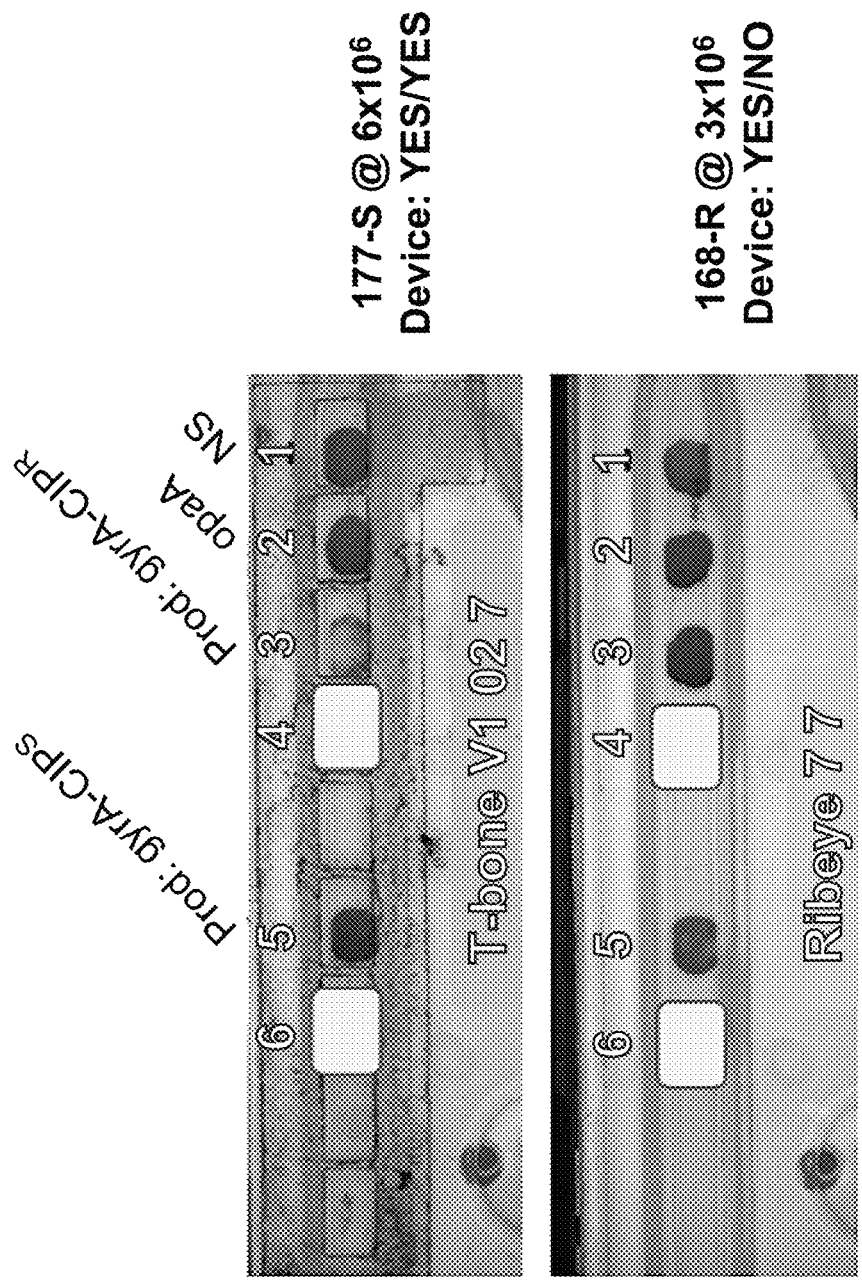
FIG. 22 shows the impact of high microbial load of Cipro-S and Cipro-R strains on gyrA capture probes.

FIG. 22 shows the impact of high microbial load of Cipro-S and Cipro-R strains on gyrA capture probes. Note: Data from capture probe spots in lanes 4 and 6 are not shown as they are early iterations of the S and R capture probes. The final production probes are shown in lanes 3 and 5.

Figures 23A, 23B, 23C:
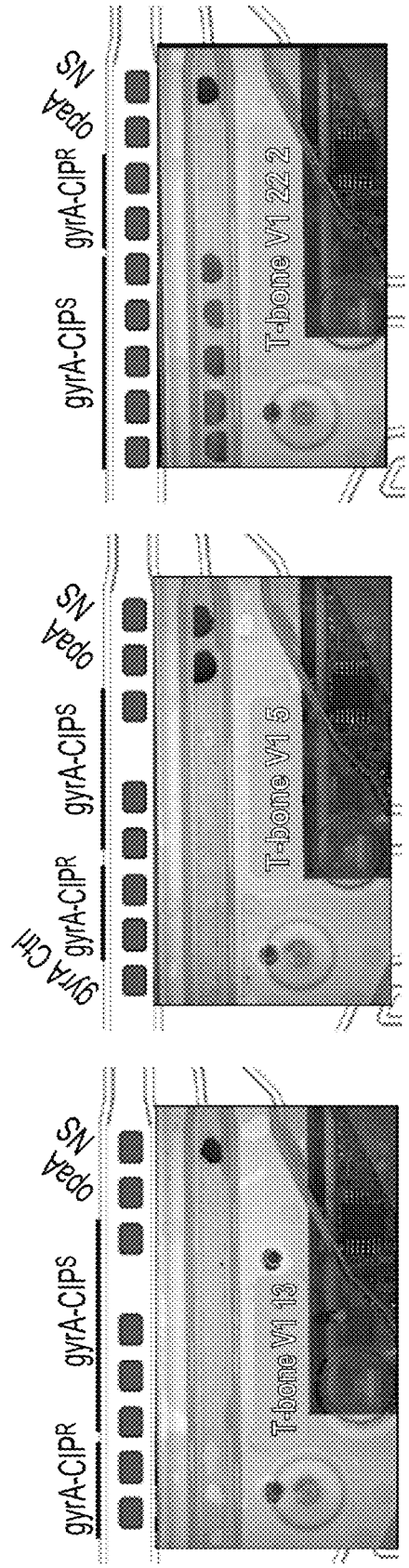
FIGS. 23A-23C show target specificity of PCR primers and probes on integrated devices.

FIGS. 23A-C show the target specificity of PCR primers and probes on integrated devices. The flow cell on the integrated device were spotted with capture probes indicated above each figure. A) gyrA and opaA probes do not cross-react with NS amplicon. Template is NS control pellet in 650 µL of NSM. Primer pellet—multiplex of opaA, gyrA, and NS primers; Capture probes—NS, opaA, and gyrA cipro-R and —S probes. B) gyrA probes do not cross react with opaA amplicon. Template is NS and NG ~7000 copies/mL NG49226 spiked into NSM. Primer pellet—multiplex of NS and opaA primers; Capture probes—NS, opaA, and gyrA cipro-R and —S probes. C) opaA probe does not cross-react with gyrA amplicon. Template is NS and 100 copies/ml of NG 49226 spiked into NSM; Primer pellet—multiplex of gyrA and NS primers only; Probes—NS, opaA, and gyrA cipro-R and —S probes.

Figure 24:
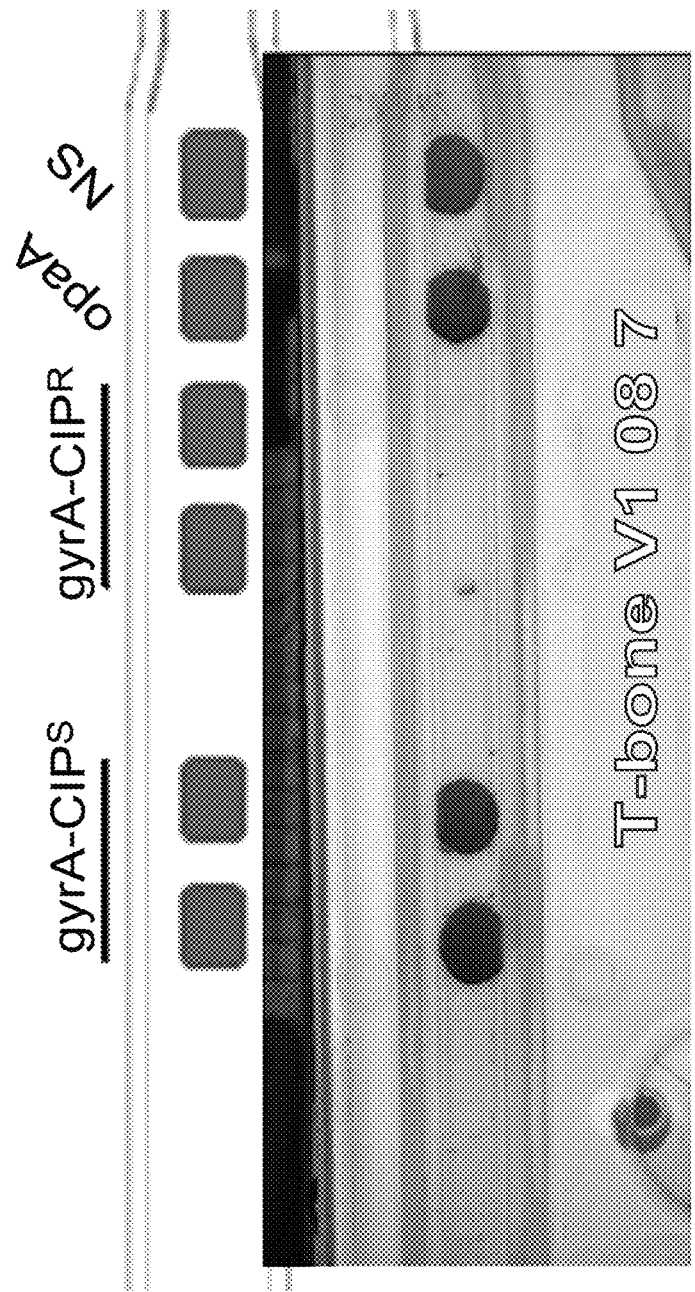
FIG. 24 shows that high microbial loads of CT and TV do not inhibit the NG-gyrA assay.

FIG. 24 shows that high microbial loads of CT and TV do not inhibit the NG-gyrA assay. CT and TV are common causes of vaginitis in women and can be found as concomitant infections with NG. Three devices were tested using as input the "External Positive Control" supplied by Zeptometrix Corporation containing CT, TV, and NG (at unknown concentrations). The presence of high microbial loads of CT and TV did not impact the gyrA assay. The NG strain used by Zeptometrix in the Positive External Control Kit is a cipro-sensitive strain of NG. The device correctly called the inputted sample NG-YES and Cipro-S-YES.

TABLE 1

| Sample | Sequencing Results | Device Results |
|---|---|---|
| Isolate - 177-S | Susceptible | YES/YES |
| Clinical - PE044C | Susceptible | YES/YES |
| Clinical - PE049C | Susceptible | YES/YES |
| Clinical - PE058C | Susceptible | YES/YES |
| Clinical - PE067C | Susceptible | YES/YES |
| Clinical - PE085C | Susceptible | YES/YES |
| Clinical - PE088C | Susceptible | YES/YES |
| Isolate - 171-R | Resistant | YES/NO |
| Clinical - PE057C | Resistant | YES/NO |
| Clinical - PE068C | Resistant | YES/NO |

Figure 25:
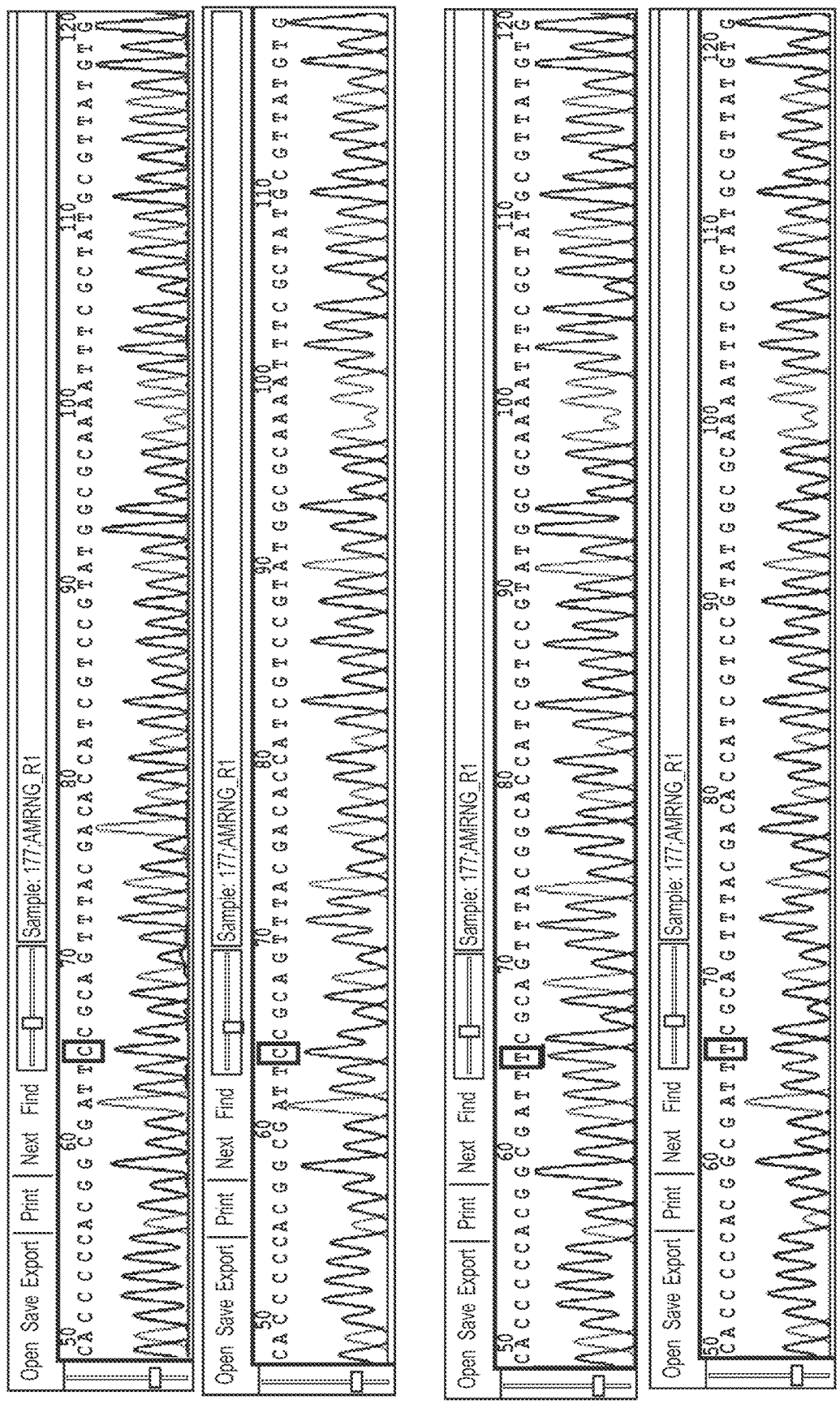
FIG. 25 shows the sequencing traces of the CDC isolate 177-S, 171-R, and clinical samples PE-044C and PE-057C.

Table 1 shows testing of clinical remnant vaginal swab samples. A total of 11 clinical samples were tested on the device. A subset (8) of clinical remnant samples tested on the device were sent to SequeTech to sequence the gyrA Ser-91 containing region. One susceptible and one resistant isolate from the CDC AR library was also sequenced. The sequences of the eight samples were aligned against the CDC isolates. FIG. 25 shows the sequencing traces of the CDC isolate 177-S, 171-R, and clinical samples PE-044C and PE-057C.

Example 2

Design and Evaluations of Primers to Amplify GyrA Region Encompassing Cipro-Resistance SNP Locus 108 bp Amplicon Several primer sets were design to target the SNP locus for serine 91 (Ser-91) in the gyrA gene (SEQ ID NO: 2). A first primer set design is shown underlined below. The target amplicon (uppercase letters) has a calculated melting temperature of 63° C. and a length of 108 bp. The codon TCC (in brackets) encoding a serine in wild-type strains has a SNP at the middle T resulting in a TTC codon encoding phenylalanine. The substitution results in Cipro-resistance.

(SEQ ID NO: 2)

```
  1 atgaccgacg caaccatccg ccacgaccac aaattcgccc tcgaaaccct gcccgtcagc
 61 cttgaagacg aaatgcgcaa aagctatctc gactacgcca tgagcgtcat tgtcgggcgc
121 gcgctgccgg acgttcgcga cggcctaaag ccggtgcacc ggcgcgtact gtacgcgatg
181 cacgagctga aaaataactg gaatgccgcc tacaaaaaat cggCGCGCAT CGTCGGCGAC
241 GTCATCGGTA AATACCACCC CCACGGCGAT [TCC]GCAGTTT ACGACACCAT CGTCCGTATG
301 GCGCAAAATT TCGCTATGCG TTATGTGCTG Atagacggac agggcaactt cggatcggtg
361 gacgggcttg ccgccgcagc catgcgctat accgaaatcc gcatggcgaa aatctcacat
421 gaaatgctgg cagacattga ggaagaaacc gttaatttcg gcccgaacta cgacggtagc
481 gaacacgagc cgcttgtact gccgacccgt ttccccacac tgctcgtcaa cggctcgtcc
541 ggtatcgccg tcggtatggc gaccaacatc ccgccgcaca acctcaccga caccatcaac
601 gcctgtctgc gtctttgga cgaacccaaa accgaaatcg acgaactgat cgacattatc
661 caagccccg acttcccgac cggggcaacc atctacggct tgggcggcgt gcgcgaaggc
721 tataaaacag gccgcggccg cgttgttatg cgcggtaaga cccatatcga acccataggc
```

-continued

```
 781 aaaaacggcg aacgcgaacg catcgttatc gacgaaatcc cctatcaggt caacaaagcc
 841 aagttggtcg agaaaatcgg cgatttggtt cgggaaaaaa cactggaagg catttccgag
 901 ctccgcgacg aatccgacaa atccggtatg cgcgtcgtta tcgagctgaa acgcaacgaa
 961 aatgccgaag tcgtcttaaa ccaactctac aaactgactc cgctgcaaga cagtttcggc
1021 atcaatatgg tggttttggt cgacggacaa ccgcgcctgt taaacctgaa acagattctc
1081 tccgaattcc tgcgccaccg ccgcgaagtc gttacccgac gtacgctttt ccggctgaag
1141 aaggcacgcc atgaagggca tatcgccgaa cggaaagccg tcgcactgtc caatatcgat
1201 gaaatcatca agctcatcaa agaatcgccc aacgcggccg aggccaaaga aaaactgctt
1261 gcgcgccctt gggccagcag cctcgttgaa gaaatgctga cgcgttccgg tctggatttg
1321 gaaatgatgc gtccggaagg attggtcgca acattggtc tgaaaaaaca aggttattac
1381 ctgagcgaga ttcaggcaga tgctatttta cgcatgagcc tgcgaaacct gaccggcctc
1441 gatcagaaag aaattatcga aagctacaaa aacctgatgg gtaaaatcat cgactttgtg
1501 gatatcctct ccaaacccga acgcattacc caaatcatcc gtgacgaact ggaagaaatc
1561 aaaaccaact atggcgacga acgccgcagc gaaatcaacc cgttcggcgg cgacattgcc
1621 gatgaagacc tgattccgca acgcgaaatg gtcgtgaccc tgacccacgg cggctatata
1681 aaaacccagc cgaccaccga ctatcaggct cagcgtcgcg gcgggcgcgg caaacaggcg
1741 gctgccacca agacgaaga ctttatcgaa accctgtttg ttgccaacac gcatgactat
1801 ttgatgtgtt ttaccaacct cggcaagtgc cactggatta aggtttacaa actgcccgaa
1861 ggcggacgca acagccgcgg ccgtccgatt aacaacgtca tccagctgga agaaggcgaa
1921 aaagtcagcg cgattctggc agtacgcgag tttcccgaag accaatacgt cttcttcgcc
1981 accgcgcagg gaatggtgaa aaaagtccaa cttttccgcct ttaaaaacgt ccgcgcccaa
2041 ggcattaaag ccatcgcact caaagaaggc gactacctcg tcggcgctgc gcaaacaggc
2101 ggtgcggacg acattatgtt gttctccaac ttgggcaaag ccatccgctt caacgaatac
2161 tgggaaaaat ccggcaacga cgaagcggaa gatgccgaca tcgaaccgga gatttcagac
2221 gacctcgaag acgaaaccgc cgacaacgaa aacaccctgc caagcggcaa aaacggcgtg
2281 cgtccgtccg gtcgcggcag cggcggtttg cgcggtatgc gcctgcctgc cgacggcaaa
2341 atcgtcagcc tgattacctt cgcccctgaa accgaagaaa gcggtttgca agttttaacc
2401 gccaccgcca acggatacgg aaaacgcacc ccgattgccg attacagccg caaaaacaaa
2461 ggcgggcaag gcagtattgc cattaacacc ggcgagcgca acggcgattt ggtcgccgca
2521 accttggtcg gcgaaaccga cgatttgatg ctgattacca gcggcggcgt gcttatccgt
2581 accaaagtcg aacaaatccg cgaaaccggc cgcgccgcag caggcgtgaa actgattaac
2641 ttggacgaag gcgaaaacctt ggtatcgctg aacgtgttg ccgaagacga atccgaactc
2701 tccggcgctt ctgtaatttc caatgtaacc gaaccggaag ccgagaactg a
```
55

The 108 bp target amplicon therefore has the sequence:

(SEQ ID NO: 3)

```
 1 CGCGCATCGT CGGCGACGTC ATCGGTAAAT ACCACCCCCA CGGCGATTCC GCAGTTTACG

61 ACACCATCGT CCGTATGGCG CAAAATTTCG CTATGCGTTA TGTGCTGA
```

Polymerase chain reaction (PCR) amplification was performed with the following parameters and using the oligonucleotide primers listed below. The reverse primer was 5' labeled to permit detection of the target amplicon. "/5BiosG/" refers to a biotin conjugated to the reverse primer via a linker, having the formula depicted below:

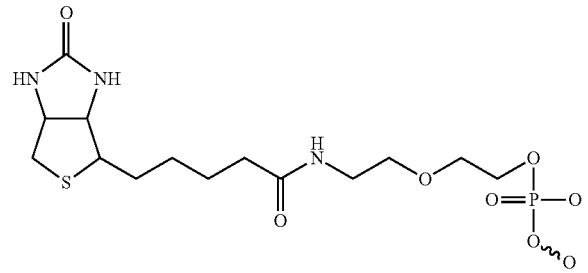 [SMILES: O=C(CCCCC1SCC2NC(=O)NC21)NCCOCCOP(=O)(O)OO]

Final Reaction Concentrations:

```
500 nM Forward Primer:
                                        (SEQ ID NO: 4)
5'-GCGCATCGTCG-3'

500 nM Reverse Primer:
                                        (SEQ ID NO: 5)
5'-/5BiosG/TCAGCACATAACGCATAGC-3'
```

10,000 copies gDNA 75 mM KCl, 4 mM MgCl$_2$, 0.06 U/uL KAPA, 200 uM dNTP

Thermocycling Parameters

| Step | Temperature | Time (mm:ss) | # of cycles |
|---|---|---|---|
| Pre-incubation | 95° C. | 03:00 | 1 |
| Denaturing | 95° C. | 00:05 | 50 |
| Annealing | 60° C. | 00:10 | 50 |

Figure 26A:
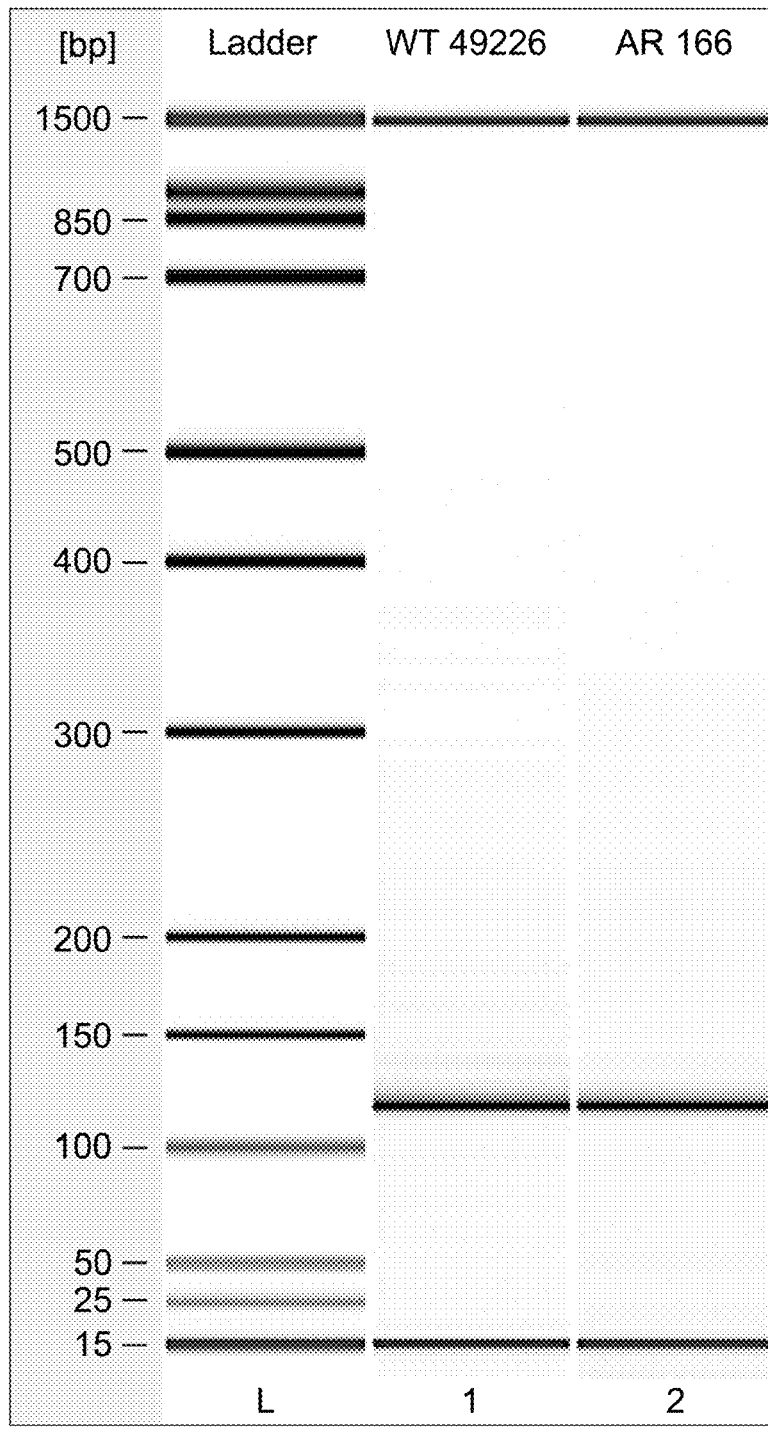
FIG. 26A and FIG. 26B show capillary electrophoresis analysis of target amplicon produced by PCR using polynucleotide samples from various *N. gonorrhoeae* strains as template.
Figure 26B:
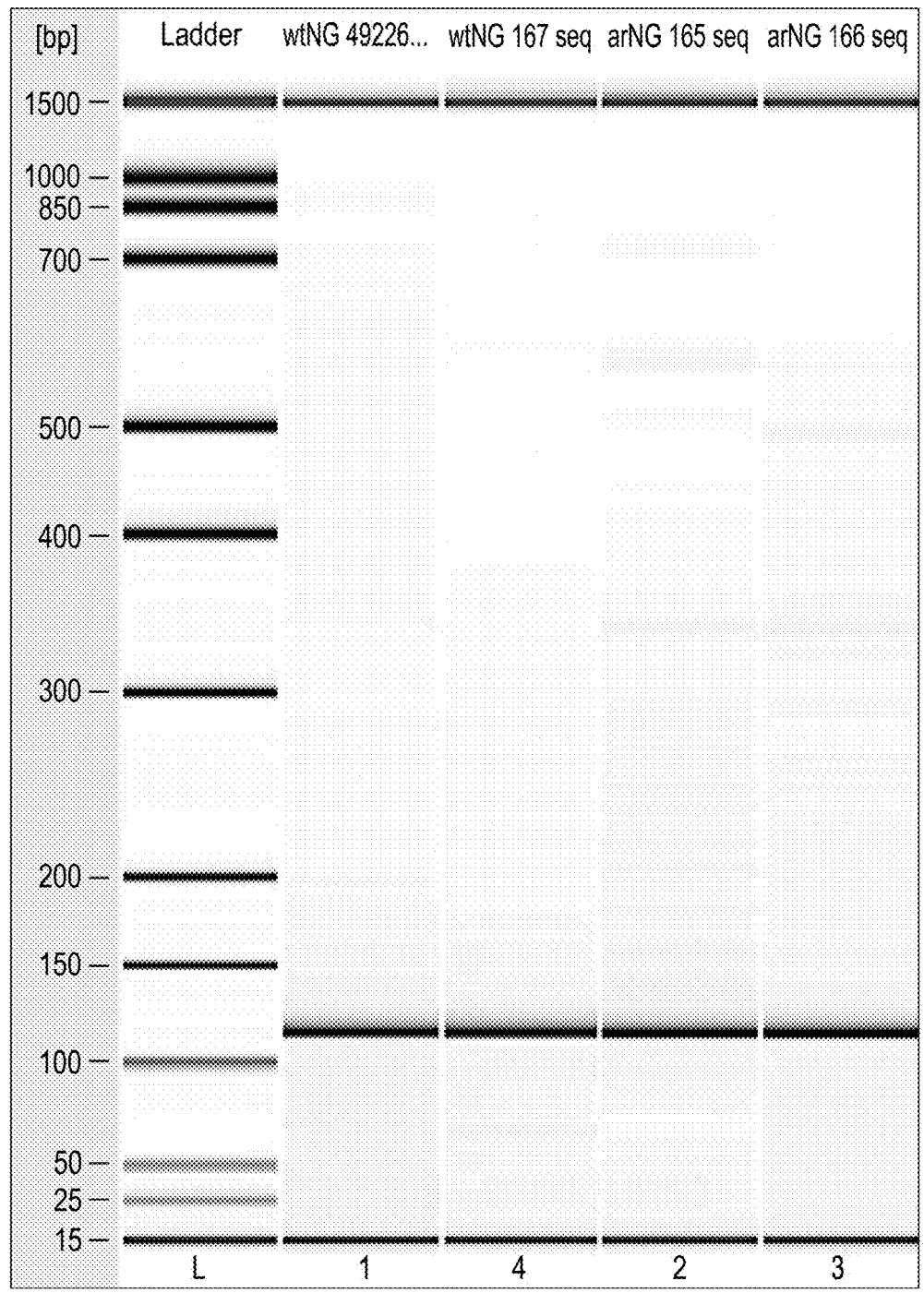

Amplification of the desired amplicon (SEQ ID NO: 3) was confirmed by capillary electrophoresis (FIG. 26A) Similar results were achieved with four experimental strains: (WT) Ser91 ATCC 49226; (WT) Ser91 CDC 167; (AR) Phe91 CDC 165; and (AR) Phe91 CDC 166 (FIG. 26B). Sequencing of the target amplicons confirmed the correct nucleotide was present (data not shown).

34 bp Amplicon

Similar PCR conditions were used to produce a shorter amplicon (SEQ ID NO: 6).

Final Reaction Concentrations:

```
300 nM Forward Primer
                                        (SEQ ID NO: 7)
5'-CCCCCACGGCGATTCC-3'

300 nM Reverse Primer
                                        (SEQ ID NO: 8)
5'-/5BiosG/GATGGTGTCGTAAACTGCGGA-3'
```

10,000 copies gDNA 75 mM KCl, 4 mM MgCl$_2$, 0.06 U/uL KAPA, 200 uM dNTP

Thermocycling Parameters:

| Step | Temperature | Time (mm:ss) | # of cycles |
|---|---|---|---|
| Pre-incubation | 95° C. | 00:20 | 1 |
| Denaturing | 95° C. | 00:01 | 40 |
| Annealing | 60° C. | 00:06 | 40 |

The configuration of forward primer (SEQ ID NO: 9) and the reverse-complement (SEQ ID NO: 11) of the reverse primer (SEQ ID NO: 12) used to generate the target amplicon (SEQ ID NO: 10) are indicated below:

```
                                        (SEQ ID NO: 9)
CCCCCACGGCGATTCC (SEQ ID NO: 10)
CCCCCACGGCGATTCCGCAGTTTACGACACCATC (SEQ ID NO: 11)
TCCGCAGTTTACGACACCATC
```

Figure 27:
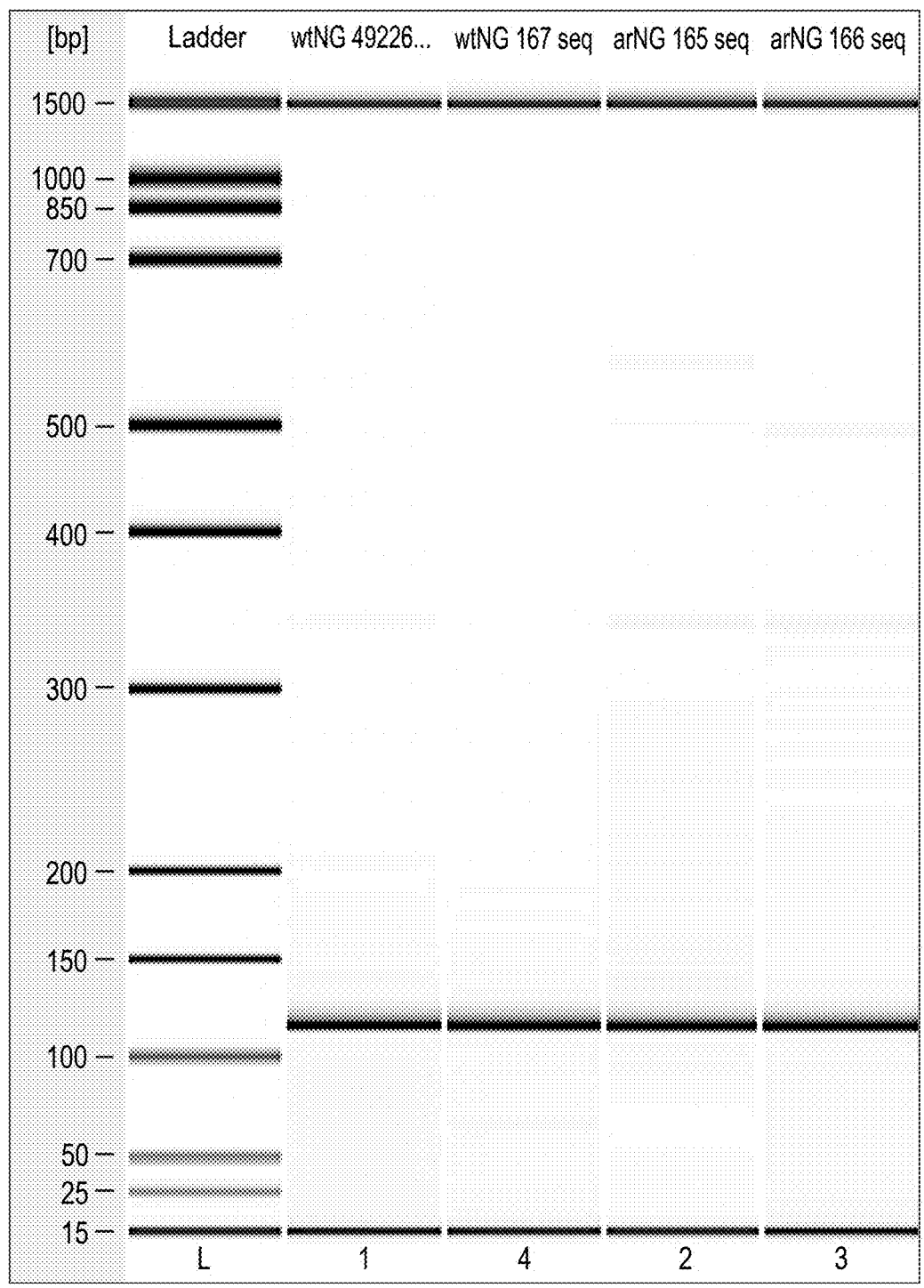
FIG. 27 show capillary electrophoresis analysis of target amplicon produced by PCR using polynucleotide samples from various *N. gonorrhoeae* strains as template.

Due to overlap with Ser-91 gyrA the primers are sequence-specific. Amplification of the 34 bp target amplicon was confirmed by capillary electrophoresis (FIG. 27).

Example 2

Design and Evaluation of Four Probes for SNP Detection at Ser-91 gyrA

Melting temperature analysis was performed on the 108 bp and 34 bp amplicons (Table 3).

TABLE 3

| | Ser91 | Phe91 |
|---|---|---|
| 108 bp | 56.7° C. | 57.5° C. |
| 34 bp | 64.2° C. | 64.6° C. |

Four probes were designed to match the Cipro sensitive allele the Ser91 gryA SNP locus (Table 4). Probes 3 and 4 included intentional mismatches to lower the melting temperatures of the probes. The mismatch to the gyrA sequence is denoted by italics and by an arrow pointing to the mismatched base (mismatch↑). The melting temperatures were calculated using DNASoftware™ Visual OMP™.

TABLE 4

| Probe | SEQUENCE | SEQ ID NO: | Ser91 | Phe91 |
|---|---|---|---|---|
| 1 | /5AmMC6/CGGCGATTCCGCAGTT | 13 | 63.7° C. | 52.4° C. |
| 2 | /5AmMC6/CGGCGATTCCGCAGT | 14 | 64.4° C. | 54.0° C. |
| 3 | /5AmMC6/CGG*T*GATTCCGCAGT mismatch↑ | 15 | 55.7° C. | 41.3° C. |
| 4 | /5AmMC6/CGGC*T*ATTCCGCAGT mismatch↑ | 16 | 52.0° C. | 35.9° C. |

"/5AmMC6/" refers to an amine-reactive moiety conjugated to the probe via a linker, to permit attachment of the probe to the surface of the detection module through reaction with activated carboxylate groups on the surface of the detection module. 5AmMC6 has the formula depicted below:

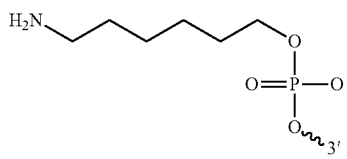

Each of the probes was covalently linked to the surface of microtiter plates by amine-reactive cross-linker chemistry:

1. Dilute probe (with amino linker) to 0.25 μM with sodium bicarbonate buffer.
2. Add 100 μL of the diluted probe to a well of the plate.
3. Seal the plate with sealing film and incubate for 30 minutes at room temperature.
4. Remove the probe solution.
5. Wash twice with 1×PBS.
6. Add 200 μL of Stabilcoat® immunoassay blocker/stabilizer, cover with sealing film and incubate for 2 hours at room temperature.
7. Remove the blocking solution.
8. Store the plate inside a foil bag with desiccant. Store at 2-6° C.

Binding to each of the amplicons from Example 1 was performed according to the following conditions.
Amplicon: 20 nM
Probe: 0.25 μM
Plate Temperature: 48.8-49.8° C.
NTC: no probe+NS amplicon
Pos: NS probe+NS amplicon (reaction positive control)
Steps:
9. Add amplicon and incubate 10 min
10. Wash (0.02% TWEEN®-20 in 1×PBS)
11. Add HRP (1 μg/mL)
12. Wash (0.02% TWEEN®-20 in 1×PBS)
13. Add substrate (TMR PLUS2)

Figure 28:
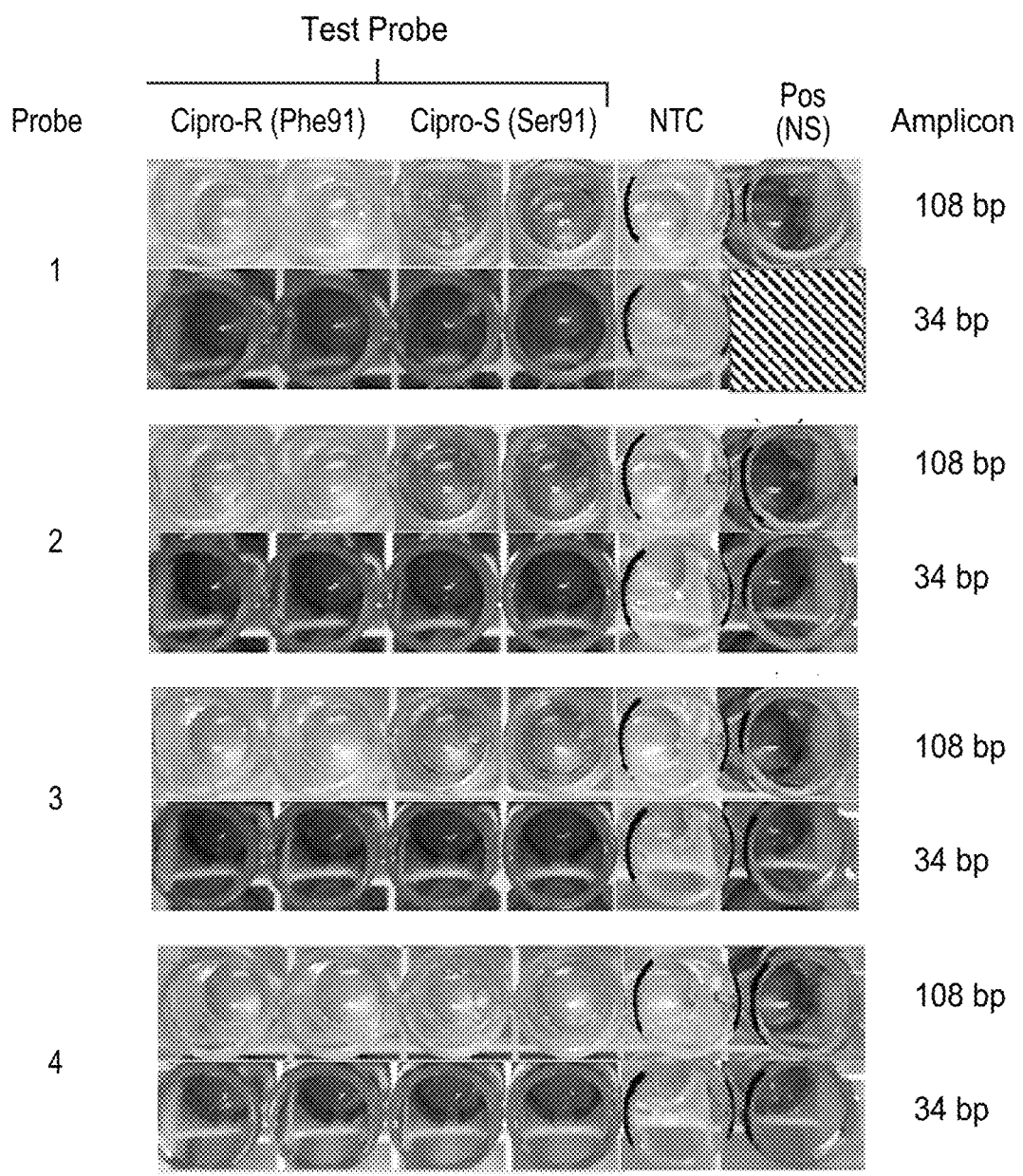
FIG. 28 shows allele-specific hybridization of 108 bp or 34 bp amplicons to surface-linked probes 1-4 in a microtiter plate format.

The binding of target amplicon to probe (detected by HRP-catalyzed conversion of TMR to 3,3',5,5'-tetramethylbenzidine diimine) is shown in FIG. 28. Binding of the 108 bp template to each of the probes discriminates between Cipro-R and Cipro-S alleles at the Ser91 gyrA SNP locus.

Example 3

Design and Evaluation of Four Probes for SNP Detection at Ser-91 gyrA Using Enhanced Wash Buffer Three additional probes were designed to match the Cipro sensitive allele at the Ser91 gryA SNP locus (Table 5). Probes 5, 6 and 8 (like probes 3 and 4) included intentional mismatches to lower the melting temperatures of the probes. The mismatch to the gyrA sequence is denoted by italics and by an arrow pointing to the mismatched base (mismatch↑).

TABLE 5

| Probe | SEQUENCE | SEQ ID NO: | Ser91 | Phe91 |
|---|---|---|---|---|
| 1 | /5AmMC6/CGGCGATTCCGCAGTT | 13 | 63.9° C. | 53.4° C. |
| 2 | /5AmMC6/CGGCGATTCCGCAGT | 14 | 63.2° C. | 51.8° C. |
| 3 | /5AmMC6/CGGTGATTCCGCAGT mismatch↑ | 15 | 55.2° C. | 40.7° C. |
| 4 | /5AmMC6/CGGCTATTCCGCAGT mismatch↑ | 16 | 51.5° C. | 35.2° C. |
| 5 | /5AmMC6/CGGCGATTCGGCAGT mismatch↑ | 17 | 53.4 | 43.8 |
| 6 | n/a | n/a | n/a | n/a |
| 7 | /5AmMC6/CACGGCTATTCCGCAGTTT mismatch↑ | 18 | 58.4 | 46.5 |
| 8 | /5AmMC6/TACGGCTATTCCGCAGTTT mismatch↑  ↑mismatch | 19 | 55.9 | 43.1 |

Figure 29:
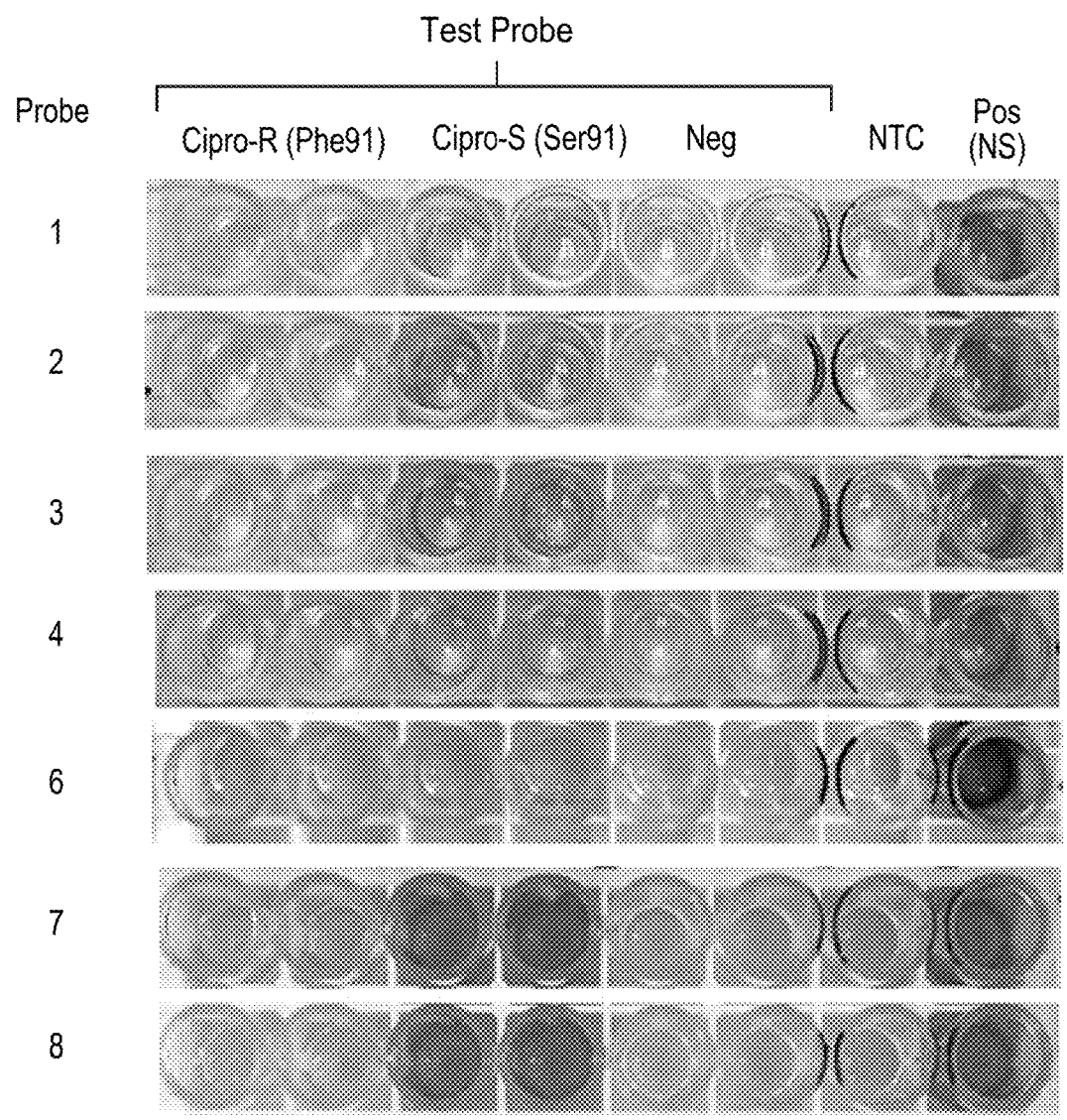
FIG. 29 shows allele-specific hybridization of 108 bp or 34 bp amplicons to surface-linked probes 1-5 and 7-8 in a microtiter plate format.

Results for testing of these probes according to the following protocol are shown in Table 6 and Table 7 and FIG. 29. Binding of the 108 bp template to each of the probes discriminates between Cipro-R and Cipro-S alleles at the Ser91 gyrA SNP locus.
Conditions
Amplicon: 20 nM
Probe: 0.25 μM
Plate Temperature: 48.5-49.8° C.
Neg: Test probe+NS amplicon
NTC: no probe+NS amplicon
Pos: NS probe+NS amplicon (reaction positive control)
Enhanced Wash Buffer
1× phosphate buffered saline (PBS)
76.92 mM KCl
1.92 mM $MgCl_2$
0.03% ProClin300 (v/v)
0.02% Tween-20 (v/v), pH 7.4
Steps
1. Add amplicon and incubate 10 min
2. Wash (enhanced wash buffer)
3. Add HRP (1 μg/mL)
4. Wash (enhanced wash buffer)
5. Add substrate (TMB PLUS2)

TABLE 6

| | 640 nm Absorbance | | | | |
|---|---|---|---|---|---|
| Probe | Cipro-R (Phe91) | Cipro-S (Ser91) | Neg | NTC | Pos (NS) |
| 1 | 0.047 | 0.098 | 0.042 | 0.043 | 0.658 |
| 2 | 0.062 | 0.272 | 0.0397 | 0.058 | 0.528 |

TABLE 6-continued

| | 640 nm Absorbance | | | | |
|---|---|---|---|---|---|
| Probe | Cipro-R (Phe91) | Cipro-S (Ser91) | Neg | NTC | Pos (NS) |
| 3 | 0.043 | 0.304 | 0.040 | 0.046 | 0.625 |
| 4 | 0.0453 | 0.139 | 0.042 | 0.067 | 0.544 |
| 5 | 0.045 | 0.0780 | 0.046 | 0.045 | 0.884 |
| 6 | n/a | n/a | n/a | n/a | n/a |
| 7 | 0.919 | 0.610 | 0.038 | 0.045 | 0.617 |
| 8 | 0.058 | 0.535 | 0.039 | 0.038 | 0.670 |

TABLE 7

| | Signal: Background | | | | |
|---|---|---|---|---|---|
| Probe | Cipro-R. (Phe91) | Cipro-S (Ser91) | Neg | NTC | Pos (NS) |
| 1 | 1.113 | 2.329 | 1 | N/A | N/A |
| 2 | 1.568 | 6.848 | 1 | N/A | N/A |
| 3 | 1.069 | 7.527 | 1 | N/A | N/A |
| 4 | 1.079 | 3.302 | 1 | N/A | N/A |
| 5 | n/d | n/d | n/d | n/d | n/d |
| 6 | n/a | n/a | n/a | n/a | n/a |
| 7 | n/d | n/d | n/d | n/d | n/d |
| 8 | n/d | n/d | n/d | n/d | n/d |

Example 4

Design and Evaluation of 68 bp Target Amplicon Using Second Probe as Internal Control An additional target amplicon was tested using primers designed to flank the gryA-Ser91 SNP locus and to produce a 68 bp product:

```
Forward Primer:
                                    (SEQ ID NO: 4)
5'-GCGCATCGTCG-3'

Reverse Primer:
                                    (SEQ ID NO: 20)
5'-/5BiosG/GATGGTGTCGTAAACTGCG-3'

Control Probe:
                                    (SEQ ID NO: 21)
5'-TCATCGGTAAATACCACCCCC-3'

Target Amplicon:
                                    (SEQ ID NO: 22)
CGCGCATCGTCGGCGACGTCATCGGTAAATACCACCCCCACGGCGATTCC

GCAGTTTACGACACCATC
```

The control probe (SEQ ID NO: 21) was to designed to bind within the same target amplicon as the allele-specific probes 1-5 and 7-8. The control probe and allele-specific probe binding sites do not overlap. Template from Cipro-sensitive strains CDC 167 and CDC 175 or from Cipro-resistant strains CDC 166 and CDC168 was PCR-amplified using standard parameters.

Figure 30:
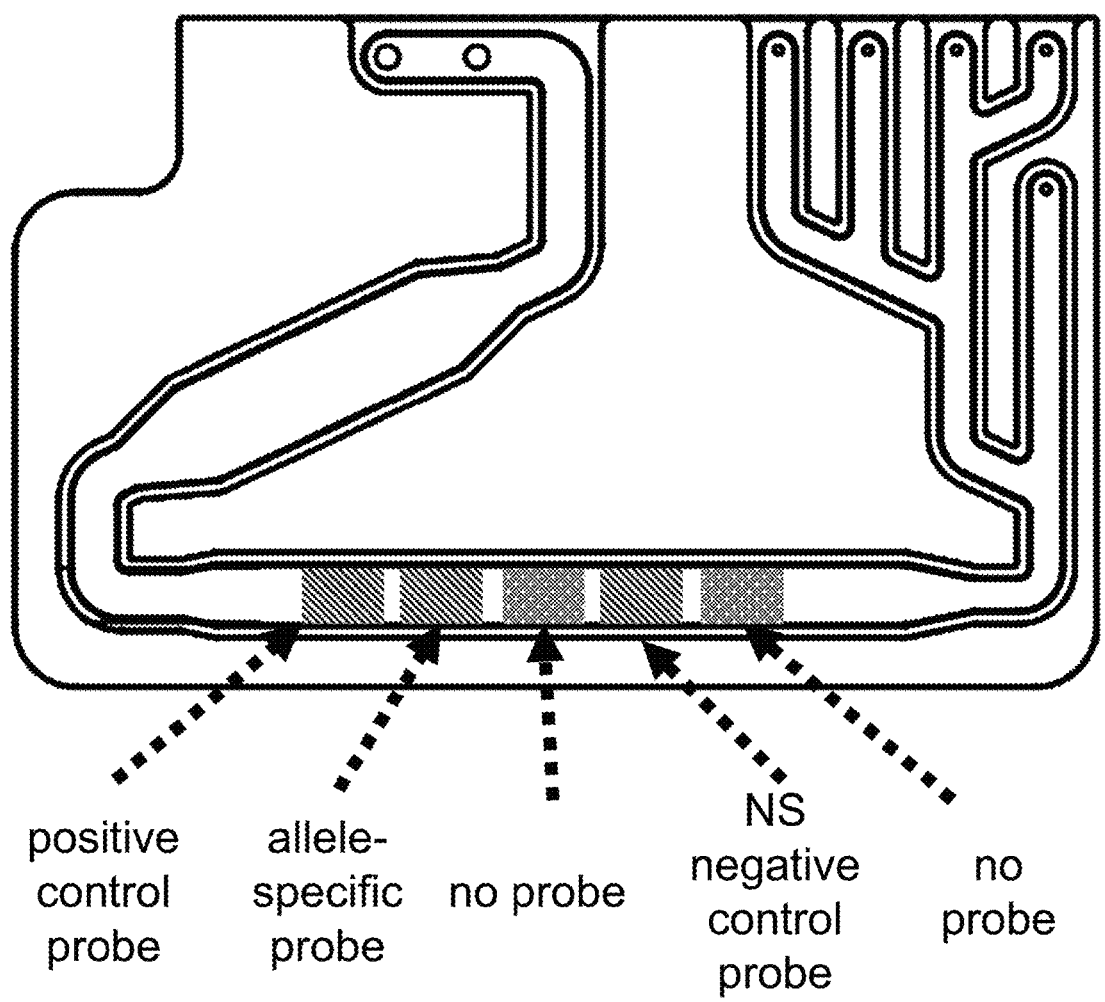
FIG. 30 is a schematic illustration of a detection module showing the position of five detection surfaces used in experimental evaluation of probe designs.

A detection module (also termed a flow cell) was configured as shown in FIG. 30. The 68 bp amplicons from each strain were passed through the flow cell; detection reagent 1 (HRP) was then added; followed by a wash with enhanced wash buffer; and substrate (TMB) addition using the following volumes and flow rates. All steps were performed at 52° C.

1. Amplicon hybridization. 60 µL. 0.35 µL/s.
2. Enzyme (HRP). 270 µL. 5 µL/s
3. Wash (Enhanced Wash Buffer) 270 µL. 5 µL/s
4. Substrate. 270 µL. 5 µL/s. 2×

Figure 31:
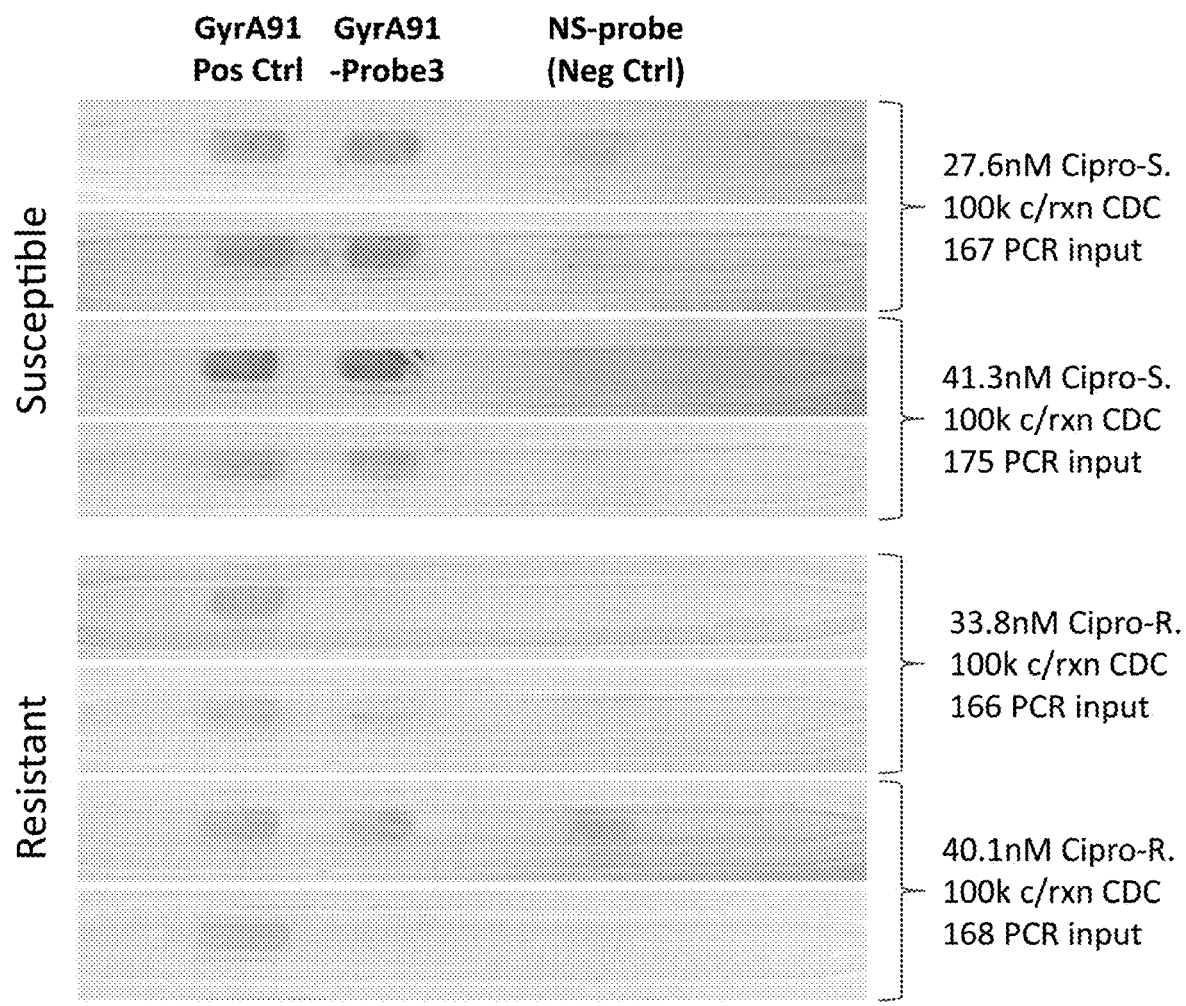
FIG. 31 shows colorimetric detection of target amplicon from susceptible (Cipro-S) and resistance (Cipro-R) strains of gonorrhea binding to allele-specific probe 3.

The experiments demonstrates that control probe (SEQ ID NO: 21) and allele-specific probe 3 (SEQ ID NO: 15) discriminate between Cipro-sensitive (Cipro-S) and Cipro-resistance (Cipro-R) strains (FIG. 31).

Figure 32:
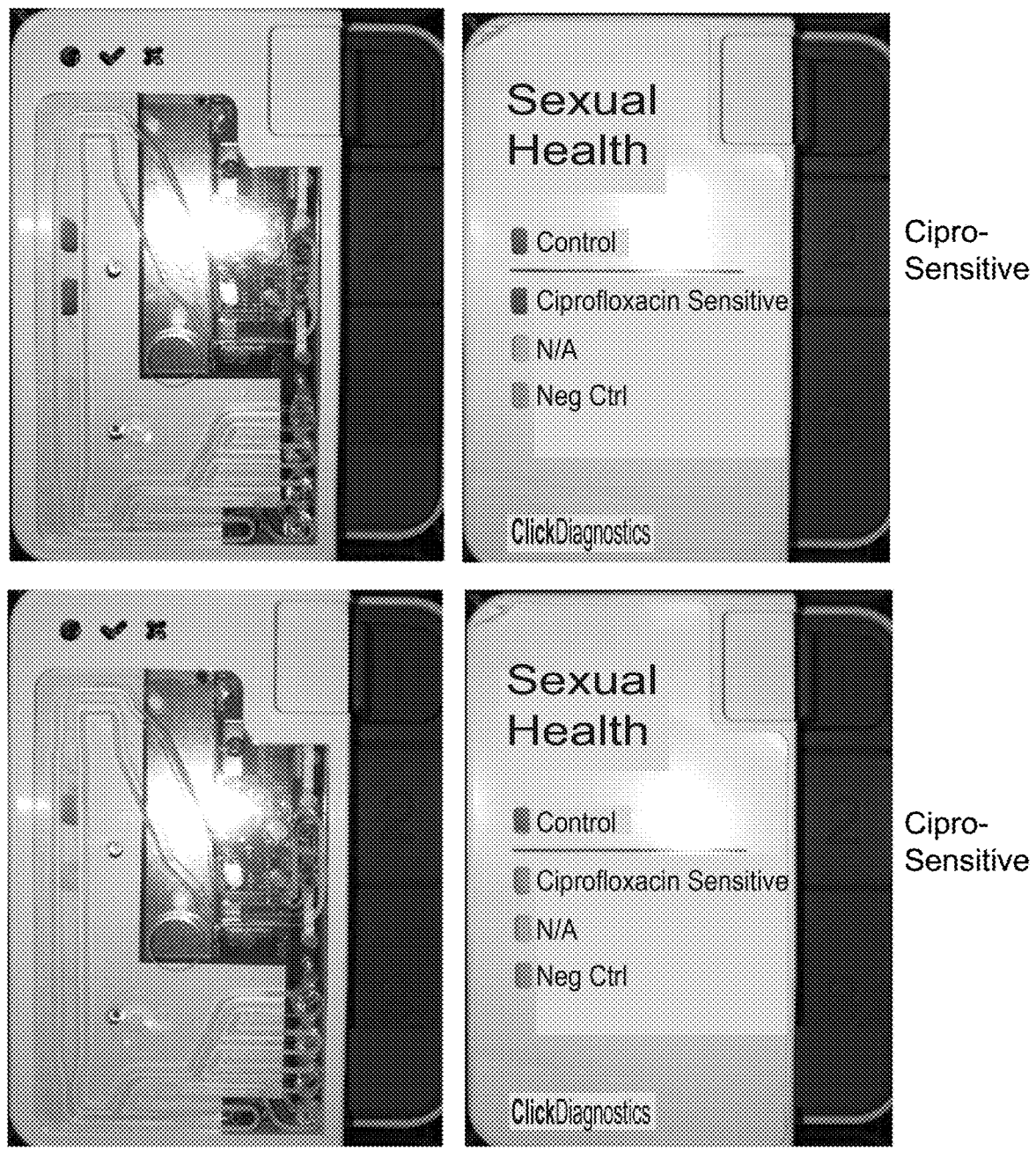
FIG. 32 and FIG. 33 show testing of illustrative devices demonstrating discrimination between Cipro-sensitive and Cipro-resistant strains.
Figure 33:
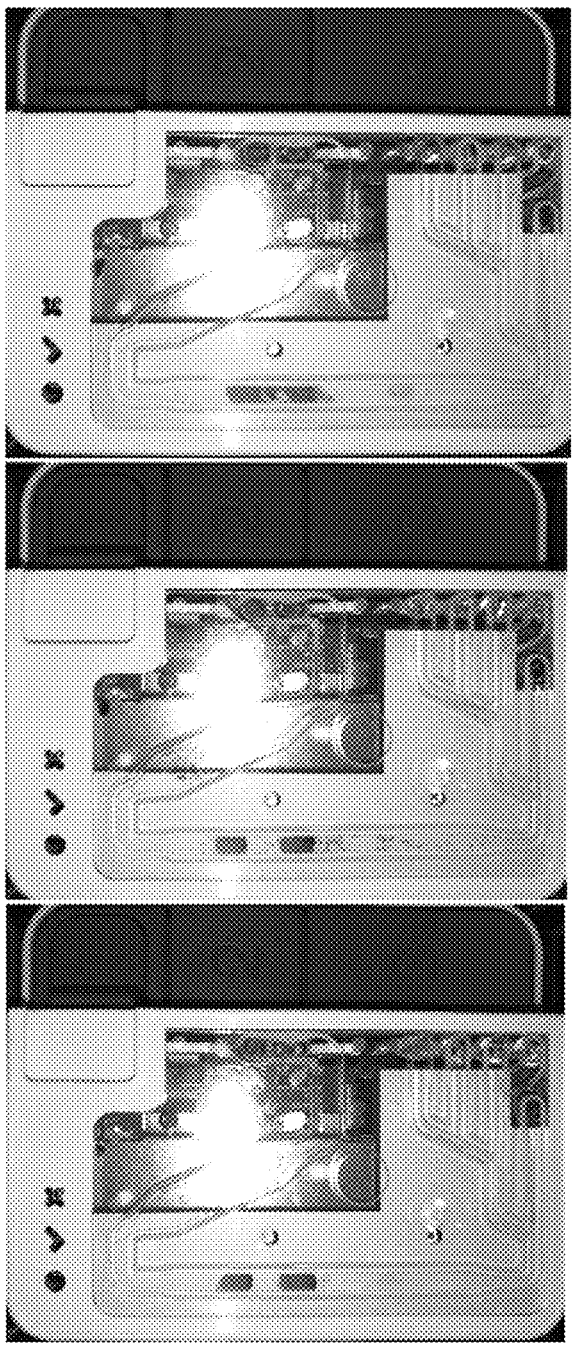
Figure 33:
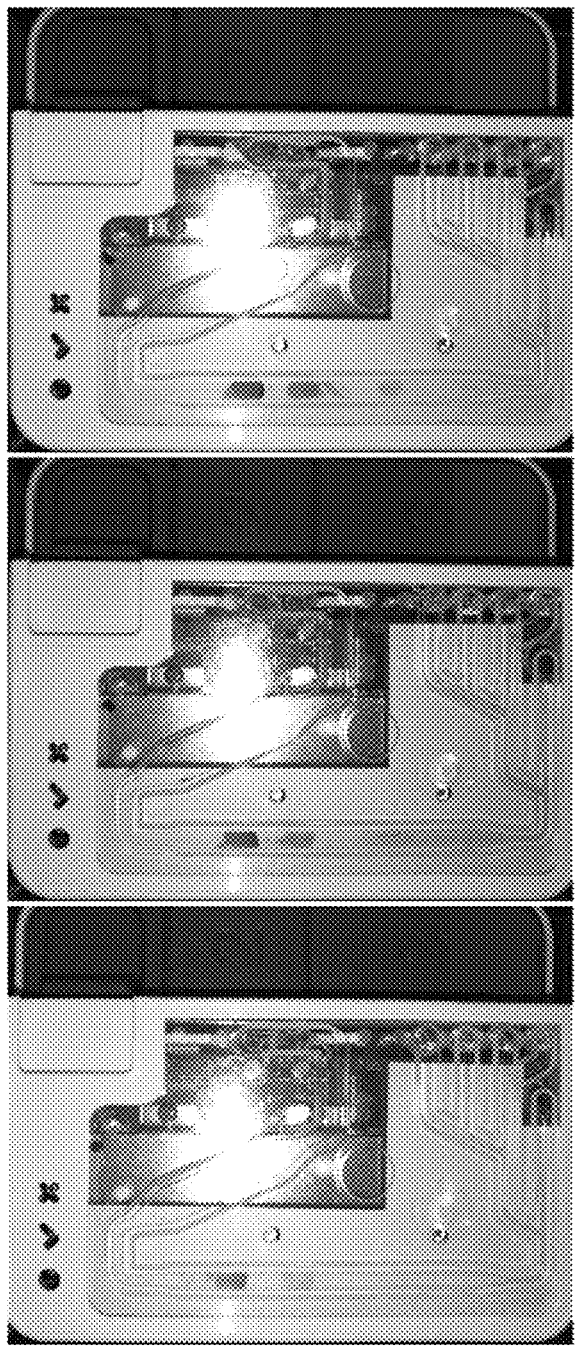

To determine a limit of detection, experiments were run under similar conditions using as few as 100,000 bacterial genomes per reaction as the input material. FIG. 32 and FIG. 33 demonstrates that the device discriminates between sensitive and resistance strains even at this low sample concentration. Signal from the allele-specific probe is reduced compared to signal from the control probe when template from Cipro-resistant strains is tested. Strong signal from both probes is observed when template from Cipro-sensitive strains is tested.

For foregoing examples are for illustration only and do not limit the scope of the invention, which is defined by the following claims.

What is claimed is:

1. A molecular diagnostic device, comprising:
a sample preparation module containing a primer set and being configured to mix the primer set with a biological sample to produce an input solution, the biological sample suspected of comprising a polynucleotide from a target organism, the primer set targeting a first genetic locus in a polynucleotide associated with the target organism and a second genetic locus in a polynucleotide associated with a single nucleotide polymorphism (SNP) locus in the polynucleotide;
an amplification module including a reaction volume and a heater, the reaction volume configured to receive the input solution, the heater configured to convey thermal energy into the reaction volume to amplify the polynucleotide to produce an output solution containing a first amplicon comprising the first genetic locus and a second amplicon comprising the second genetic locus;
a detection module including a first probe, a second probe, and a third probe, the first probe designed to bind to the first genetic locus, the second probe designed to bind to the second genetic locus if the second genetic locus comprises a first target allele associated with resistance of the target organism to a treatment, the third probe designed to bind to the second genetic locus if the second genetic locus comprises a second target allele associated with susceptibility of the target organism to the treatment; and
a reagent module containing a reagent formulated to facilitate production of a first signal, a second signal, and a third signal, the first signal indicating the presence of the bound first genetic locus, the second signal indicating the presence of the bound second genetic locus that comprises the first target allele, and the third signal indicating the presence of the bound second genetic locus that comprises the second target allele, wherein
the second probe has a second probe melting temperature for hybridization to the second genetic locus comprising the first target allele,
the third probe has a third probe melting temperature for hybridization to the second genetic locus comprising the second target allele, and
the second probe melting temperature is different from the third probe melting temperature.

2. The molecular diagnostic device of claim 1, wherein:
the detection module includes a first detection surface to which the first probe is adhered, a second detection surface to which the second probe is adhered, and a third detection surface to which the third probe is adhered; and
the first signal is produced from the first detection surface, the second signal is produced from the second detection surface, and the third signal is produced from the third detection surface.

3. The molecular diagnostic device of claim 2, wherein the reagent is formulated to produce a first color product from the first detection surface, a second color product from the second detection surface, and a third color product from the third detection surface when the reagent is conveyed into the detection module.

4. The molecular diagnostic device of claim 3, wherein the sample preparation module, the amplification module, the detection module, and the reagent module are integrated within a housing, the detection module being positioned within the housing such that the first color product, the second color product, and the third color product are viewable via a detection opening of the housing.

5. The molecular diagnostic device of claim 2, further comprising:
an electronic system including a digital read module implemented in at least one of a memory or a processing device, the digital read module configured to:
A) detect the presence of the first signal, the second signal, and the third signal and
B) produce an electronic output associated with the presence of at least one of the first signal, the second signal, and the third signal.

6. The molecular diagnostic device of claim 5, wherein:
the electronic system includes at least one light source and at least one photodetector;
the at least one light source being configured to produce a first light beam aligned with the first detection surface, a second light beam aligned with the second detection surface, and a third light beam aligned with the third detection surface;
the at least one photodetector being configured to measure at least one of a reflection or an attenuation of the first light beam, a reflection or an attenuation of the second light beam, or a reflection or an attenuation of the third light beam; and
the digital read module configured to detect the presence of the first signal based on the reflection or the attenuation of the first light beam, detect the presence of the second signal based on the reflection or the attenuation of the second light beam, and detect the presence of the third signal based on the reflection or the attenuation of the third light beam.

7. The molecular diagnostic device of claim 6, wherein the detection module includes a reflective member positioned such that the first detection surface, the second detection surface, and the third detection surface are each between the reflective member and the at least one light source and the at least one photodetector.

8. The molecular diagnostic device of claim 1, wherein the reagent is stored within a sealed container within the molecular diagnostic device, the reagent being any one of a horseradish peroxidase enzyme with a streptavidin linker or a substrate formulated to produce the first signal when the substrate is contacted with the horseradish peroxidase enzyme with the streptavidin linker.

9. A detection module of a molecular diagnostic device configured to detect the presence of a target organism and the presence of at least one of a first target allele within the target organism associated with resistance to a treatment or a second target allele within the target organism associated with susceptibility to the treatment, the detection module comprising:
a flow member defining a detection channel configured to receive an output solution from an amplification module, the output solution containing a first amplicon comprising a first genetic locus in a polynucleotide associated with the target organism and a second amplicon comprising a second genetic locus in a polynucleotide associated with a single nucleotide polymorphism (SNP) locus in the polynucleotide;
a first detection surface within the detection channel, a first probe being adhered to the first detection surface, the first probe designed to bind to the first genetic locus in a polynucleotide associated with the target organism and facilitate production of a first signal indicating the presence of the target organism;

a second detection surface within the detection channel, a second probe being adhered to the second detection surface, the second probe designed to bind to the second genetic locus if the second genetic locus comprises the first target allele and facilitate production of a second signal indicating the presence of the first target allele within the target organism associated with resistance to the treatment; and a third detection surface within the detection channel, a third probe being adhered to the third detection surface, the third probe designed to bind to the second genetic locus if the second genetic locus comprises the second target allele and facilitate production of a third signal indicating the presence of the second target allele within the target organism associated with susceptibility to the treatment.

10. The detection module of claim 9, wherein the second probe and the third probe are asymmetrical.

11. The detection module of claim 9, wherein
the second probe has a second probe melting temperature for hybridization to the second genetic locus comprising the first target allele,
the third probe has a third probe melting temperature for hybridization to the second genetic locus comprising the second target allele, and
the second probe melting temperature is lower than the third probe melting temperature.

12. The detection module of claim 11, wherein a difference between the second probe melting temperature and the third probe melting temperature is at least 5° C.

13. The detection module of claim 9, wherein the second probe comprises an exact match to a SNP associated with drug susceptibility.

14. The detection module of claim 13, wherein the second probe comprises an exact match to the codon encoding gyrA Ser-91.

15. The detection module of claim 9, wherein the third probe comprises an exact match to a SNP associated with drug resistance.

16. The detection module of claim 15, wherein the third probe comprises an exact match to the codon encoding gyrA Phe-91, gyrA Tyr-91, gyrA Asp-95 and gyrA Gly-95.

17. A probe set for detecting presence and susceptibility of a target organism to a drug, comprising:

a first oligonucleotide probe substantially complementary to a non-polymorphic locus in a polynucleotide of the target organism;

a second oligonucleotide probe substantially complementary to a polymorphic locus in a polynucleotide of the target organism, the second probe comprising a nucleotide sequence matched to an allele of the polymorphic locus associated with resistance to the drug; and a third oligonucleotide probe substantially complementary to the polymorphic locus, the third probe comprising a nucleotide sequence matched to an allele of the polymorphic locus associated with susceptibility to the drug, wherein the second oligonucleotide probe has a second probe melting temperature for hybridization to the polymorphic locus comprising the allele of the polymorphic locus associated with resistance to the drug, the third oligonucleotide probe has a third probe melting temperature for hybridization to the polymorphic locus comprising the allele of the polymorphic locus associated with susceptibility to the drug, and the second oligonucleotide probe melting temperature is different from the third oligonucleotide probe melting temperature.

18. The probe set of claim 17, wherein
the second oligonucleotide probe melting temperature is determined by computational or experimental hybridization to the allele of the polymorphic locus associated with resistance to the drug; and/or
the third oligonucleotide probe melting temperature is determined by computational or experimental hybridization to the allele of the polymorphic locus associated with susceptibility to the drug.

19. The probe set of claim 17, wherein the polymorphic locus comprises a single nucleotide polymorphism (SNP).

20. The probe set of claim 17, wherein the probe set is formulated to produce at least one signal indicating the presence of the target organism and susceptibility of the target organism to the drug upon contact with one or more amplicons produced by amplification of one or more loci in the polynucleotide of the target organism.

* * * * *